(12) United States Patent
Masli

(10) Patent No.: US 10,093,979 B2
(45) Date of Patent: Oct. 9, 2018

(54) POLYMORPHISM OF THROMBOSPONDIN-1 AS A BIOMARKER FOR SUSCEPTIBILITY TO DRY EYE

(71) Applicant: TRUSTEES OF BOSTON UNIVERSITY, Boston, MA (US)

(72) Inventor: Sharmila Masli, Brookline, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 14/774,044

(22) PCT Filed: Mar. 14, 2014

(86) PCT No.: PCT/US2014/027343
§ 371 (c)(1),
(2) Date: Sep. 9, 2015

(87) PCT Pub. No.: WO2014/152440
PCT Pub. Date: Sep. 25, 2014

(65) Prior Publication Data
US 2016/0024580 A1    Jan. 28, 2016

Related U.S. Application Data

(60) Provisional application No. 61/800,881, filed on Mar. 15, 2013.

(51) Int. Cl.
*C12Q 1/68* (2018.01)
*C12Q 1/6883* (2018.01)

(52) U.S. Cl.
CPC ..... *C12Q 1/6883* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

2009/0253585 A1    10/2009 Diatchenko et al.

OTHER PUBLICATIONS

Contreras-Ruiz et al; . ARVO Annual Meeting; Jun. 2013; vol. 54, Issue 15; abstract.*
Calonge, M (Survey of Opthalmology, vol. 45, Mar. 2001; pp. S227-S239).*
Turpie et al., "Sjogren's Syndrome-Like Ocular Surface Disease in Thrombospondin-1 Deficient Mice," The American Journal of Pathology, 175(3):1136-1147 (2009).
Adams et al., "The Thrombospondins", Cold Spring Harbor Perspectives in Biology 3:a009712 (2011). (30 pages).
Barabino et al., "The Controlled-Environment Chamber: A New Mouse Model of Dry Eye", Investigative Ophthalmology & Visual Science 46(8):2766-2771 (2005).
Dursun et al., "A Mouse Model of Keratoconjunctivitis Sicca", Investigative Ophthalmology & Visual Science 43(3):632-638 (2002).
Hannah et al., "A Polymorphism in Thrombospondin-1 Associated with Familial Premature Coronary Artery Disease Alters Ca2+ Binding", The Journal of Biological Chemistry 279(50):51915-51922 (2004).
Niederkorn et al., "Desiccating Stress Induces T Cell-Mediated Sjögren's Syndrome-Like Lacrimal Keratoconjunctivitis", The Journal of Immunology 176:3950-3957 (2006).
Savini et al., "The challenge of dry eye diagnosis", Clinical Ophthalmology 2(1):31-55 (2008).
Sekiyama et al., "Unique Distribution of Thrombospondin-1 in Human Ocular Surface Epithelium", Investigative Ophthalmology & Visual Science 47(4):1352-1358 (2006).
Stern et al., "Dry Eye as a Mucosal Autoimmune Disease", International Reviews of Immunology 32(1):19-41 (2013).
Topol et al., "Single Nucleotide Polymorphisms in Multiple Novel Thrombospondin Genes May Be Associated With Familial Premature Myocardial Infarction", Circulation 104:2641-2644 (2001).
Zwicker et al., "The thrombospondin-1 N700S polymorphism is associated with early myocardial infarction without altering von Willebrand factor multimer size", Blood 108(4):1280-1283 (2006).

* cited by examiner

Primary Examiner — Jehanne S Sitton
(74) Attorney, Agent, or Firm — Ronald I. Eisenstein; Nixon Peabody LLP

(57) ABSTRACT

Embodiments of the invention relate to single nucleotide polymorphisms (SNPs) in Thrombospondin 1 gene (THBS1) that are herein linked to an increased risk for dry eye (also known as keratoconjunctivitis). The polymorphisms disclosed herein are directly useful for the diagnosis of an increased risk for dry eye, as well as for the determination of patient treatment pre- and post-surgery (e.g. pre and post refractive eye surgery) or in a patient having a condition associate with dry eye (e.g. diabetes, lupus, scleroderma, Sjogren's syndrome, thyroid disorders, vitamin A deficiency, and rheumatoid arthritis). Computer systems and medium are also enclosed. The SNPs can be present in unique combinations, or as specific haplotypes indicative of dry eye. The SNPs linked to an increased risk for dry eye include rs1478604, rs2228261, and rs2292305.

7 Claims, 13 Drawing Sheets
Specification includes a Sequence Listing.

Diagnostic criteria for post-refractive surgery dry eye.

| CONTROL | DRY EYE | |
|---|---|---|
| Normal | Intermediate | Dry Eye |
| ✓ No symptoms | ✓ No Symptoms | ✓ Symptoms |
| ✓ No punctal plugs | ✓ No punctal plugs | ✓ Punctal plugs |
| ✓ No superficial punctate keratitis (SPK) | ✓ No SPK | ✓ SPK |
| ✓ Rose Bengal (RB) score =0 | ✓ 0 ≤ RB score ≤ 1 | ✓ RB score >1 |
| | | ✓ Or combination of 2 of the following: |
| ✓ TBUT ≥ 10 | ✓ 5 ≤ TBUT < 10 | - TBUT < 5 |
| ✓ Schirmer tear test ≥ 10 | ✓ 5 ≤ Schirmer < 10 | - Schirmer tear test < 5 |
| ✓ McMonnies Questionnaire: | ✓ McMonnies: | - McMonnies > 20 |
| ✓ Males ≤ 10 | ✓ 10< males ≤ 20 | |
| ✓ Females ≤ 15 | ✓ 15 < females ≤ 20 | |

Punctal plugs: device inserted into the tear duct to prevent drainage of liquid from the eye. Superficial punctate keratitis (SPK): is death of small groups of cells on the surface of the cornea (usually pinpoint). TBUT: Tear break up time

*FIG. 6*

Description and location of the analyzed THBS1 polymorphisms.

| SNP | ID | MAF | Function | mRNA Position | mRNA Allele change | Protein Position | Protein Residue change | Location |
|---|---|---|---|---|---|---|---|---|
| SNP1 | rs1478604 | 0.41 | UTR-5 | 42 | T→C | NA | NA | UTR-5 |
| SNP2 | rs2228261 | 0.241 | Synonymous | 1589 | AAC→AAT | 470 | N→N | Type I Repeats |
| SNP3 | rs2292305 | 0.253 | Missense | 1746 | ACA→GCA | 523 | T→A | Type II Repeats |
| SNP4 | rs2228262 | 0.053 | Missense | 2278 | AAT→AGT | 700 | N→S | Type III Repeats |
| SNP5 | rs3743125 | 0.163 | UTR-3 | 3970 | G→A | NA | NA | UTR-3 |

SNP: single nucleotide polymorphism; ID: Identification number, MAF: minor allelic frequency; UTR: untranslated region; NA: non applicable.

FIG. 7

Characteristics of total population.

| | Control | Dry Eye |
|---|---|---|
| N (% of Total) | 26 (18.2%) | 117 (81.8%) |
| Age (years±SD) | 29.7 ±5.4 | 29.9 ±5.2 |
| Female/Male | 14/12 | 60/57 |
| Schirmer test with anesthesia (mm)[#] | 25.09 ±8.87 | 18.26 ±10.06* |
| Rose Bengal Staining[#] | 0.00 ±0.00 | 0.14 ± 0.40 |
| TBUT (s)[#] | 14.83 ±7.30 | 14.36 ±7.89 |
| McMonnies Questionnaire[#] | 7.42 ±4.23 | 9.38 ±4.05* |

[#]: Clinical assessments 12 months post-refractive surgery; TBUT: Tear break-up time. SD: standard deviation; S: seconds. *p-value< 0.05

Characteristics of study population.

| | Control | Dry Eye |
|---|---|---|
| N (% of Total) | 16 (21.3%) | 59 (78.7%) |
| Age (years±SD) | 28.9±5.6 | 29.4±5.0 |
| Female/Male | 6/10 | 20/39 |
| Schirmer test with anesthesia (mm)[A] | 29.00 ±7.00 | 17.84 ±10.76* |
| Rose Bengal Staining[A] | 0.00 ±0 | 0.11 ±0.36 |
| TBUT (s)[A] | 15.00 ±6.60 | 13.35 ±8.73 |
| McMonnies Questionnaire[A] | 7.07 ±4.57 | 9.19 ±3.76 |

A: Clinical assessments 12 months post-refractive surgery; TBUT: Tear break-up time. SD: standard deviation. S: seconds. *p-value< 0.05

Allelic frequencies of analyzed thrombospondin-1 gene (*THBS1*) polymorphisms in the study population and HapMap population.

| SNP | Allele Frequencies (%) | | | |
|---|---|---|---|---|
| | HapMap Population* | | Study Population | |
| SNP1 (rs1478604) | T | C | T | C |
| CEU | 78 | 22 | 76.2 | 23.8 |
| YRI | 20 | 80 | 21.6 | 78.4 |
| SNP2 (rs2228261) | C | T | C | T |
| CEU | 90 | 10 | 91 | 9 |
| YRI | 54 | 46 | 52.7 | 47.3 |
| SNP3 (rs2292305) | A | G | A | G |
| CEU | 90 | 10 | 90.1 | 9.9 |
| YRI | 53 | 47 | 50.8 | 49.2 |
| SNP4 (rs2228262) | A | G | A | G |
| CEU | 92 | 8 | 90.2 | 9.8 |
| YRI | 99 | 1 | 99.1 | 0.9 |

SNP: single nucleotide polymorphism. CEU = Utah residents with ancestry from northern and western Europe; YRI = African from Yoruba tribe of Ibadan, Nigeria. *JPT (Japanese in Tokyo) and CHB (Chinese in Beijing, China) populations not included as these were clustered together in study population.

Thrombospondin-1 gene (*THBS1*) polymorphism analysis in patients with post-refractive surgery dry eye

| *THBS1* polymorphism | Dominant Model | | Allele Model | |
|---|---|---|---|---|
| SNP1 | TT | CT+CC | T positive | C positive |
| No. (%) of controls (n=15) | 8 (53) | 7 (47) | 23 (76) | 7 (23) |
| No. (%) of DE patients (n=54) | 17 (31) | 37 (69) | 58 (54) | 50 (46) |
| OR (95% CI) | 2.51 (1.41 - 4.47) | | 2.83 (1.21 - 7.16) | |
| P | 0.0025* | | 0.035* | |
| SNP2 | CC | CT+TT | C positive | T positive |
| No. (%) of controls (n=16) | 12 (75) | 4 (25) | 28 (88) | 4 (13) |
| No. (%) of DE patients (n=59) | 36 (61) | 23 (39) | 90 (76) | 28 (24) |
| OR (95% CI) | 1.91 (1.05 - 3.51) | | 2.178 (0.70 - 6.74) | |
| P | 0.048* | | NS | |
| SNP3 | AA | AG+GG | A positive | G positive |
| No. (%) of controls (n=16) | 12 (75) | 4 (25) | 28 (88) | 4 (13) |
| No. (%) of DE patients (n=59) | 36 (61) | 23 (39) | 90 (76) | 28 (24) |
| OR (95% CI) | 1.92 (1.05 - 3.51) | | 2.178 (0.70 - 6.74) | |
| P | 0.048* | | NS | |
| SNP4 | AA | AG+GG | A positive | G positive |
| No. (%) of controls (n=16) | 13 (81) | 3 (19) | 29 (91) | 3 (9) |
| No. (%) of DE patients (n=59) | 48 (81) | 11 (19) | 106 (90) | 12 (10) |
| OR (95% CI) | 1.0 (0.49 - 2.03) | | 1.1 (0.29 – 4.10) | |
| P | NS (1) | | NS | |
| SNP5 | Excluded (HWE p < 0.05) | | | |

DE: dry eye; OR: odds ratio; 95% CI: 95% confidence interval; P: Fisher's exact test (p value); NS: not significant; HWE: Hardy Weinberg equilibrium *: $p < 0.05$ Haplotype frequencies of the thrombospondin-1 gene (*THBS1*) polymorphisms in patients with post-refractive surgery dry eye.

| Haplotype | Frequency | Case Frequency | Control Frequency | Chi Square | P Value |
|---|---|---|---|---|---|
| TCA | 0.59 | 0.549 | 0.742 | 3.895 | 0.0484* |
| CTG | 0.213 | 0.237 | 0.125 | 1.891 | 0.1691 |
| CCA | 0.197 | 0.214 | 0.133 | 1.05 | 0.3056 |

*: p-value<0.05

*FIG. 12*

SEQUENCE LISTING

<160> NUMBER OF SEQ ID NOS: 11

<210> SEQ ID NO 1
<211> LENGTH: 16389
<212> TYPE: DNA
<213> ORGANISM: Homo sapiens

<400> SEQUENCE: 1

| | | | | | |
|---|---|---|---|---|---|
| agccgctgcg | cccgagctgg | cctgcgagtt | cagggctcct | gtcgctctcc | aggagcaacc | 60 |
| tctactccgg | acgcacaggc | attcccgcg | cccctccagc | cctcgccgcc | ctcgccaccg | 120 |
| ctcccggccg | ccgcgctccg | gtacacacag | gtaagtcgcc | cccggcggcc | gccgaggacc | 180 |
| aaagctgccc | gggacatcca | cctggagcgc | tgaggcttca | gtccctctgg | tggaccccgg | 240 |
| aacctacact | ctccccgctc | gcctacccca | gcccgctcct | ctcagccgct | ggaggactct | 300 |
| tcagggcaag | gctccagagc | catcctctcc | agccttgagg | ttcacaaacc | aactcatcag | 360 |
| gacaccccaa | gatttcctta | ctctctgaag | tcctccttaa | gcctttgtat | cagcactcca | 420 |
| gggaagagtc | tgtacttccc | ctgccctccc | tgcaacccca | aactacagtt | cctgatcttg | 480 |
| ctcaccttcg | acttcccaaa | agcccccaaa | ttgttggtct | tgcgcccccc | acactttaaa | 540 |
| accagcatct | ctttcctcca | cctctctctc | tctctctctc | tctctctctc | atgctctctg | 600 |
| gaaagtaatc | ctgttgtcct | tcatttcagc | aaacgcgggg | tcaaagaggg | atggtcccgg | 660 |
| ccctgtcccc | atgcccagcc | ccgtttctgc | gcaccgtccc | tccctgccta | gctgatctct | 720 |
| gaccctcggc | tcttgtgctt | cctgctacag | gatccctgct | gggcaccaac | agctccacca | 780 |
| tggggctggc | ctggggacta | ggcgtcctgt | tcctgatgca | tgtgtgtggc | accaaccgca | 840 |
| ttccaggtga | gtttgtgtgg | caccttaggg | gaaggaggg | acaaggaaga | ggtgctggct | 900 |
| atcccaggtg | tgcccctca | cgtgctgtcc | tctccctctt | gagcctgact | ggacatcagg | 960 |
| acgcagcttc | actctgatcc | tggtatttat | tcacctcttt | cagtggttgc | caggagtttt | 1020 |
| caccccaacc | ctttgtctcc | accctaagg | actcagcccc | ctactgctgg | tcccagccta | 1080 |
| gaaagctcac | tttgtgttct | ctcctgtcta | acagagtctg | gcggagacaa | cagcgtgttt | 1140 |
| gacatctttg | aactcaccgg | ggccgcccgc | aagggtctg | ggcgccgact | ggtgaagggc | 1200 |
| cccgacccctt | ccagcccagc | tttccgcatc | gaggatgcca | acctgatccc | ccctgtgcct | 1260 |
| gatgacaagt | tccaagacct | ggtggatgct | gtgcgggcag | aaaagggttt | cctccttctg | 1320 |
| gcatccctga | ggcagatgaa | gaagacccgg | ggcacgctgc | tggccctgga | gcggaaagac | 1380 |
| cactctggcc | aggtcttcag | cgtggtgtcc | aatggcaagg | cgggcacccct | ggacctcagc | 1440 |
| ctgaccgtcc | aaggaaagca | gcacgtggtg | tctgtggaag | aagctctcct | ggcaaccggc | 1500 |
| cagtggaaga | gcatcaccct | gtttgtgcag | gaagacaggg | cccagctgta | catcgactgt | 1560 |
| gaaaagatgg | agaatgctga | gttggacgtc | cccatccaaa | gcgtcttcac | cagagacctg | 1620 |
| gccagcatcg | ccagactccg | catcgcaaag | gggggcgtca | atgacaattt | ccaggtgagg | 1680 |
| cttcttctct | gagccctgct | ccgtgggatc | atctgctaga | caggtgacct | gccaggaggg | 1740 |
| ctacaggaaa | tcctgtctgt | aaactaacgc | agcagttctc | agattttagg | cagcatgagc | 1800 |
| atcacctgga | gggcttgtga | agctcaccc | tgctgcaccc | cagccccaga | gtctgggatt | 1860 |
| ctgtaaaact | gcaactctaa | caagtaccag | gtgatgctga | tgccggtggt | ctgggaagca | 1920 |
| cactttgaaa | actactcaag | gaaacaagaa | atggttttcc | tttagcagtc | agcctgttca | 1980 |
| agccttagat | actccttagg | ctcttaagaa | aagagcttat | ttcaaatgca | ttcccccaat | 2040 |
| tttaatcttg | tttgaaatgg | atactttcta | tgggcagaat | cagtaccact | ttgctattgg | 2100 |

```
attcctcatg gggatgcagc tggtctcaca taaaaggtta aaatagcagt tagttgttgc    2160
tgttacagct tcatctgtgc cttaacttct agatctttgc aacggtggct ttgaactccc    2220
acatttaact ctttgacact ggaaagtgtc attatatcct ctaggcttag gatcagattc    2280
catttcctgt gtacccaagt aggctgataa ctgaattctt tgtaaaatac tcaagacttg    2340
gcagaagtca caattaagat tttgaagttg tttggcgatt aatgttgctg tgttattttg    2400
acatagtgat cttaagacag ctctttgaag cttttagaac atctattgta tgcttttcct    2460
agcatacaga cagtctcccc caaccccatc cccaccccgc tctgcattct acaagtaatg    2520
tgtgtcctct gcccacaggg ggtgctgcag aatgtgaggt ttgtctttgg aaccacacca    2580
gaagacatcc tcaggaacaa aggctgctcc agctgtgagt acccctctat ttttagggca    2640
catagggaat caggggggaat tccaccaaaa acaaactgag gaatttagca atagtggtta    2700
tacataaatt accccccagtg agatcatcaa gaggcataca gaagtgactc caaggggtat    2760
tatacacaca cacgtataca cacgtgcgca tacacgcaac ccctctacct gcatccttca    2820
caccaaatga aacgtcttct accactaaga actcaagagg ctggttggta agagtatcta    2880
tttgaagttt tcattttgtt tcttgccagc taccagtgtc ctcctcaccc ttgacaacaa    2940
cgtggtgaat ggttccagcc ctgccatccg cactaactac attggccaca agacaaagga    3000
cttgcaagcc atctgcggca tctcctgtga tgagctgtcc agcatggtcc tggaactcag    3060
gggcctgcgc accattgtga ccacgctgca ggacagcatc cgcaaagtgg tcagtggcct    3120
ctgcacccag cccgttagca tgaaccctgg aaggtttatc gcagatggtc ccaaatgact    3180
gaaaatgcgg ggggacacta atgatattct ctcccattta gactgaagag aacaaagagt    3240
tggccaatga gctgaggcgg cctcccctat gctatcacaa cggagttcag tacagaaata    3300
acgaggaatg gactgttgat agctgcactg agtgtcactg tcaggtaagg gaccttcacc    3360
agccagaata agaatcgacg gcttttgttt gaacctacat cttttgggaa atacccctaat    3420 cgccacagag attctttta tgttccatgg cctgataaca aagtgttttt ttttctttta    3480
agatgcaatt atggcatcta taagttcttc tttaaactct cagatggttt atcaaagtat    3540
taattatacc ccaggctaag tatctaagag aatgaatcta ctaagacatc tgaataattt    3600 acctaccttta gttcaaagac taagtgttga atgtcaggta aataaaacct ggttggaaca    3660 ttcattttt tttcccaacc ctgatttata ttcagctttg gcataggttc ttttagtaca    3720
gtagcaattg ttttttcaaat cacttagtct gacactgtta ggatgttact gtctgctttg    3780
ctcagatggc actgccaggt gtgtgattca ctctagcatc cccgcatgcc agtggccagt    3840
gagtttggag gttcacctgg cttatctatt aatagcaaag tatttgaatt tgcttaaata    3900
caaatcacag atgactggct gtgggaacca acttcattaa attcccttc ttttccaata    3960 taaagacaga tcacagatct atagatgagg aaaagtgct tatagatctt ccttcctccc    4020
cccaaacaca taatataaaa atgtaaaagt cctggctgaa ttttctgagt ttgattcag    4080 acatagattt gacccatgat gtttgttggt tcctctgcta taaattcttt gtactgtaac    4140
ttccacccct tgactaagtag caattaaaaa gaacttttcca aggaatggag tgacacgtaa    4200
actagcacta gaactgtctc tacgatagtg gtggctgcaa atatgacaga gacagatcta    4260
tgaaaatcat tccactagag cattgacagc cctgaccatg tttttggcttg taaaggaaat    4320 gttacaggat gtagacttct gtatgcaaca tgctcagcag cctgttcccc tctcactctc    4380
ttgccctgca gaactcagtt accatctgca aaaaggtgtc ctgccccatc atgccctgct    4440
ccaatgccac agttcctgat ggagaatgct gtcctcgctg ttggcgtaag tttctcaaat    4500
```

```
ggcatagcta ttcttcagtg actaggtcag ttctacatac atcctagaca gccgagcaca    4560
acactggaac cccacccca tctccatcat gcttccattc agtttcttgc tgcagcagct     4620
ggttaactga cagcttatct gctgtacaga gccaaaactc cattatgagt acatcgtaat    4680
tacccatctg gattgcagta atggcagtga agatcttggt atagctcatt aattctgatt    4740
ttttgctttg aggaaaagag atgaagacgt ggcagcaaca gctctaagtt gactgctttt    4800
agaatttgac cttagtggca cagagttaag aaaaatctgc tcaccagaga tattgacagg    4860
cttactgtgt aagcattggc ctgatcgggc ctggaagttt tgccccttc atctgtaggg     4920 ataagagggc ctaagagaat agcagcaatc tgagctctag agcaccaaaa gaaataaggc    4980
acgatatcgt tccatggcac gttatccctg gcttttgtta ccagtaaaat gaatgacttt    5040
gctgagacaa tacttagtgt agcaggtaca agttataaaa gtgattcatt acaactaaga    5100
taaggaagaa aacaggaaaa cagcacttgc ccttcacaca cacagaaaca cacatgcaca    5160
cacacacaaa cacacccttg tcacagctca gaataaccaa ttccatccag ggatcatatt    5220
agcgatattg gcactgtaat ggtcgttttt acatttattt tctgttccgc attcacttaa    5280
catgtgcgtt aaaaggaaca aagctagctg gaggtagcaa agttttgaac ttgaatcagg    5340
gattgctaag aaaacttaca actaatgacc acagaaagta agttctttgt cttctgtctg    5400
atacagctag atgtgattgt agccgtggtg cctgggcaga tggtaaacaa acatgctgtc    5460
ctcttatgac aatatgtgca gagaaggccc caaacgctgg ggtgagagga caacaaact     5520 gactaactca cggccgagtt ggagccagaa ccaacaacag ctcggctgcc ttcacactca    5580
tctgtcaaac acatggtgta tggctcccct gacagaaatg actcctataa gcttcctcat    5640
actcgcgcat tcttggaagt ctgagactgg aaatgcctac ccagatatgt taagtcagta    5700
aaggaaaact catttgcaat gctgagagga gaaagaaaat caatgaatag gagagcatac    5760
actgtgggaa ggctcagctg tactgagcca ggcaaagcat ccgattaccc cactgctgta    5820
cacatcatga cctgggataa acccctgggc cgttggccta agaaatatgt tgcttttcat    5880
cctgtataac tgcaactttg tgccggctca tattatgttc tagagagctc atgtacacca    5940
tggtgaccat agttaataat actggattgt atgcttaaaa tttgctaaga gagtagatct    6000
taagtcatca ccaaaaaaag taactgtaag atgatggaga tgtgttaatt agcttgacgg    6060
tggtaatcac aatatatgtg tatatcaaaa catcacatta tacaccttaa atgtatataa    6120
tatttgtcaa ttatacctca gtaaagccaa aaagaaataa atatattgct tttcacccct    6180
tggcaagtgg agggccctga acagagccct ctaaagaaca gcttgtccta atcatcacgt    6240
acctgatgaa cctctgtttc ccctgcagcc agcgactctg cggacgatgg ctggtctcca    6300
tggtccgagt ggacctcctg ttctacgagc tgtggcaatg gaattcagca gcgcggccgc    6360
tcctgcgata gcctcaacaa ccgatgtgag ggctcctcgg tccagacacg gacctgccac    6420
attcaggagt gtgacaagag atgtaagcat cttagcctct cagggacgtg gagaactgac    6480
ctgtccttgt tgtcgtcacc aagggcagct ccacagcatg tatattaaga acacgggttc    6540
taggatctct ggatcccaat cccactgctt agctgtgcac ccttgaacac aacttaccct    6600
ctctgaggct ctttcctcat ttgcaacttg gagataataa tagttcttga taagtttatc    6660
ttgagcattt tatttagata ctgcatgtaa agcagttagc actgagtttt ggtttatggt    6720
aagcaccctg taaatgttag gatattaaca gcaacccata aaaacagcga acttatccgt    6780
tctctggtag aaaacattcc atgttgcat ttgggcatgt ggccaggagc caatttctac     6840
cgtacactgg gtttagttgc cattgaccat ttcctggaaa tacttctgcg tgctcctgat    6900
```

```
gggagcctct atttggctgt ctctaagcca aaaccatttg tgaccatcaa ctctgtactt    6960
tagttaaaca ggatggtggc tggagccact ggtccccgtg gtcatcttgt tctgtgacat    7020
gtggtgatgg tgtgatcaca aggatccggc tctgcaactc tcccagcccc cagatgaacg    7080
ggaaaccctg tgaaggcgaa gcgcgggaga ccaaagcctg caagaaagac gcctgcccca    7140
gtaagtgtga ggtccgctgc aagggtgagc atgggcagca gctctgccca gctggttgcc    7200
tggcatctgc agcctgcagt tcagtgggtc atagagcagg aaggttacct actagagaaa    7260
caaacagaag caaagtcctg caggctcagc aacttctttt aatgaaaaac aaactcaccc    7320
tcttccccag cattctttcc atgtgtcaga gaagcagagg tttcttgaac gggcttagga    7380
gagtctatga caagggaggg atttgaaagt tgatcttaat tgttgcctgt ggttcatctt    7440
cttacagtca atggaggctg gggtccttgg tcaccatggg acatctgttc tgtcacctgt    7500
ggaggagggg tacagaaacg tagtcgtctc tgcaacaacc ccacacccca gtttggaggc    7560
aaggactgcg ttggtgatgt aacagaaaac cagatctgca acaagcagga ctgtccaatt    7620
ggtgagccac gcagcccagg atgaaacgac ccaggagctt tgctctttta ctgaatgctg    7680
cagtcagcat tcgaggagat tccagcttgg ttagtcctga gcgatttgat tgctctaaga    7740
tgcaggtgga caacataatc ccaacaagtt atcggttccc tatacccctat aatatcttac    7800 actgtgttaa gtcccagca tggcagtatg gcagcttaga ccaaccattt actgtgactg    7860
tctctctctc cttgtctcag atggatgcct gtccaatccc tgctttgccg gcgtgaagtg    7920
tactagctac cctgatggca gctggaaatg tggtgcttgt cccctggtt acagtggaaa    7980 tggcatccag tgcacagatg ttgatgaggt gaggaactga tggggctccg agtttctgga    8040
tctaggaaag cagctaacct gtgcagtcgc ttccttatgg cagtgacttc taaacatgat    8100
gcacgctctt atttcctcca tagtgcaaag aagtgcctga tgcctgcttc aaccacaatg    8160
gagagcaccg gtgtgagaac acggaccccg gctacaactg cctgccctgc cccccacgct    8220
tcaccggctc acagcccttc ggccagggtg tcgaacatgc cacggccaac aaacaggtac    8280
agtcaactag acgagtaaac cagaggacag gagagctgtc cttgaccaaa ataactggga    8340
gcgggaggaa tgtaatttca tacccttcac caaaaaaaaa agggcgagga gatgaatgta    8400
cggtctagtt ttagaaacgt gattagaaaa tccatggtaa atcctgcagg ggaaaaacag    8460
tcttccatat ttaaaaatgc tgctctggaa taagttgtga gcagatggac ttgtaaacgc    8520
ctaggtgctg agcaaattca agaaaaataa acataaagca aagtttgctt atagcctcag    8580
ggagaatggg gagggacaga ggtaacccac actcttccaa atggagcctc tgtctactca    8640
gagatgacag ggatctggat tcttgtttcc atgatatctg aggattctca aaagctctgt    8700
gtaacagcag catggtgtac cctcaggtgt gcaagcccg taaccctgc acggatggga    8760 cccacgactg caacaagaac gccaagtgca actacctggg ccactatagc gaccccatgt    8820
accgctgcga gtgcaagcct ggctacgctg gcaatggcat catctgcggg gaggacacag    8880
acctggatgg ctggcccaat gagaacctgg tgtgcgtggc caatgcgact taccactgca    8940
aaaaggtaga gccaggtcct ttgtgtgcct ccagaaagag ggcccatcac cttatcaaaa    9000
cacaggctaa ggaattttaa atacttaaag tttggacatg aaactgaaag attaaatctc    9060
ccaaagggag aggggcacta attcctatta aaattaaatc acttggtgcc aaaaacatga    9120
acagggctag ctcttttggg gcaactgtgt tccatagtca actcttctgt ccaaaaaaaa    9180
gttcagtact ctatccaaat accagcaaag catgacttgt gttcacaaca tctataaagc    9240
ctagagcatt tacacaaatt ctgtatgtat atcccccaag aaaagtttta ttttcttgtc    9300
```

```
ttcccataaa aaaaatatgc tgttactgag ccaaattctg ttcttttct atttggaatt    9360 ccaggtacac tccctcgtgc atgagctcag catgaggaag gcaactgaag cagtgatata    9420
tatcttctct ttcctaggat aattgcccca accttcccaa ctcagggcag gaagactatg    9480
acaaggatgg aattggtgat gcctgtgatg atgacgatga caatgataaa attccagatg    9540
acagggtaaa aacagttttc tatccctttt tcatcttttc agttcagcaa cagcctgaaa    9600
cactttggga ttcaaggaaa ttacatggct atagcaaaaa atataccaaa tcaatacaca    9660
ggataattag aaattattca ttgtgttcca gtagtttaag gatgtagatg ttgccaagag    9720
aatttttaaa tgagggtttt gttttcatc agaactgttt ttctctgtac ttgagaaatt    9780
ataatgcata aacaaatgcc actttgttcc ctagattcat ttcaaatgtc acatcgaaat    9840
tacagtaaaa ttgactttgg gcacactatg aactgagatg atgggattat attctacatc    9900
tcactaactt ctaacccaca gggatccatt tttttaacta tgtcctttta acttttgtag    9960
tgatcgtttt acactgagtg atcaattagc ctatccacta ggtagaaagt attgctgatt   10020
ttcacagttt tagacatatt atgcacatgg tttgaggctt gagctgtttt caaggacaac   10080
attgttaagt gctccatttc ttctctttgc aggacaactg tccattccat tacaacccag   10140
ctcagtatga ctatgacaga gatgatgtgg gagaccgctg tgacaactgt ccctacaacc   10200
acaacccaga tcaggcagac acagacaaca atggggaagg agacgcctgt gctgcagaca   10260
ttgatggaga cggtaaggtg ctgcctgatc agagggcccg cggagacag ggacatgcac   10320 agctttccaa acgtacttct gtctagtcct ggctattagt atgcactttg gtggaaacat   10380
ccaaggctgg agagcccagc tcttatttgt cccttgttct cttcaggtat cctcaatgaa   10440
cgggacaact gccagtacgt ctacaatgtg gaccagagag acactgatat ggatggggtt   10500
ggagatcagt gtgacaattg ccccttggaa cacaatccgg atcaggtagg tggatggact   10560
cctttcagag tctttcagta aactgttgga atatcccttt catggccttt gaaaatgag   10620 cttaacaaag ttcaaacact ttcattactg tggctccctg gcttctcata gccaactgga   10680
atacgttcat gtaaataatt tgcctgatgt gagctccttg cacagagtct cacagatctt   10740
tagcatgaag atctggtaac ttcagtctta ccttctgtaa gaagggctac tggacttgct   10800
cagcatcgtc taccattgtt aagacaaatt atacaaagca gacatctgtg actgacaact   10860
gtacaataat attaatcata tgtaatacta agagatggaa aaataaatgt gcataagcaa   10920
aataaccatt ttcatggcta atgatgtaat ctagctataa gaaaatcatc aaactaagga   10980
tacatccaaa accaaagtaa tttatccctg tcataaacat tacccagaca gtatacaaca   11040
cagggaccag tggtctgttt ccatcttttc aggacttttc agagaagtcg acgtgtcaac   11100
agttttacaa ctgaaacctt ctaaggaaat tctctgttat aaagtatcca gaaaatttca   11160
tttaacatta agatgtaaac agttaacatt tcatttcatc tttagtaatt aaatatcact   11220
ctatttgacc ttatttagaa agtttttatat gtaaaacatt tttaaattat cccttctcag   11280 attttatac gaaaacaaag ataaaggaaa aaaacttta aaatgtaatt gctactattg   11340 ctatcttct gcaggagtgt gtaaatagac atgacacccc actggctgta tcaaacaatg   11400
gagaattttc cctgtggtgg gggcataagt tatcttaac atgaatggtt tatactgcaa   11460
tttaccctcc atttacatct ctctttcagc tggactctga ctcagaccgc attggagata   11520
cctgtgacaa caatcaggat attgatgaag atggccacca gaacaatctg gacaactgtc   11580
cctatgtgcc caatgccaac caggctgacc atgcaaagga tggcaaggga gatgcctgtg   11640
accacgatga tgacaacgat ggcattcctg atgacaagga caactgcaga ctcgtgccca   11700
```

```
atcccgacca gaaggactct gacggtgagt catgggagcc actttctaag acagggactg   11760
ctggcacagc tgtgtagatt gaagaaatga aaccaaggct caaagcattt gacaggatga   11820
agggaccaaa tgccaactta gacaagatag tgacatttct gacaccagta ataataatag   11880
cactttagaa ttttgctgaa ctcttgcttt tttgacctca ggcgatggtc gaggtgatgc   11940
ctgcaaagat gattttgacc atgacagtgt gccagacatc gatgacatct gtcctgagaa   12000
tgttgacatc agtgagaccg atttccgccg attccagatg attcctctgg accccaaagg   12060
gacatcccaa aatgacccta ctgggttgt acgccatcag ggtaaagaac tcgtccagac   12120
tgtcaactgt gatcctggac tcgctgtagg tgagtagcga gttcttagat cctaagagac   12180
tgatgcatac atggggaaaa acaaatataa aacctggcag ttgtacctat ccctgtgggt   12240
gctgaggatg tctaggaaca tgatggagaa ccttctgaag gctgcaggtt ttaacctggc   12300
tctgggctct tcttccaggt tatgatgagt ttaatgctgt ggacttcagt ggcaccttct   12360
tcatcaacac cgaaagggac gatgactatg ctggatttgt ctttggctac cagtccagca   12420
gccgctttta tgttgtgatg tggaagcaag tcacccagtc ctactgggac accaacccca   12480
cgagggctca gggatactcg ggcctttctg tgaaagttgt aaactccacc acagggcctg   12540
gcgagcacct gcggaacgcc ctgtggcaca caggaaacac ccctggccag gtaagaagca   12600
aagccctgga acagagagag agcttatggg tgcctgacta gcactgggga tgctgtgctt   12660
tgaccaagac tctgaccagg gagtcttaga aagttcccag catcaccagc tgcagcattg   12720
aactctgctt tgtaaaaaca taatagtgtt gaaagggag cttgaccaag aattgccctg   12780
caaatcctaa ggtgccttca gccttttcaa acaaaaaaac ctccttccct cctctctgtc   12840
tgctttatat gtgtgctcag tggcacacaa caaatatgag aggacttgga aaaattcccc   12900
attgcagccc tctaacttag atcagctcag tacctttcaa gcattgtttc tgatggaatg   12960
aaatagaaat ctttacctga aggagctgtg tttcaacctt tccttttcct tttccttcag   13020
gtgcgcaccc tgtggcatga ccctcgtcac ataggctgga aagatttcac cgcctacaga   13080
tggcgtctca gccacaggcc aaagacgggt tcattaggt acgatcatac tgattcactt   13140
tcacttacag tcacactgag ggacaaaaag acaaaaagta ttaaatagca ttgtcactaa   13200
acaagatttt ttttccctgc agagtggtga tgtatgaagg gaagaaaatc atggctgact   13260
caggacccat ctatgataaa acctatgctg gtggtagact agggttgttt gtcttctctc   13320
aagaaatggt gttcttctct gacctgaaat acgaatgtag aggtaagagc aacatcacca   13380
tgaatgtaca ctggacatct ctatttcaga ctaaatcaa ggatgacggt tatgggggag   13440
tccagtgtaa agactgtttt ggagacaggg ttatttctat tttgcttttg aggacacaag   13500
gacaaaaatg gaataatgcc taggcactgt ggcttatgag ttcctgagtc cttagctata   13560
atattagttt gcttagcaat ctctgtgctc ctcatacaca gtgcaaaggt aagctgcaga   13620
aaagctccta tataatttgg acttcattaa taatactgtt ctttacaatt atatatttat   13680
atatcttact gcttattgtt ttatgcatgc catcacagca cgagttagca ttcccaactt   13740
ttccctgtat acaaagaagg gagaggaatg ttgctttcat attggcatgt taaattaatg   13800
ttcactatta aacttagcat ttttttttcct cattcttttt tacttagtca ttacttaagc   13860
tcgctgagtc caacactggc tctaccacaa aataagtgct taatatatat ttactgggcc   13920
aaggccagat acctaaaaga tcaatgacag tagagaaaga tggttgattt tactcaaaaa   13980
aatctaaatt attaatgtaa ttttgagtc caaatttta aaataagact ccctaaactg   14040
ttaacattga aagcctttgg aaagcataat atatgttctg gaaggttcac gctgtgtcgg   14100
```

```
tctcctagca tcaatgtcag ctaataaaat taaatgctaa tgtgcttgaa caaccttaaa   14160
attaggcttt tgtcattaga aaagtagagc tattcctatg tggttaactt attaactaag   14220
atgtctatgc ttttatgaat tagttttcat ttgtatattt atttatattt gtttatttaa   14280
cagatcccta atcatcaaat tgttgattga aagactgatc ataaaccaat gctggtattg   14340
caccttctgg aactatgggc ttgagaaaac ccccaggatc acttctcctt ggcttccttc   14400
ttttctgtgc ttgcatcagt gtggactcct agaacgtgcg acctgcctca agaaaatgca   14460
gttttcaaaa acagactcag cattcagcct ccaatgaata agacatcttc caagcatata   14520
aacaattgct ttggtttcct tttgaaaaag catctacttg cttcagttgg aaggtgccc    14580 attccactct gcctttgtca cagagcaggg tgctattgtg aggccatctc tgagcagtgg   14640
actcaaaagc attttcaggc atgtcagaga agggaggact cactagaatt agcaaacaaa   14700
accaccctga catcctcctt caggaacacg gggagcagag gccaaagcac taaggggagg   14760
gcgcataccc gagacgattg tatgaagaaa atatggagga actgttacat gttcggtact   14820
aagtcatttt caggggattg aaagactatt gctggatttc atgatgctga ctggcgttag   14880
ctgattaacc catgtaaata ggcacttaaa tagaagcagg aaagggagac aaagactggc   14940
ttctggactt cctccctgat ccccacccctt actcatcacc tgcagtggcc agaattaggg   15000
aatcagaatc aaaccagtgt aaggcagtgc tggctgccat tgcctggtca cattgaaatt   15060
ggtggcttca ttctagatgt agcttgtgca gatgtagcag gaaaatagga aaacctacca   15120
tctcagtgag caccagctgc ctcccaaagg aggggcagcc gtgcttatat ttttatggtt   15180
acaatggcac aaaattatta tcaacctaac taaaacattc cttttctctt ttttcctgaa   15240
ttatcatgga gttttctaat tctctctttt ggaatgtaga ttttttttaa atgctttacg   15300
atgtaaaata tttatttttt acttattctg gaagatctgg ctgaaggatt attcatggaa   15360
caggaagaag cgtaaagact atccatgtca tctttgttga gagtcttcgt gactgtaaga   15420
ttgtaaatac agattatta ttaactctgt tctgcctgga aatttaggct tcatacggaa   15480
agtgtttgag agcaagtagt tgacatttat cagcaaatct cttgcaagaa cagcacaagg   15540
aaaatcagtc taataagctg ctctgcccct tgtgctcaga gtggatgtta tgggattctt   15600
tttttctctg ttttatcttt tcaagtggaa ttagttggtt atccatttgc aaatgtttta   15660
aattgcaaag aaagccatga ggtcttcaat actgttttac cccatccctt gtgcatattt   15720
ccagggagaa ggaaagcata tacacttttt tctttcattt ttccaaaaga gaaaaaaatg   15780
acaaaaggtg aaacttacat acaaatatta cctcatttgt tgtgtgactg agtaaagaat   15840
ttttggatca agcggaaaga gtttaagtgt ctaacaaact taaagctact gtagtaccta   15900
aaaagtcagt gttgtacata gcataaaaac tctgcagaga agtattccca ataaggaaat   15960
agcattgaaa tgttaaatac aatttctgaa agttatgttt ttttctatc atctggtata   16020 ccattgcttt atttttataa attattttct cattgccatt ggaatagata tctcagattg   16080
tgtagatatg ctatttaaat aatttatcag gaaatactgc ctgtagagtt agtatttcta   16140 ttttttatata atgtttgcac actgaattga agaattgttg gtttttcttt ttttttgttt   16200 tgttttttttt tttttttttt tttgcttttg acctcccatt tttactattt gccaatacct   16260
ttttctagga atgtgctttt ttttgtacac atttttatcc attttacatt ctaaagcagt   16320
gtaagttgta tattactgtt tcttatgtac aaggaacaac aataaatcat atggaaattt   16380
atatttata                                                           16389
```

```
<210> SEQ ID NO 2
<211> LENGTH: 1170
<212> TYPE: PRT
<213> ORGANISM: Homo sapiens

<400> SEQUENCE: 2

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
            20                  25                  30

Ile Phe Glu Leu Thr Gly Ala Ala Arg Lys Gly Ser Gly Arg Arg Leu
        35                  40                  45

Val Lys Gly Pro Asp Pro Ser Ser Pro Ala Phe Arg Ile Glu Asp Ala
    50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
            100                 105                 110

Ser Gly Gln Val Phe Ser Val Val Ser Asn Gly Lys Ala Gly Thr Leu
        115                 120                 125

Asp Leu Ser Leu Thr Val Gln Gly Lys Gln His Val Val Ser Val Glu
    130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
            180                 185                 190

Ser Ile Ala Arg Leu Arg Ile Ala Lys Gly Gly Val Asn Asp Asn Phe
        195                 200                 205

Gln Gly Val Leu Gln Asn Val Arg Phe Val Phe Gly Thr Thr Pro Glu
    210                 215                 220

Asp Ile Leu Arg Asn Lys Gly Cys Ser Ser Ser Thr Ser Val Leu Leu
225                 230                 235                 240

Thr Leu Asp Asn Asn Val Val Asn Gly Ser Ser Pro Ala Ile Arg Thr
                245                 250                 255

Asn Tyr Ile Gly His Lys Thr Lys Asp Leu Gln Ala Ile Cys Gly Ile
            260                 265                 270

Ser Cys Asp Glu Leu Ser Ser Met Val Leu Glu Leu Arg Gly Leu Arg
        275                 280                 285

Thr Ile Val Thr Thr Leu Gln Asp Ser Ile Arg Lys Val Thr Glu Glu
    290                 295                 300

Asn Lys Glu Leu Ala Asn Glu Leu Arg Arg Pro Pro Leu Cys Tyr His
305                 310                 315                 320

Asn Gly Val Gln Tyr Arg Asn Asn Glu Glu Trp Thr Val Asp Ser Cys
                325                 330                 335

Thr Glu Cys His Cys Gln Asn Ser Val Thr Ile Cys Lys Lys Val Ser
            340                 345                 350

Cys Pro Ile Met Pro Cys Ser Asn Ala Thr Val Pro Asp Gly Glu Cys
        355                 360                 365

Cys Pro Arg Cys Trp Pro Ser Asp Ser Ala Asp Asp Gly Trp Ser Pro
    370                 375                 380
```

-continued

```
Trp Ser Glu Trp Thr Ser Cys Ser Thr Ser Cys Gly Asn Gly Ile Gln
385                 390                 395                 400

Gln Arg Gly Arg Ser Cys Asp Ser Leu Asn Asn Arg Cys Glu Gly Ser
        405                 410                 415

Ser Val Gln Thr Arg Thr Cys His Ile Gln Glu Cys Asp Lys Arg Phe
            420                 425                 430

Lys Gln Asp Gly Gly Trp Ser His Trp Ser Pro Trp Ser Ser Cys Ser
        435                 440                 445

Val Thr Cys Gly Asp Gly Val Ile Thr Arg Ile Arg Leu Cys Asn Ser
    450                 455                 460

Pro Ser Pro Gln Met Asn Gly Lys Pro Cys Glu Gly Glu Ala Arg Glu
465                 470                 475                 480

Thr Lys Ala Cys Lys Lys Asp Ala Cys Pro Ile Asn Gly Gly Trp Gly
            485                 490                 495

Pro Trp Ser Pro Trp Asp Ile Cys Ser Val Thr Cys Gly Gly Gly Val
        500                 505                 510

Gln Lys Arg Ser Arg Leu Cys Asn Asn Pro Thr Pro Gln Phe Gly Gly
    515                 520                 525

Lys Asp Cys Val Gly Asp Val Thr Glu Asn Gln Ile Cys Asn Lys Gln
530                 535                 540

Asp Cys Pro Ile Asp Gly Cys Leu Ser Asn Pro Cys Phe Ala Gly Val
545                 550                 555                 560

Lys Cys Thr Ser Tyr Pro Asp Gly Ser Trp Lys Cys Gly Ala Cys Pro
            565                 570                 575

Pro Gly Tyr Ser Gly Asn Gly Ile Gln Cys Thr Asp Val Asp Glu Cys
        580                 585                 590

Lys Glu Val Pro Asp Ala Cys Phe Asn His Asn Gly Glu His Arg Cys
    595                 600                 605

Glu Asn Thr Asp Pro Gly Tyr Asn Cys Leu Pro Cys Pro Pro Arg Phe
610                 615                 620

Thr Gly Ser Gln Pro Phe Gly Gln Gly Val Glu His Ala Thr Ala Asn
625                 630                 635                 640

Lys Gln Val Cys Lys Pro Arg Asn Pro Cys Thr Asp Gly Thr His Asp
            645                 650                 655

Cys Asn Lys Asn Ala Lys Cys Asn Tyr Leu Gly His Tyr Ser Asp Pro
        660                 665                 670

Met Tyr Arg Cys Glu Cys Lys Pro Gly Tyr Ala Gly Asn Gly Ile Ile
    675                 680                 685

Cys Gly Glu Asp Thr Asp Leu Asp Gly Trp Pro Asn Glu Asn Leu Val
690                 695                 700

Cys Val Ala Asn Ala Thr Tyr His Cys Lys Lys Asp Asn Cys Pro Asn
705                 710                 715                 720

Leu Pro Asn Ser Gly Gln Glu Asp Tyr Asp Lys Asp Gly Ile Gly Asp
            725                 730                 735

Ala Cys Asp Asp Asp Asp Asp Asn Asp Lys Ile Pro Asp Asp Arg Asp
        740                 745                 750

Asn Cys Pro Phe His Tyr Asn Pro Ala Gln Tyr Asp Tyr Asp Arg Asp
    755                 760                 765

Asp Val Gly Asp Arg Cys Asp Asn Cys Pro Tyr Asn His Asn Pro Asp
770                 775                 780

Gln Ala Asp Thr Asp Asn Asn Gly Glu Gly Asp Ala Cys Ala Ala Asp
785                 790                 795                 800
```

```
Ile Asp Gly Asp Gly Ile Leu Asn Glu Arg Asp Asn Cys Gln Tyr Val
            805                 810                 815

Tyr Asn Val Asp Gln Arg Asp Thr Asp Met Asp Gly Val Gly Asp Gln
        820                 825                 830

Cys Asp Asn Cys Pro Leu Glu His Asn Pro Asp Gln Leu Asp Ser Asp
        835                 840                 845

Ser Asp Arg Ile Gly Asp Thr Cys Asp Asn Asn Gln Asp Ile Asp Glu
850                 855                 860

Asp Gly His Gln Asn Asn Leu Asp Asn Cys Pro Tyr Val Pro Asn Ala
865                 870                 875                 880

Asn Gln Ala Asp His Asp Lys Asp Gly Lys Gly Asp Ala Cys Asp His
            885                 890                 895

Asp Asp Asp Asn Asp Gly Ile Pro Asp Lys Asp Asn Cys Arg Leu
        900                 905                 910

Val Pro Asn Pro Asp Gln Lys Asp Ser Asp Gly Asp Gly Arg Gly Asp
        915                 920                 925

Ala Cys Lys Asp Asp Phe Asp His Asp Ser Val Pro Asp Ile Asp Asp
        930                 935                 940

Ile Cys Pro Glu Asn Val Asp Ile Ser Glu Thr Asp Phe Arg Arg Phe
945                 950                 955                 960

Gln Met Ile Pro Leu Asp Pro Lys Gly Thr Ser Gln Asn Asp Pro Asn
            965                 970                 975

Trp Val Val Arg His Gln Gly Lys Glu Leu Val Gln Thr Val Asn Cys
            980                 985                 990

Asp Pro Gly Leu Ala Val Gly Tyr Asp Glu Phe Asn Ala Val Asp Phe
        995                 1000                1005

Ser Gly Thr Phe Phe Ile Asn Thr Glu Arg Asp Asp Asp Tyr Ala
        1010                1015                1020

Gly Phe Val Phe Gly Tyr Gln Ser Ser Ser Arg Phe Tyr Val Val
        1025                1030                1035

Met Trp Lys Gln Val Thr Gln Ser Tyr Trp Asp Thr Asn Pro Thr
        1040                1045                1050

Arg Ala Gln Gly Tyr Ser Gly Leu Ser Val Lys Val Val Asn Ser
        1055                1060                1065

Thr Thr Gly Pro Gly Glu His Leu Arg Asn Ala Leu Trp His Thr
        1070                1075                1080

Gly Asn Thr Pro Gly Gln Val Arg Thr Leu Trp His Asp Pro Arg
        1085                1090                1095

His Ile Gly Trp Lys Asp Phe Thr Ala Tyr Arg Trp Arg Leu Ser
        1100                1105                1110

His Arg Pro Lys Thr Gly Phe Ile Arg Val Val Met Tyr Glu Gly
        1115                1120                1125

Lys Lys Ile Met Ala Asp Ser Gly Pro Ile Tyr Asp Lys Thr Tyr
        1130                1135                1140

Ala Gly Gly Arg Leu Gly Leu Phe Val Phe Ser Gln Glu Met Val
        1145                1150                1155

Phe Phe Ser Asp Leu Lys Tyr Glu Cys Arg Asp Pro
        1160                1165                1170

<210> SEQ ID NO 3
<211> LENGTH: 1001
<212> TYPE: DNA
<213> ORGANISM: Homo sapiens
```

<400> SEQUENCE: 3

```
gttttaaagt gtgggggggcg caagaccaac aatttggggg cttttgggaa gtcgaaggtg      60
agcaagatca ggaactgtag tttggggttg cagggagggc aggggaagta cagactcttc     120
cctggagtgc tgatacaaag gcttaaggag gacttcagag agtaaggaaa tcttggggtg     180
tcctgatgag ttggtttgtg aacctcaagg ctggagagga tggctctgga gccttgccct     240
gaagagtcct ccagcggctg agaggagcgg gctggggtag gcgagcgggg agagtgtagg     300
ttccggggtc caccagaggg actgaagcct cagcgctcca ggtggatgtc ccgggcagct     360
ttggtcctcg gcggccgccg ggggcgactt acctgtgtgt accggagcgc ggcggccggg     420
agcggtggcg agggcggcga gggctggagg ggcgcgggga atgcctgtgc gtccggagta     480
gaggttgctc ctggagagcg rcaggagccc tgaactcgca ggccagctcg ggcgcagcgg     540
ctggcaaggc ggaggagccg cgcgcttta aagggcgct cgcattcctg gggattcctc     600
cggccaatgg gcggcggccg ggcaggaagc gggaggtggg ggccagtctg ggctcctctc     660
tccgccccc gctgcctggc gcgcaacttt ccagctagaa agtgaagggg gcggggtcg     720
gggcttggga gcactagaac ttctcagaaa agtcggtgcc cgcccacgca gccttggcgc     780
gcacgggctc ggcgctcgta ctcttgcgcc acgcgggctc ggggtgatca gcaagcatcc     840
cgaaaaggga cggggctggg gagaccacct aggagggccc gcggggtggc gcagggctt     900
tcgggcgagc tgatctcccg gaatgcctgg ttgatggcga gaggtggata ctagagactg     960
ggcccgtttt gtaaaaagaa aaatgggccg acggggcgca g                        1001
```

<210> SEQ ID NO 4
<211> LENGTH: 1001
<212> TYPE: DNA
<213> ORGANISM: Homo sapiens

<400> SEQUENCE: 4

```
acccttgaac acaacttacc ctctctgagg ctctttcctc atttgcaact tggagataat      60
aatagttctt gataagttta tcttgagcat tttatttaga tactgcatgt aaagcagtta     120
gcactgagtt ttggttttatg gtaagcaccc tgtaaatgtt aggatattaa cagcaaccca     180
taaaaacagc gaacttatcc gttctctggt agaaaacatt ccatgttgac atttgggcat     240
gtggccagga gccaatttct accgtacact gggtttagtt gccattgacc atttcctgga     300
aatacttctg cgtgctcctg atgggagcct ctatttggct gtctctaagc caaaaccatt     360
tgtgaccatc aactctgtac tttagttaaa caggatggtg gctggagcca ctggtccccg     420
tggtcatctt gttctgtgac atgtggtgat ggtgtgatca caaggatccg gctctgcaac     480
tctcccagcc cccagatgaa ygggaaaccc tgtgaaggcg aagcgcggga gaccaaagcc     540
tgcaagaaag acgcctgccc cagtaagtgt gaggtccgct gcaagggtga gcatgggcag     600
cagctctgcc cagctggttg cctggcatct gcagcctgca gttcagtggg tcatagagca     660
ggaaggttac ctactagaga acaaacagag agcaaagtcc tgcaggctca gcaacttctt     720
ttaatgaaaa acaaactcac cctcttcccc agcattcttt ccatgtgtca gagaagcaga     780
ggtttcttga acgggcttag gagagtctat gacaagggag ggatttgaaa gttgatctta     840
attgttgcct gtggttcatc ttcttacagt caatggaggc tggggtcctt ggtcaccatg     900
ggacatctgt tctgtcacct gtggaggagg ggtacagaaa cgtagtcgtc tctgcaacaa     960
ccccacaccc cagtttggag gcaaggactg cgttggtgat g                        1001
```

```
<210> SEQ ID NO 5
<211> LENGTH: 1001
<212> TYPE: DNA
<213> ORGANISM: Homo sapiens

<400> SEQUENCE: 5
agatccagaa actcggagcc ccatcagttc ctcacctcat caacatctgt gcactggatg      60
ccatttccac tgtaaccagg gggacaagca ccacatttcc agctgccatc agggtagcta     120
gtacacttca cgccggcaaa gcagggattg acaggcatc catctgagac aaggagagag     180
agacagtcac agtaaatggt tggtctaagc tgccatactg ccatgctggg cacttaacac     240
agtgtaagat attataggt ataggaacc gataacttgt tgggattatg ttgtccacct     300
gcatcttaga gcaatcaaat cgctcaggac taaccaagct ggaatctcct cgaatgctga     360
ctgcagcatt cagtaaaaga gcaaagctcc tgggtcgttt catcctgggc tgcgtggctc     420
accaattgga cagtcctgct tgttgcagat ctggttttct gttacatcac caacgcagtc     480
cttgcctcca aactggggtg yggggttgtt gcagagacga ctacgtttct gtaccctcc     540 tccacaggtg acagaacaga tgtcccatgg tgaccaagga ccccagcctc cattgactgt     600
aagaagatga accacaggca acaattaaga tcaactttca aatccctccc ttgtcataga     660
ctctcctaag cccgttcaag aaacctctgc ttctctgaca catggaaaga atgctggga     720 agagggtgag tttgttttc attaaaagaa gttgctgagc ctgcaggact ttgcttctgt     780
ttgtttctct agtaggtaac cttcctgctc tatgaccac tgaactgcag gctgcagatg     840
ccaggcaacc agctgggcag agctgctgcc catgctcacc cttgcagcgg acctcacact     900
tactggggca ggcgtctttc ttgcaggctt tggtctcccg cgcttcgcct tcacagggtt     960
tcccgttcat ctggggctg ggagagttgc agagccggat c                        1001

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggactctgac ggcgatggtc                                                  20

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atcggcggaa atcggtctc                                                   19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggcatccag ctacgaatc                                                   19
```

```
<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccatggccac aacaactgac                                             20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cgggaaatcg tgcgtgac                                               18

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtggccatct cttgctcgaa                                             20
```

POLYMORPHISM OF THROMBOSPONDIN-1 AS A BIOMARKER FOR SUSCEPTIBILITY TO DRY EYE

CROSS REFERENCE TO RELATED APPLICATIONS

This application is a § 371 National Phase Entry of International Patent Application No. PCT/US2014/27343, filed on Mar. 14, 2014 which claims benefit under 35 U.S.C. § 119(e) of U.S. Provisional Patent Application Ser. No. 61/800,881 filed on Mar. 15, 2013, the contents of which are incorporated herein by reference in their entirety.

GOVERNMENT SUPPORT

This invention was made with Government Support under Contract No. EY015472 awarded by the National Institutes of Health. The Government has certain rights to the invention.

SEQUENCE LISTING

The sequence listing of the present application has been submitted electronically via EFS-Web as an ASCII formatted sequence listing with a file name "701586-080911-PCT SL", creation date of, Jul. 1, 2014, and a size of 36.5 bytes. The sequence listing submitted via EFS-Web is part of the specification and is herein incorporated by reference in its entirety.

FIELD OF INVENTION

Embodiments of the invention relate to single nucleotide polymorphisms (SNPs) in Thrombospondin 1 gene (THBS1) that are herein linked to an increased risk for dry eye (also known as keratoconjunctivitis). The polymorphisms disclosed herein are directly useful for the diagnosis of an increased risk for dry eye, as well as for the determination of patient treatment, e.g. pre and post refractive eye surgery or when the individual has a condition associated with dry eye. Computer systems and medium are also enclosed. The SNPs can be present in unique combinations, or as specific haplotypes indicative of dry eye.

BACKGROUND OF INVENTION

Chronic dry eye is a most common condition encountered in the clinics by Ophthalmologists. It is known to increase with age and is more commonly detected in women. Prevalence of chronic dry eye in some studies is reported at approximately 5 million people>50 years of age in the U.S. and in others to 23 million Americans. It is also a very common condition that develops after refractive surgery. More recently dry eye has been associated with inflammation. However current treatments are primarily palliative approaches while topical application of anti-inflammatory drugs such as steroids and Cyclosporin A (CsA) have met with limited success. In a mouse model where dry eye is induced by exposing animals to desiccating environment with low humidity, development of inflammatory immune response is reported that resembles what is typically seen in autoimmune conditions (Stevenson W, et al. Dry Eye Disease: An Immune-Mediated Ocular Surface Disorder. Arch Ophthalmol. 2012; 130 (1):90-100). Such studies imply that development of dry eye could potentially initiate a chronic inflammatory condition that requires long-term treatment.

Dry eye that develops after refractive surgery, besides causing ocular discomfort may also increase susceptibility to bacterial infections and risk of chronic disease development. A genetic biomarker could serve as a useful tool for the stratification of dry eye disease. Clinical categorization of patients at risk of developing dry eye can help establish the need for a follow on treatment. Biomarkers may also be used as prognostics to improve pharmacodynamics and safety testing for a pre-clinical or clinical phase of drug development.

SUMMARY OF INVENTION

Aspects of the present invention are based, in part, on the discovery of single nucleotide polymorphisms (SNPs) in the Thrombospondin 1 (THBS1) loci that are linked to the development of dry eye, e.g. after refractive eye surgery. The polymorphisms disclosed herein are directly useful for the diagnosis of an increased risk for dry, and thus are useful for determining a need for treatment of dry eye under conditions where dry eye is known to develop, e.g. after refractive eye surgery or in individuals with a condition associated with dry eye. Accordingly, provided herein are methods and computer systems for treating and determining treatment of dry eye.

One aspect of the invention provides methods for treatment of dry eye. The methods comprise a) determination of the presence or absence of at least one single nucleotide polymorphism (SNP) in the THBS1 gene in a biological sample taken from an individual, wherein the SNP is associated with the development of dry eye and is selected from the group consisting of the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3), and b) administering a pharmaceutically effective amount of a dry eye therapeutic to an individual that has the presence of at least one SNP determined associated with the development of dry eye. In one embodiment, the individual is in need of surgery, e.g. refractive eye surgery. In one embodiment of this aspect, the individual has a condition known to be associated with development of dry eye, for example diabetes, lupus, scleroderma, Sjogren's syndrome, thyroid disorders, vitamin A deficiency, and rheumatoid arthritis.

In another aspect of the invention, methods for treatment of dry eye are provided that comprise administering a pharmaceutically effective amount of a dry eye therapeutic to an individual that has been determined to have the presence of at least one single nucleotide polymorphism (SNP) in the THBS1 gene in a biological sample taken from the individual, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3). In one embodiment of these aspects, the individual is need of refractive eye surgery. In one embodiment of this aspect, the individual has a condition known to be associated with development of dry eye, for example diabetes, lupus, scleroderma, Sjogren's syndrome, thyroid disorders, vitamin A deficiency, and rheumatoid arthritis.

In one embodiment of these aspects, a pharmaceutically effective amount of a dry eye therapeutic is administered to an individual that has the presence of at least two single nucleotide polymorphisms (SNPs) associated with dry eye (e.g. SNP1, SNP2, or SNP3).

In another embodiment of these aspects, a pharmaceutically effective amount of a dry eye therapeutic is administered to an individual that has the presence of at least three single nucleotide polymorphisms (SNPs) associated with dry eye (e.g. SNP1, SNP2, or SNP3).

In another aspect, methods for determining a need for treatment of dry eye in an individual are provided. The methods comprise the steps of: a) determining the presence or absence of at least one single nucleotide polymorphism (SNP), in the THBS1 gene in a biological sample taken from an individual, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); b) determining a need for treating the individual for dry eye when the individual has the presence of at least one of the single nucleotide polymorphisms (SNPs) of step a); and c) determining no need for treating the individual for dry eye when the individual lacks each of the single nucleotide polymorphisms (SNPs) of step a). In one embodiment of this aspect, the method further comprises administering a pharmaceutically effective amount of a dry eye therapeutic to an individual determined to be in need of treatment, wherein the therapeutic is administered to the individual before, during, or after the individual undergoes refractive eye surgery. In one embodiment, in step b) of this aspect the individual has the presence of at least two single nucleotide polymorphisms (SNPs) of step a). In another embodiment, in step b) of this aspect the individual has the presence of at least three single nucleotide polymorphisms (SNPs) of step a). In one embodiment of this aspect the individual is in need of refractive eye surgery. In one embodiment, the individual has a condition associated with dry eye. In one embodiment, the condition associated with dry eye is selected from the group consisting of diabetes, rheumatoid arthritis, lupus, scleroderma, Sjogren's syndrome, thyroid disorders, vitamin A deficiency, and rheumatoid arthritis.

In one embodiment of each of the above aspects, the SNP determined herein to be associated with dry eye and indicative of an increased risk of dry eye is the presence of a cytosine "C" allele at position 42 of SEQ ID NO: 1 (THBS1 gene), or its complement thereof (SNP1). This corresponds to nt42T>C on at least one allele, "C" at nt42 being a minor allele.

In one embodiment of each of the above aspects, the SNP determined herein to be associated with dry eye and indicative of an increased risk of dry eye is the presence of a thymine "T" allele at position 7079 of SEQ ID NO: 1, or its complement thereof (SNP2). This corresponds to nt7079C>T on at least one allele, "T" at nt7079 being a minor allele.

In one embodiment of each of the above aspects, the SNP determined herein to be associated with dry eye and indicative of an increased risk of dry eye is the presence of a guanine "G" allele at position 7543 of SEQ ID NO: 1, or its complement thereof (SNP3). This corresponds to nt7543A>G on at least one allele, "G" at nt7543 being a minor allele.

In one embodiment of each of the above aspects, the single nucleotide polymorphisms (e.g. SNP1, SNP2, and SNP3) are present on at least one allele. In one embodiment the SNP is present on two alleles.

In certain embodiments of each of the above aspects the biological sample taken from an individual is selected from the group consisting of: a tissue biopsy, whole blood, plasma, serum urine, saliva, cerebrospinal fluid and a conjunctival impression cytology (CIC) sample.

In one embodiment of each of the above aspects, the presence or absence of at least one single nucleotide polymorphism (SNP) in the THBS1 gene is determined by genotyping nucleic acid derived from the biological sample using a method selected from the group consisting of: single-strand conformational polymorphism (SSCP) analysis, long range polymerase chain reaction (PCR), and allele specific hybridization.

In one embodiment of each of the above aspects, the methods further comprise measuring expression of interleukin-1 beta in the biological sample. An increased expression of interleukin-1 beta as compared to the expression level typically observed in a biological sample of the same type from a healthy individual indicates that the individual likely has chronic dry eye disease. The combination of SNP determination and observance of interleukin-1 beta expression in an individual is a means for a more accurate diagnosis of chronic dry eye disease having associated chronic ocular inflammation.

In one embodiment of each of the above aspects, the dry eye therapeutic used in the methods herein is selected from the group consisting and of: a lubricating substance and an immunosuppressant.

Additional aspects of the invention further provide for assays; systems, and computer readable media for causing computer systems, to perform a method for determining whether an individual has a pre-disposition (an increased risk) for dry eye based on sequence information of the THBS1 gene.

In one aspect, an assay is provided that comprises genotyping the THBS1 loci of nucleic acid in a biological sample taken from an individual to detect the presence or absence of at least one single nucleotide polymorphism (SNP) in the THBS1 gene; wherein the presence of at least one SNP selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); indicates that the individual is at risk of developing dry eye and in need of treatment for dry eye post refractive eye surgery. In one embodiment, the presence of at least two single nucleotide polymorphisms (SNPs) of step a) indicates the individual is at risk for developing dry eye and in need of treatment. In one embodiment, the presence of at least three single nucleotide polymorphisms (SNPs) of step a) indicates the individual is at risk of development of dry eye and in need of treatment.

In one aspect, a system is provided for analyzing data of a biological sample (e.g. data either generated within the system or generated separately and entered into system). The system determines an increased risk for dry eye in an individual. The system comprises a) a determination module configured to receive sequence data, and to determine sequence information, wherein the sequence information comprises a sequence of a coding or non-coding region of THBS1 gene or protein, obtained from a biological sample; b) a storage device configured to store sequence information from the determination module; c) a comparison module adapted to compare the sequence information stored on the storage device with reference data, and to provide a comparison result, wherein the comparison result identifies the presence or absence of a single nucleotide polymorphism (SNP), or corresponding amino acid change in THBS1 gene or protein, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); and wherein the SNP is indicative of an increased risk for dry eye disease; and d) a display module for displaying a content based in part on the comparison result for the user, wherein the content is a signal indicative of an increased risk for dry eye in the presence of at least one SNP of step c), or a signal indicative of lack of an increased risk for dry eye in the absence of each of the SNPs of step c).

In one embodiment of this aspect, in step d) of the system, the content is a signal indicative of an increased risk for dry eye in the presence of at least two single nucleotide polymorphisms SNPs of step c), or a signal indicative of lack of an increased risk for dry eye in the absence of two of the SNPs of step c).

In one embodiment of this aspect, in step d) of the system, the content is a signal indicative of an increased risk for dry eye in the presence of at least three single nucleotide polymorphisms SNPs of step c), or a signal indicative of lack of an increased risk for dry eye in the absence of one of the SNPs of step c).

In another aspect, a computer readable medium is provided. The computer readable medium has computer readable instructions recorded thereon to define software modules including a comparison module and a display module for implementing a method on a computer, said method comprising: a) comparing with the comparison module the data stored on a storage device with reference data to provide a comparison result, wherein the comparison result identifies the presence or absence of a single nucleotide polymorphisms, or corresponding amino acid changes in THBS1 gene or protein, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); and wherein the SNP is indicative of an increased risk for dry eye; and b) displaying a content based in part on the comparison result for the user, wherein the content is a signal indicative of an increased risk of dry eye in the presence of at least one SNP of step a), or a signal indicative of lack of an increased risk for dry eye in the absence of each of the SNPS of step a). In one embodiment displaying a content based in part on the comparison result for the user, wherein the content is a signal indicative of an increased risk of dry eye when there is the presence of at least two single nucleotide polymorphisms SNPs of step a), or a signal indicative of lack of an increased risk for dry eye in the absence two of the SNPs of step a). In one embodiment displaying a content based in part on the comparison result for the user, wherein the content is a signal indicative of an increased risk of dry eye when there is the presence of at least three single nucleotide polymorphisms SNPs of step a), or a signal indicative of lack of an increased risk for dry eye in the absence one of the SNPs of step a).

Also provided in the invention are kits that comprise a combination of two to three SNP detection reagents, and methods for detecting the SNPs in THBS1 by employing detection reagents. The kit provides methods of identifying an individual having an increased or decreased risk of developing dry eye by detecting the presence or absence of a SNP allele. A kit for determining an increased risk of dry eye in an individual by detecting a SNP associated with dry eye comprises a primer and a probe, wherein the probe selectively hybridizes to the SNP-containing nucleic acid molecules as compared to a nucleic acid molecule which does not contain the SNP at the same nucleotide position, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3). In one embodiment the kit comprises at least three probes enabling detection of SNP1, SNP2, and SP3 as described herein. In one embodiment the kit comprises at least two probes enabling detection of SNP1, SNP2, or SP3 as described herein. The detecting of a SNP can be carried out by a process selected from the group consisting of: allele specific probe hybridization, allele-specific primer extension, allele-specific amplification, sequencing, 5' nuclease digestion, molecular beacon assay, DNA chip analysis, oligonucleotide ligation assay, size analysis, and single stranded confirmation polymorphism. In one embodiment, the kit further comprises one or more buffers, such as a DNA amplification buffer, DNA isolation buffer or hybridization buffer, and/or enzymes such as DNA polymerase, ligase, and/or chain extension nucleotides such as deoxynucleotide triphosphates.

BRIEF DESCRIPTION OF THE FIGURES

FIG. 6 shows a table of diagnostic criteria for post-refractive surgery dry eye.

FIG. 7 shows a table of a description and location of the analyzed THBS1 polymorphisms.

FIG. 8 shows a table of the characteristics of total population of dry eye.

FIG. 9 shows a table of characteristics of study population of dry eye in Example 1.

FIG. 10 shows a table of the Allelic frequencies of analyzed thrombospondin-1 gene (THBS1) polymorphisms in the study population of Example 1 and HapMap population of Example 1.

FIG. 11 shows a table of the thrombospondin-1 gene (THBS1) polymorphisms in patients with post-refractive surgery dry eye.

FIG. 12 shows a table of haplotype frequencies of thrombospondin-1 gene (THBS1) polymorphisms in patients with post-refractive surgery dry eye.

DETAILED DESCRIPTION

Figure 1:
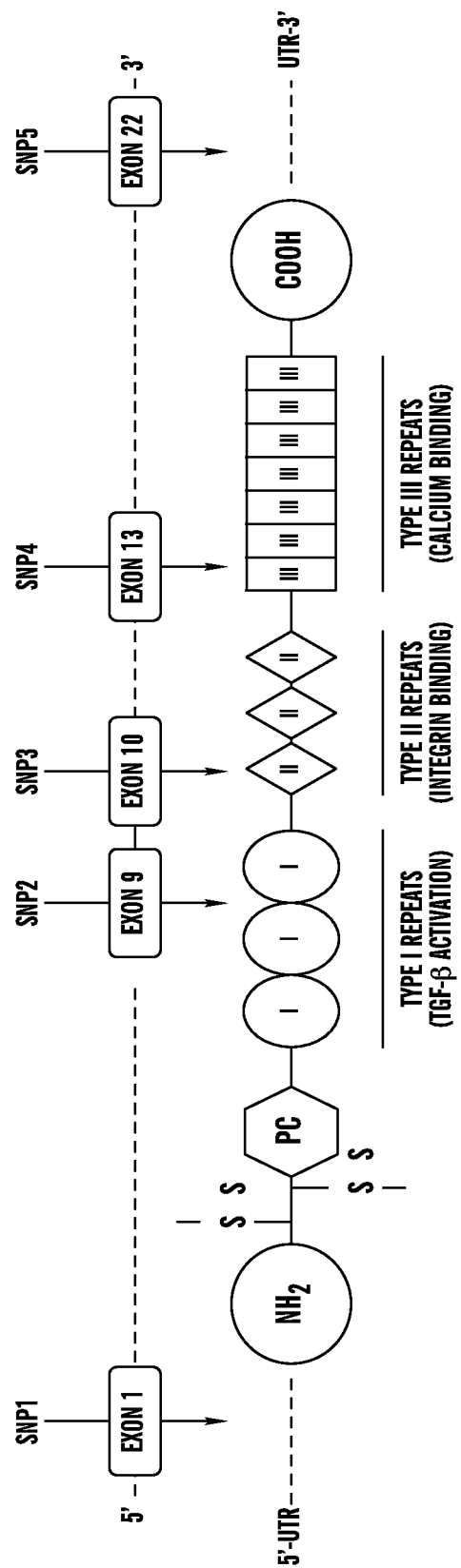
FIG. 1 shows a schematic of the location of genotyped thrombospondin-1 gene (THBS1) polymorphisms. UTR: untranslated region; $NH_2$: globular N-terminal domain; S-S: interchain disulfide bonds; PC: procollagen homology domain; I: type I repeats; II: type II repeats; III: type III repeats; COOH: globular C-terminal domain

All patents, patent applications, and publications identified herein are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of the invention are based, in part, upon the discovery of three single nucleotide polymorphisms (SNPs) at the thrombospondin-1 gene (THBS1) locus that are linked to the development of dry eye in patients. These polymorphisms are directly useful for the diagnosis of an increased risk for dry, and thus are useful for determining a need for treatment of dry eye under conditions where dry eye is known to develop, e.g. after eye surgery such as refractive eye surgery, or in conditions associated with dry eye, such as diabetes or rheumatoid arthritis, among others. Accordingly, provided herein are methods and computer systems for treating and determining treatment of dry eye.

To identify the SNPs, conjunctival impression cytology samples were collected from individuals in need of refractive eye surgery. The samples were collected before refractive eye surgery and were used to harvest DNA for genotyping five THBS1 SNPs (rs1478604 (SNP1), rs2228262 (SNP2), rs2292305 (SNP3), rs2228262 (SNP4) and rs3743125 (SNP5)) using the Sequenom iPLEX Gold platform (Sequenom. San Diego). Participants were followed for a total period of one year after surgery to monitor the status of keratoconjunctivitis; chronic ocular surface inflammation. In accordance with the present invention, it has been discovered that the presence of three of the five polymorphisms in the coding and/or non-coding regions of the THBS1 gene (THBS1 locus) identifies individuals with an increased risk of the development of dry eye. The SNPs associated with dry eye occur within and near the THBS1 gene coding regions of the THBS1 locus; and are represented herein as SNP1, SNP2 and SNP3, See Example I.

As used herein "SNP1" refers to the presence of a cytosine "C" allele at position 42 of SEQ ID NO: 1, or its complement thereof. This corresponds to nt42T>C on at least one allele, "C" at nt42 being a minor allele, reference to SEQ ID NO: 1. Alternative names of SNP1 include accession rs1478604 A>G in 5' untranslated region; −138T>C; 10663878T>C; and 39873321T>C; Genebank Accessions: NC_000015.9:g.39873321T>C; NM_003246.2:c.−138T>C; NT_010194.17:g.10663878T>C As used herein "SNP2" refers to the presence of a thymine "T" allele at position 7079 of SEQ ID NO: 1, or its complement thereof (SNP2). This corresponds to nt7079C>T on at least one allele, "T" at nt7079 being a minor allele reference to SEQ ID NO: 1. Alternate names of SNP2 include accession rs2228261 at 15:39880358 in THBS1; 10670915C>T; 1410C>T; 39880358C>T; and Asn470; Genebank Accessions: NC_000015.9: g.39880358C>T, NM_003246.2:c.1410C>T, NP_003237.2: p.Asn470, NT_010194.17:g.10670915C>T.

As used herein "SNP3" refers to the presence of a guanine "G" allele at position 7543 of SEQ ID NO: 1, or its complement thereof (SNP3). This corresponds to nt7543A>G on at least one allele, "G" at nt7543 being a minor allele, reference SEQ ID NO: 1. Alternate names of SNP3 include accession rs2292305 at 15:39880822 in THBS1; Thr523Ala; 10671379A>G, 1567A>G, and 39880822A>G; Genebank Accessions: NC_000015.9: g.39880822A>G, NM_003246.2:c.1567A>G, NP_003237.2:p.Thr523Ala, NT_010194.17: g.10671379A>G.

As used herein, the term "THBS1 locus" refers to the genomic locus of the thrombospondin-1 gene THBS1, and corresponds to nucleotides 39581079-39597467 of Chromosome 15 Genebank Accession number NC_000015 REGION: 39581079 ... 39597467 (SEQ ID NO: 1). THBS1 encodes the thrombospondin-1 protein (SEQ ID NO: 2). The following abbreviations are synonyms of the THSB1 gene: TSP; THBS; TSP1; TSP-1; THBS-1. The thrombospondin 1 (THBS-1) protein encoded by this gene is a subunit of a disulfide-linked homotrimeric protein. The protein is an adhesive glycoprotein that mediates cell-to-cell and cell-to-matrix interactions, for example by binding to fibrinogen, fibronectin, laminin, type V collagen and integrins alpha-V/beta-1. THBS-1 protein has been shown to play roles in platelet aggregation, angiogenesis, and tumorigenesis.

As used herein, the term "dry eye" refers to keratoconjunctivitis sicca (KCS), also called keratitis sicca, xerophthalmia, or dry eye syndrome (DES). It is an eye disease caused by eye dryness, which is caused by either decreased tear production and/or increased tear film evaporation. In one embodiment, the methods, systems and media described herein indicate an increased risk of developing chronic keratoconjunctivitis, also called chronic dry eye, chronic xerophthalmia, or chronic dry eye syndrome (DES). In one embodiment, the methods, systems and media described herein indicate an increased risk of developing, chronic ocular surface inflammation as seen in dry eye.

Methods, computer systems, media, and assays are provided for determining an increased risk of dry eye in an individual. In embodiments, determination of an increased risk for dry eye comprises determining the THBS1 locus genotype in a biological sample taken from an individual. The presence of one or more single nucleotide polymorphisms (SNPs) in thrombospondin 1 gene (THBS1) determined herein to be associated with dry eye (i.e. SNP1, SNP2, and SNP3) is indicative that the individual is at risk of development of dry eye. In embodiments of the invention, when individuals are identified as having an increased risk of dry eye, a specialized treatment regime designed for treatment of dry eye is indicated. For example, identified individuals can be treated with a dry eye therapeutic, i.e. administered a therapeutically or prophylactically effective amount of one or more agents that counteract dry eye.

Detection of Polymorphisms

According to the present invention, any approach that detects mutations or polymorphisms in the THBS1 gene can be used, including but not limited to single-strand conformational polymorphism (SSCP) analysis (Orita et al. (1989) Proc. Natl. Acad. Sci. USA 86:2766-2770), heteroduplex analysis (Prior et al. (1995) Hum. Mutat. 5:263-268), oligonucleotide ligation (Nickerson et al. (1990) Proc. Natl. Acad. Sci. USA 87:8923-8927) and hybridization assays (Conner et al. (1983) Proc. Natl. Acad. Sci. USA 80:278-282). Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296-6300), and coupled amplification and sequencing (CAS) (Ruano and Kidd (1991) Nucleic Acids Res. 19:6877-6882), are easily performed and highly sensitive methods to determine haplotypes (Michalatos-Beloin et al. (1996) Nucleic Acids Res. 24:4841-4843; Barnes (1994) Proc. Natl. Acad. Sci. USA 91:5695-5699; Ruano and Kidd (1991) Nucleic Acids Res. 19:6877-6882).

In one embodiment, a long-range PCR (LR-PCR) is used to detect mutations or polymorphisms. LR-PCR products are genotyped for mutations or polymorphisms using any genotyping methods known to one skilled in the art, and haplotypes inferred using mathematical approaches (e.g., Clark's algorithm (Clark (1990) Mol. Biol. Evol. 7:111-122).

For example, methods including complementary DNA (cDNA) arrays (Shalon et al., Genome Research 6(7):639-45, 1996; Bernard et al., Nucleic Acids Research 24(8):1435-42, 1996), solid-phase mini-sequencing technique (U.S. Pat. No. 6,013,431, Suomalainen et al. Mol. Biotechnol. June; 15(2):123-31, 2000), ion-pair high-performance liquid chromatography (Doris et al. J. Chromatogr. A May 8; 806(1):47-60, 1998), and 5' nuclease assay or real-time RT-PCR (Holland et al. Proc Natl Acad Sci USA 88: 7276-7280, 1991), or primer extension methods described in the U.S. Pat. No. 6,355,433, can be used.

In one embodiment, the primer extension reaction and analysis is performed using PYROSEQUENCING™ (Uppsala, Sweden) which essentially is sequencing by synthesis. A sequencing primer, designed directly next to the nucleic acid differing between the disease-causing mutation and the normal allele or the different SNP alleles is first hybridized to a single stranded, PCR amplified DNA template from the individual, and incubated with the enzymes, DNA polymerase, ATP sulfurylase, luciferase and apyrase, and the substrates, adenosine 5' phosphosulfate (APS) and luciferin. For detailed information about reaction conditions for the PYROSEQUENCING, see, e.g. U.S. Pat. No. 6,210,891, which is herein incorporated by reference in its entirety.

Another example of the methods useful for detecting mutations or polymorphisms is real time PCR. Real-time PCR systems rely upon the detection and quantification of a fluorescent reporter, the signal of which increases in direct proportion to the amount of PCR product in a reaction. Examples of real-time PCR method useful according to the present invention include, TaqMan® (Life Technologies, Grand Island, N.Y.) and molecular beacons, both of which use hybridization probes relying on fluorescence resonance energy transfer (FRET) for quantitation. TaqMan® (Life Technologies, Grand Island, N.Y.) probes are oligonucleotides that contain a fluorescent dye, typically on the 5' base, and a quenching dye, typically located on the 3' base. When irradiated, the excited fluorescent dye transfers energy to the nearby quenching dye molecule rather than fluorescing, resulting in a nonfluorescent substrate. TaqMan® probes (Life Technologies, Grand Island, N.Y.) are designed to hybridize to an internal region of a PCR product (ABI 7700, Applied BioSystems, Foster City, Calif.). For example TaqMan® (Life Technologies, Grand Island, N.Y.) probes can be generated to specifically hybridize to SNPs 1-3 described herein. Accordingly, two different primers, one hybridizing to the mutation or polymorphism and the other to the corresponding wildtype allele, are designed. The primers are consequently allowed to hybridize to the corresponding nucleic acids in the real time PCR reaction. During PCR, when the polymerase replicates a template on which a TaqMan® (Life Technologies, Grand Island, N.Y.) probe is bound, the 5' exonuclease activity of the polymerase cleaves the probe. Consequently, this separates the fluorescent and quenching dyes and FRET no longer occurs. Fluorescence increases in each cycle, proportional to the rate of probe cleavage.

Molecular beacons also contain fluorescent and quenching dyes, but FRET only occurs when the quenching dye is directly adjacent to the fluorescent dye. Molecular beacons are designed to adopt a hairpin structure while free in solution, bringing the fluorescent dye and quencher in close proximity. Therefore, for example, two different molecular beacons are designed, one recognizing the mutation or polymorphism (SNP1, SNP2, or SNP3) and the other the corresponding wildtype allele. When the molecular beacons hybridize to the nucleic acids, the fluorescent dye and quencher are separated, FRET does not occur, and the fluorescent dye emits light upon irradiation. Unlike TaqMan probes (Life Technologies, Grand Island, N.Y.), molecular beacons are designed to remain intact during the amplification reaction, and must rebind to target in every cycle for signal measurement. TaqMan probes (Life Technologies, Grand Island, N.Y.) and molecular beacons allow multiple DNA species to be measured in the same sample (multiplex PCR), since fluorescent dyes with different emission spectra may be attached to the different probes, e.g. different dyes are used in making the probes for different disease-causing and SNP alleles. Multiplex PCR also allows internal controls to be co-amplified and permits allele discrimination in single-tube assays. (Ambion Inc, Austin, Tex., TechNotes 8(1)-February 2001, Real-time PCR goes prime time).

Yet another method useful according to the present invention for detecting the SNPs herein, is solid-phase mini-sequencing (Hultman, et al., 1988, Nucl. Acid. Res., 17, 4937-4946; Syvanen et al., 1990, Genomics, 8, 684-692). The solid-phase mini-sequencing method is described in detail, for example, in the U.S. Pat. No. 6,013,431 and in Wartiovaara and Syvanen, Quantitative analysis of human DNA sequences by PCR and solid-phase minisequencing. Mol Biotechnol 2000 June; 15(2):123-131.

Mutations or polymorphisms may also be detected using allele-specific hybridization followed by a MALDI-TOF-MS detection of the different hybridization products. In the preferred embodiment, the detection of the enhanced or amplified nucleic acids representing the different alleles is performed using matrix-assisted laser desorption ionization/time-of-flight (MALDI-TOF) mass spectrometric (MS) analysis.

A DNA haplotype, the phase determined association of several polymorphic markers (e.g., SNPs), is a statistically much more powerful method than the use of single markers alone for determining disease associations. Approaches for determining and identifying the haplotypes according to the present invention include a physical separation of homologous chromosomes via for example means of mouse cell line hybrid, cloning into a plasmid and allele specific PCR as well as computational determination of haplotypes. According to the present invention, approaches that can be used to haplotype SNPs in the THBS1 locus include, but are not limited to, single-strand conformational polymorphism (SSCP) analysis (Orita et al. (1989) Proc. Natl. Acad. Sci. USA 86:2766-2770), heteroduplex analysis (Prior et al. (1995) Hum. Mutat. 5:263-268), oligonucleotide ligation (Nickerson et al. (1990) Proc. Natl. Acad. Sci. USA 87:8923-8927) and hybridization assays (Conner et al. (1983) Proc. Natl. Acad. Sci. USA 80:278-282). Traditional Taq polymerase PCR-based strategies, such as PCR-RFLP, allele-specific amplification (ASA) (Ruano and Kidd (1989) Nucleic Acids Res. 17:8392), single-molecule dilution (SMD) (Ruano et al. (1990) Proc. Natl. Acad. Sci. USA 87:6296-6300), and coupled amplification and sequencing (CAS) (Ruano and Kidd (1991) Nucleic Acids Res. 19:6877-6882), are easily performed and highly sensitive methods to determine haplotypes of the present invention (Michalatos-Beloin et al. (1996) Nucleic Acids Res. 24:4841-4843; Barnes (1994) Proc. Natl. Acad. Sci. USA 91:5695-5699; Ruano and Kidd (1991) Nucleic Acids Res. 19:6877-6882).

In one embodiment, a long-range PCR (LR-PCR) is used to haplotype SNPs of the present invention. LR-PCR products are genotyped for SNPs using any genotyping methods known to one skilled in the art, and haplotypes inferred using mathematical approaches (e.g., Clark's algorithm (Clark (1990) Mol. Biol. Evol. 7:111-122).

In one embodiment, a haplotyping method useful according to the present invention is a physical separation of alleles by cloning, followed by sequencing. Other methods of haplotyping, useful according to the present invention include, but are not limited to monoallelic mutation analysis (MAMA) (Papadopoulos et al. (1995) Nature Genet. 11:99-102) and carbon nanotube probes (Woolley et al. (2000) Nature Biotech. 18:760-763). U.S. Patent Application No. US 2002/0081598 also discloses a useful haplotying method which involves the use of PCR amplification. Computational algorithms such as expectation-maximization (EM), subtraction and PHASE are useful methods for statistical estimation of haplotypes (see, e.g., Clark, A. G. Inference of haplotypes from PCR-amplified samples of diploid populations. Mol Biol Evol 7, 111-22. (1990); Stephens, M., Smith, N. J. & Donnelly, P. A new statistical method for haplotype reconstruction from population data. Am J Hum Genet 68, 978-89. (2001); Templeton, A. R., Sing, C. F., Kessling, A. & Humphries, S. A cladistic analysis of phenotype associations with haplotypes inferred from restriction endonuclease mapping. II. The analysis of natural populations. Genetics 120, 1145-54. (1988)).

The polymorphisms are preferably analyzed using methods amenable for automation such as the different methods for primer extension analysis. Primer extension analysis can be performed using any method known to one skilled in the art including PYROSEQUENCING™ (Uppsala, Sweden); Mass Spectrometry including MALDI-TOF, or Matrix Assisted Laser Desorption Ionization—Time of Flight; genomic nucleic acid arrays (Shalon et al., Genome Research 6(7):639-45, 1996; Bernard et al., Nucleic Acids Research 24(8):1435-42, 1996); solid-phase mini-sequencing technique (U.S. Pat. No. 6,013,431, Suomalainen et al. Mol. Biotechnol. June; 15(2):123-31, 2000); ion-pair high-performance liquid chromatography (Doris et al. J. Chromatogr. A May 8; 806(1):47-60, 1998); and 5' nuclease assay or real-time RT-PCR (Holland et al. Proc Natl Acad Sci USA 88: 7276-7280, 1991), or primer extension methods described in the U.S. Pat. No. 6,355,433. Nucleic acids sequencing, for example using any automated sequencing system and either labeled primers or labeled terminator dideoxynucleotides can also be used to detect the polymorphisms. Systems for automated sequence analysis include, for example, Hitachi FMBIO® and Hitachi FMBIO® II Fluorescent Scanners (Hitachi Genetic Systems, Alameda, Calif.); Spectrumedix® SCE 9610 Fully Automated 96-Capillary Electrophoresis Genetic Analysis System (SpectruMedix LLC, State College, Pa.); ABI PRISM® 377 DNA Sequencer; ABI® 373 DNA Sequencer; ABI PRISM® 310 Genetic Analyzer; ABI PRISM® 3100 Genetic Analyzer; ABI PRISM® 3700 DNA Analyzer (Applied Biosystems, Headquarters, Foster City, Calif.); Molecular Dynamics FluorImager™ 575 and SI Fluorescent Scanners and Molecular Dynamics FluorImager™ 595 Fluorescent Scanners (Amersham Biosciences UK Limited, Little Chalfont, Buckinghamshire, England); GenomyxSC™ DNA Sequencing System (Genomyx Corporation (Foster City, Calif.); Pharmacia ALF™ DNA Sequencer and Pharmacia ALFexpress™ (Amersham Biosciences UK Limited, Little Chalfont, Buckinghamshire, England). PCR, nucleic acid sequencing and primer extension reactions for one nucleic acid sample can be performed in the same or separate reactions using the primers designed to amplify and detect the polymorphic THBS/nucleotides.

SNP Detection Reagents

SNP detection kits/systems may contain, for example, one or more probes, or pairs of probes, that hybridize to a nucleic acid molecule at or near each target SNP position (SNP-detection reagents). It should be noted that the primers and probes specific for identification of SNP1, SNP2 and SNP3 can be used in in specific combinations for kits. Such kits provide a means for an assay that enables determination of the risk that an individual will develop dry eye.

Multiple pairs of allele-specific probes may be included in the kit/system to simultaneously assay large numbers of SNPs, at least one of which is a SNP of the present invention. In some kits/systems, the allele-specific probes are immobilized to a substrate such as an array or bead. For example, the same substrate can comprise allele-specific probes for detecting at least 1; 10; 100; 1000; 10,000; 100,000 (or any other number in-between) or substantially all of the SNPs disclosed herein. In one embodiment the kit further comprises probes/primers useful for detection of expression levels of Interleukin-beta.

In one embodiment, the kit or system of the invention provides a nucleic acid chip including the polymorphic THBS1 alleles for the screening of the individual with a risk of dry eye, or THBS1-associated protection from dry eye. Methods and techniques applicable to array synthesis have been described in U.S. Ser. No. 09/536,841, WO 00/58516, U.S. Pat. Nos. 412,087, 6,147,205, 6,262,216, 6,310,189, 5,889,165, and 5,959,098, 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes. Additional methods of sample preparation and techniques for reducing the complexity of a nucleic sample are described, for example, in Dong et al., *Genome Research* 11, 1418 (2001), in U.S. Pat. Nos. 6,361,947, 6,391,592 and U.S. patent application Ser. Nos. 09/916,135, 09/920,491, 09/910,292, and 10/013,598.

Methods for conducting polynucleotide hybridization assays on the chips have been well developed in the art. Hybridization assay procedures and conditions will vary depending on the application and are selected in accordance with the general binding methods known including those referred to in: Maniatis et al. *Molecular Cloning: A Laboratory Manual* (2$^{nd}$ Ed. Cold Spring Harbor, N. Y, 1989); Berger and Kimmel *Methods in Enzymology*, Vol. 152, *Guide to Molecular Cloning Techniques* (Academic Press, Inc., San Diego, Calif., 1987); Young and Davism, *P.N.A.S,* 80: 1194 (1983). Methods and apparatus for carrying out repeated and controlled hybridization reactions have been described, for example, in U.S. Pat. Nos. 5,871,928, 5,874,219, 6,045,996 and 6,386,749, 6,391,623, each of which are incorporated herein by reference Examples of methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Examples of identifying polymorphisms and applying that information in a way that yields useful information regarding patients can be found, for example, in U.S. Pat. No. 6,472,157; U.S. Patent Application Publications 20020016293, 20030099960, 20040203034; WO 0180896, all of which are hereby incorporated by reference.

Typically, the SNP detection reagents of the kits or system herein, hybridize to the target SNP-containing nucleic acid molecule by complementary base-pairing in a sequence specific manner, and discriminates the target variant sequence from other nucleic acid sequences such as an art-known form in a test sample. An example of a detection reagent is a probe that hybridizes to a target nucleic acid containing one or more of the SNPs disclosed herein. In a some embodiments, such a probe can differentiate between nucleic acids having a particular nucleotide (allele) at a target SNP position from other nucleic acids that have a different nucleotide at the same target SNP position. In addition, a detection reagent may hybridize to a specific region 5' and/or 3' to a SNP position, particularly a region corresponding to the SNP context sequences. Another example of a detection reagent is a primer which acts as an initiation point of nucleotide extension along a complementary strand of a target polynucleotide. The SNP sequence information provided herein is also useful for designing primers, e.g. allele-specific primers, to amplify (e.g., using PCR) any SNP of the present invention, for example as provided in SEQ ID NO: 6 or SEQ ID NO: 7. In some embodiments, the SNP detection reagent is substantially complimentary to the target nucleic acid.

In one embodiment of the invention, a SNP detection reagent is an isolated or synthetic DNA or RNA polynucleotide probe or primer or PNA oligomer, or a combination of DNA, RNA and/or PNA, that hybridizes to a segment of a target nucleic acid molecule containing a SNP identified herein. A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form a SNP detection kit.

A probe or primer typically is a substantially purified oligonucleotide or PNA oligomer. Such oligonucleotide typically comprises a region of complementary nucleotide sequence that hybridizes under stringent conditions to at least about 8, 10, 12, 16, 18, 20, 22, 25, 30, 40, 50, 60, 100 (or any other number in-between) or more consecutive nucleotides in a target nucleic acid molecule. Depending on the particular assay, the consecutive nucleotides can either include the target SNP position, or be a specific region in close enough proximity 5' and/or 3' to the SNP position to carry out the desired assay.

It will be apparent to one of skill in the art that such primers and probes are directly useful as reagents for genotyping the SNPs of the present invention, and can be incorporated into any kit/system format.

In order to produce a probe or primer specific for a target SNP-containing sequence, the gene/transcript and/or context sequence surrounding the SNP of interest is typically examined using a computer algorithm which starts at the 5' or at the 3' end of the nucleotide sequence. Typical algorithms will then identify oligomers of defined length that are unique to the gene/SNP context sequence, have a GC content within a range suitable for hybridization, lack predicted secondary structure that may interfere with hybridization, and/or possess other desired characteristics or that lack other undesired characteristics.

A primer or probe of the present invention is typically at least about 8 nucleotides in length. In one embodiment of the invention, a primer or a probe is at least about 10 nucleotides in length. In a preferred embodiment, a primer or a probe is at least about 12 nucleotides in length. In a more preferred embodiment, a primer or probe is at least about 16, 17, 18, 19, 20, 21, 22, 23, 24 or 25 nucleotides in length. While the maximal length of a probe can be as long as the target sequence to be detected, depending on the type of assay in which it is employed, it is typically less than about 50, 60, 65, or 70 nucleotides in length. In the case of a primer, it is typically less than about 30 nucleotides in length. In a specific embodiment, a primer or a probe is within the length of about 18 and about 28 nucleotides. However, in other embodiments, such as nucleic acid arrays and other embodiments in which probes are affixed to a substrate, the probes can be longer, such as on the order of 30-70, 75, 80, 90, 100, or more nucleotides in length. In certain embodiments, it will be advantageous to employ SNP detection reagents of the present invention in combination with an appropriate means, such as a label, for determining hybridization.

Detection of Variant THBS1 Protein

In certain embodiments, to determine the presence or absence of a SNP one can look for a SNP by detecting the corresponding change in the THBS1 gene product (the THBS-1 protein is SEQ ID NO: 2). For example SNP3 is associated with a threonine to alanine change: NP_003237.2:p.Thr523Ala.

Detection of an amino acid change can be readily done by standard means such as by sequencing, or by antibodies that recognize specific epitopes.

Amplification of Nucleic Acids from Biological Samples for SNP Detection

In some embodiments, e.g. in the methods and assays described herein, amplified nucleic acids are used for detection of the polymorphisms. Nucleic acids used as a template for amplification, or for other means of analysis described herein, may be isolated from biological samples taken from an individual, e.g. cells, tissues or other samples.

Biological samples used as a source material for isolating the nucleic acids include solid materials (e.g., tissue, cell pellets, biopsies) and biological fluids (e.g. blood, saliva, amniotic fluid, mouth wash, urine, spinal fluid, pleural fluid, nipple aspirates, lymph fluid). Nucleic acid molecules of the instant invention include DNA and RNA and can be isolated from a particular biological sample using any of a number of procedures, which are well-known in the art, the particular isolation procedure chosen being appropriate for the particular biological sample. Standard methodologies for isolation are found in, for example, the Molecular Cloning: A Laboratory Manual, 3rd Ed., Sambrook and Russel, Cold Spring Harbor Laboratory Press, Cold Spring Harbor N.Y. 2001.

In one embodiment, nucleic acid is isolated from conjunctival impression cytology (CCI) samples. Impression cytology is carried out by pressing a small piece of special filter paper against the anaesthetized bulbar conjunctiva for a few seconds prior to removal. The operation is usually repeated two or three times over the same area. The cells can then be processed for isolation of nucleic acid.

In certain embodiments, analysis is performed on whole cell or tissue homogenates or biological fluid samples with or without substantial purification of the template nucleic acid. The nucleic acid may be genomic DNA, or fractionated, or whole cell RNA. Where RNA is used, it may be desired to first convert the RNA to a complementary DNA.

A number of template dependent processes are available to amplify the nucleic acid sequences present in a given sample. One of the best known amplification methods is the polymerase chain reaction (referred to as PCR) which is described in detail in U.S. Pat. Nos. 4,683,195, 4,683,202 and 4,800,159, and in Tinnis et al., 1988, each of which is incorporated herein by reference in their entirety. Another method for amplification is ligase chain reaction ("LCR"), disclosed in European Application No. 320,308, and is incorporated herein by reference in its entirety. U.S. Pat. No. 4,883,750 describes a method similar to LCR for binding probe pairs to a target sequence. A method based on PCR and oligonucleotide ligase assay (OLA) (described in further detail below), disclosed in U.S. Pat. No. 5,912,148, may also be used.

Detection of Nucleic Acids Following any Amplification

It may be desirable to separate the amplification product from the template and/or the excess primer. In one embodiment, amplification products are separated by agarose, agarose-acrylamide or polyacrylamide gel electrophoresis using standard methods (Sambrook et al., 2001; the Molecular Cloning: A Laboratory Manual, 3rd Ed., Sambrook and Russel, Cold Spring Harbor Laboratory Press, Cold Spring Harbor N.Y. 2001). Separated amplification products may be cut out and eluted from the gel for further manipulation. Using low melting point agarose gels, the separated band may be removed by heating the gel, followed by extraction of the nucleic acid. Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under W light. Alternatively, if the amplification products are integrally labeled with radio- or fluorometrically-labeled nucleotides, the separated amplification products card be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see the Molecular Cloning: A Laboratory Manual, 3rd Ed., Sambrook and Russel, Cold Spring Harbor Laboratory Press, Cold Spring Harbor N.Y. 2001). One example of the foregoing is described in U.S. Pat. No. 5,279,721, incorporated by reference herein, which discloses an apparatus and method for the automated electrophoresis and transfer of nucleic acids. The apparatus permits electrophoresis I and blotting without external manipulation of the gel and is ideally suited to carrying out methods according to the present invention.

Other methods of nucleic acid detection that may be used in the practice of the invention are disclosed in U.S. Pat. Nos. 5,840,873, 5,843,640, 5,843,651, 5,846,708, 5,846, 717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

Screening for Predisposition to Dry Eye

Embodiments of the invention provide for methods of diagnosing or determining an increased risk of dry eye in an individual comprising determining the THBS1 locus genotype in a biological sample from the individual, wherein presence of one or more of the dry eye associated SNPs (SNP1, SNP2, SNP3) in THBS1 is indicative that the individual is at risk of dry eye. The SNP1, SNP2, and SNP3 polymorphisms in the THBS1 gene are useful for diagnosing, screening for, and evaluating predisposition to dry eye pathologies.

The methods and assays of the present invention may employ any variety of methodologies to determine whether a test subject has a SNP or SNP pattern indicative of an increased or decreased risk of dry eye, including, but not limited to, the polymorphism detection techniques disclosed herein. The methods generally involve, for example, analyzing a nucleic acid sample from an individual to determine which nucleotide(s) is/are present at one or more SNP positions, wherein the assayed nucleotide(s) is/are indicative of an increased or decreased risk of developing dry eye. Means for obtaining nucleic acid samples from an individual are well known to those of skill in the art. In one embodiment, a nucleic acid sample is obtained from conjunctival impression cytology (CIC) samples and the regions of the THBS1 gene where the SNP occurs is amplified through polymerase chain reaction (PCR) prior to SNP analysis, e.g. by sequencing.

According to embodiments of the present invention, if the individual does not have a variant allele(s) associated with dry eye, for example, the absence of SNP1, SNP2 and SNP3 then the individual is not at an increased risk of developing dry eye, and thus placement of the individual on a treatment regime is not indicated. As described in Example 1, the absence of SNP1, SNP2, and SNP3 provides a protective effect against development of dry eye. Alternatively, if the individual has at least one of the variant allele(s) disclosed herein to be associated with dry eye than the individual is at an increased risk of developing dry eye under conditions known to be associated with dry eye, e.g. diabetes, rheumatoid arthritis, or eye surgery, after refractive eye surgery.

In certain embodiments, the polymorphisms in the THBS1 gene are useful for better diagnosing existing dry eye disease in an individual, e.g. in combination with measurement of interleukin-1 beta expression levels. In such embodiments, the presence of an increased expression of interleukin-1 beta as compared to expression in a healthy individual together with the presence of at least one of the SNPS associated with dry eye is indicative of a diagnosis of dye eye disease.

It should be understood that a skilled artisan can also use other symptoms of dry eye disease to aid in diagnosis. Symptoms of dry eye disease include, e.g. stinging or burning of the eye; a sandy or gritty feeling as if something is in the eye; episodes of excess tears following very dry eye periods; a stringy discharge from the eye; pain and redness of the eye; episodes of blurred vision; heavy eyelids; inability to cry when emotionally stressed; uncomfortable contact lenses; a decreased tolerance of reading, working on the computer, or any activity that requires sustained visual attention; and eye fatigue.

When an individual is determined to have an increased risk of dry eye, using the methods described herein, a treatment regime can then be implemented. For example, administration of a dry eye therapeutic, and/or recommendations for self-treatment. Recommendations for self-treatment include, but are not limited to, a recommendation to wear glasses or sunglasses that fit close to the face (wrap around shades) or that have side shields can help slow tear evaporation from the eye surfaces; a recommended use of an air cleaner to filter dust and other particles helps prevent dry eyes or use of humidifier to add moisture to the air; recommended avoidance of dry conditions; recommended rest of eyes when performing activities that require eye use for long periods of time.

In certain embodiments, the individual is selected as having a condition associated with dry eye, for example, diabetes, rheumatoid arthritis, lupus, scleroderma, Sjogren's syndrome, thyroid disorders, vitamin A deficiency, or rheumatoid arthritis. In one embodiment, the individual is selected as being a candidate for eye surgery, e.g. refractive eye surgery, i.e. "an individual in need of refractive eye surgery." Refractive eye surgery is any eye surgery that is used to improve the refractive state of the eye and decrease or eliminate dependency on glasses or contact lenses. Accordingly, candidates for refractive eye surgery are those that are in need of lens correction. Candidates for refractive eye surgery also include those that suffer from common vision disorders such as myopia, hyperopia and astigmatism, as well as degenerative disorders like keratoconus.

Refractive eye surgery includes, but is not limited to, various methods of surgical remodeling of the cornea or cataract surgery. The most common methods of refractive eye surgery include the use of excimer lasers to reshape the curvature of the cornea.

Accordingly, the methods, systems, and assays described herein which allow determination of an increased risk for dry eye disease in an individual having a SNP1, SNP2, or SNP3 polymorphism in THBS1 can help prevent the development of dry eye in individuals having a condition associated with dry eye. The individual can be directed to a suitable treatment regime as a preventative for the development of dry eye. In one embodiment, e.g. when the individual is in need of refractive eye surgery, the treatment regime can be started before, during and/or after surgery as a preventative treatment.

A variety of approaches can be taken to treat dry eyes. For example, avoidance of exacerbating factors, tear stimulation and supplementation, increasing tear retention, eyelid cleansing and treatment of eye inflammation. Application of artificial tears every few hours can provide temporary relief. Inflammation occurring in response to tears film hypertonicity can be suppressed by mild topical steroids or with topical immunosuppressant such as cyclosporine. In addition change in diet may have an effect, consumption of dark-fleshed fish containing dietary omega-3 fatty acids is associated with a decreased incidence of dry eyes syndrome in women.

Examples of the tear substitution approach include the use of buffered, isotonic saline solutions, aqueous solutions containing water soluble polymers that render the solutions more viscous and thus less easily shed by the eye. Tear reconstitution is also performed by providing one or more components of the tear film such as phospholipids and oils. Phospholipid compositions have been shown to be useful in treating dry eye; see, e.g., McCulley and Shine, Tear film structure and dry eye, Contactologia, volume 20(4), pages 145-49 (1998); and Shine and McCulley, Keratoconjunctivitis sicca associated with meibomian secretion polar lipid abnormality, Archives of Ophthalmology, volume 116(7), pages 849-52 (1998).

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Possible pharmaceutical interventions (dry eye therapeutics) for the treatment of dry eye, include lubricating substances and/or immunosuppressant including, but not limited to: artificial tears; topical application of opioid antagonists (e.g. as described in U.S. Pat. No. 8,314,118); proteosome inhibitors (e.g. as described in U.S. Pat. No. 7,112,588); inhibitors of cytokine synthesis (e.g. as described in U.S. Pat. No. 7,026,296); inhibitors of NF-KappaB (e.g. as described in U.S. Pat. No. 6,696,456); inhibitors of PDE-IV (e.g. as described in U.S. Pat. No. 6,872,382); topical use of glycosides (e.g. as described in U.S. Pat. No. 7,223,737); agonists of adenosine receptor (e.g. as described in U.S. Pat. Application 2010/0222369); corticosteroid (e.g. as described in U.S. Pat. No. 6,153,607); inhibitors of acyl-coA synthase (e.g. as described in U.S. Pat. No. 6,645,994); as well as those pharmaceuticals described in U.S. Patent Nos: US 2012/0245090; U.S. Pat. No. 6,645,994; U.S. Pat. No. 8,314,118; US 2007/0265353; U.S. Pat. No. 7,112,588; US 2013/0045927; U.S. Pat. No. 5,266,381; U.S. Pat. No. 6,696,453; U.S. Pat. No. 6,013,259; U.S. Pat. No. 7,186,233; US 2010/0222369; U.S. Pat. No. 6,153,607; U.S. Pat. No. 6,645,978; U.S. Pat. No. 8,293,713; US 2004/0218139; U.S. Pat. No. 6,874,884; US 2003/0008854; v U.S. Pat. No. 7,235,556; US 2006/0189541; US 2010/0190734; US 2011/0301250; U.S. Pat. No. 6,254,893; U.S. Pat. No. 7,036,928; U.S. Pat. No. 5,830,913; U.S. Pat. No. 8,080,428; US 2005/0146353; US 2013/0336557; U.S. Pat. No. 5,981,607; U.S. Pat. No. 7,748,387; U.S. Pat. No. 7,745,461; U.S. Pat. No. 8,211,434; U.S. Pat. No. 7,923,471; U.S. Pat. No. 8,114,420; U.S. Pat. No. 8,569,367; U.S. Pat. No. 6,740,674; US 2011/0223169; US 2011/0223170; and US 2009/0098136; each of which are herein incorporated by reference in their entirety.

As used herein, the terms "treat" or "treatment" or "treating" refers to both therapeutic treatment and prophylactic (i.e. preventative) measures, wherein the object is to prevent or slow the development of the dry eye. Treatment is generally "effective" if one or more symptoms or clinical markers of dry eye are reduced. "Treatment" is not intended to include curing of disease, however treatment can prevent the onset of disease and reduce symptoms such that they are not detectable. For example, treatment is "effective" if the progression to dry eye, or chronic dry eye, is significantly reduced or prevented, i.e. prophylactic preventative treatment. Beneficial or desired clinical results include, but are not limited to, alleviation of one or more symptom(s), diminishment of extent of dry eye, stabilized (i.e., not worsening) state of dry eye or disease, delay or slowing of dry eye or disease progression, amelioration or palliation of the dry eye or disease state, and remission. Those in need of treatment include those already diagnosed with dry eye, as well as those likely to develop dry eye, e.g. because they are undergoing eye surgery and also have a SNP disclosed herein that is associated with dry eye; or have a disease associated with dry eye, such as diabetes or rheumatoid arthritis, among others, and also have one or more SNPs associated with dry eye. As described, symptoms of dry eye disease include, but are not limited to, inflammation, stinging or burning of the eye; a sandy or gritty feeling as if something is in the eye; episodes of excess tears following very dry eye periods; a stringy discharge from the eye; pain and redness of the eye; episodes of blurred vision; heavy eyelids; inability to cry when emotionally stressed; uncomfortable contact lenses; a decreased tolerance of reading, working on the computer, or any activity that requires sustained visual attention; and eye fatigue. One of skill in the art is well versed in assessing such symptoms.

The term "effective amount" as used herein refers to the amount of a pharmaceutical composition, to decrease at least one or more symptoms of dry eye, and relates to a sufficient amount of pharmacological composition to provide the desired effect. The phrase "therapeutically effective amount" and "pharmaceutically effective amount" are used interchangeably and as used herein means a sufficient amount of the composition to treat dry eye at a reasonable benefit/risk ratio applicable to any medical treatment. The term "therapeutically effective amount" therefore refers to an amount of the composition that is sufficient to effect a therapeutically or prophylactically significant reduction in a symptom or clinical marker associated with dry eye.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90% in a measured parameter as compared to a control or non-treated subject. Measured or measurable parameters include clinically detectable markers of disease, for example, elevated or depressed levels of a biological marker, as well as parameters related to a clinically accepted scale of symptoms or markers for a disease or disorder. It should be understood, however, that the total daily usage of the compositions and formulations as disclosed herein will be decided by the attending physician within the scope of sound medical judgment. The exact amount required will vary depending on factors such as age, weight and severity of dry eye disease being treated.

The dry eye therapeutic may be administered by any suitable means that results in a concentration suitable for treatment of dry eye. The compound suitable for treatment of dry eye may be contained in any appropriate amount in any pharmaceutically acceptable carrier substance, and is generally present in an amount of 1-95% by weight of the total weight of the composition. The composition may be provided in a dosage form that is suitable for the oral, parenteral (e.g., intravenously or intramuscularly), intraperitoneal, rectal, cutaneous, nasal, vaginal, inhalant, skin (patch), or ocular administration route. Thus, the composition may be in the form of, e.g., eye drops, tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions suitable for treatment of dry eye may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

The actual amount of the therapeutic compound of this invention, i.e., the active ingredient, will depend upon numerous factors such as the severity of the dry eye or disease to be treated, the age and relative health of the subject, the potency of the compound used, the route and form of administration, and other factors. Therapeutically effective amounts of therapeutic compounds may range from, for example, approximately 0.01-50 mg per kilogram body weight of the recipient per day; preferably about 0.1-20 mg/kg/day. Thus, as an example, for administration to a 70 kg person, the dosage range would most preferably be about 7 mg to 1.4 g per day. The choice of formulation depends on various factors such as the mode of drug administration (e.g., for oral administration, formulations in the form of tablets, pills, or capsules are preferred) and the bioavailability of the drug substance.

Pharmaceutical compositions are comprised of, in general, a therapeutic compound in combination with at least one pharmaceutically acceptable excipient. Acceptable excipients are non-toxic, aid administration, and do not adversely affect the therapeutic benefit of the therapeutic compound. Such excipients may be any solid, liquid, semi-solid or, in the case of an aerosol composition, gaseous excipient that is generally available to one skilled in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

Systems and Computer Readable Media

Embodiments of the invention also provide for systems (and computer readable media for causing computer systems) to perform a method for determining whether an individual has a pre-disposition (an increased risk) for dry eye based on sequence information of the THBS1 gene or protein.

A system for analyzing a biological sample is provided. The system comprises: a) a determination module configured to receive a biological sample or data of a biological sample and to determine sequence information, wherein the sequence information comprises a sequence of a coding or non-coding region of Thrombospondin-1 (THBS1) gene, or Thrombospondin-1 protein; b) a storage device configured to store sequence information from the determination module; c) a comparison module adapted to compare the sequence information stored on the storage device with reference data, and to provide a comparison result, wherein the comparison result identifies the presence or absence of a single nucleotide polymorphism (DNA), or corresponding amino acid change (protein) in THBS1 gene or protein, wherein the SNP is selected from the group consisting of the presence of a cytosine "C" allele at position 42 of SEQ ID NO: 1, or its complement thereof; the presence of a thymine "T" allele at position 7079 of SEQ ID NO: 1, or its complement thereof; and the presence of a guanine "G" allele at position 7543 of SEQ ID NO: 1, or its complement thereof; and wherein the SNP is indicative of an increased risk for dry eye; and d) a display module for displaying a content based in part on the comparison result for the user, wherein the content is a signal indicative of an increased risk for dry eye, or a signal indicative of lack of an increased risk for dry eye and dry eye-related disease. In one embodiment the signal indicates that the individual is in need of treatment for dry eye (e.g. pre- or post-refractive eye surgery) (i.e. the individual has an increased risk for development of dry eye) or the signal indicates that the individual is not in need for treatment of dry eye (does not have an increased risk) (e.g. pre and/or post refractive eye surgery).

The invention further provides for a computer readable medium having computer readable instructions recorded thereon to define software modules including a comparison module and a display module for implementing a method on a computer. The method comprises a) comparing with the comparison module the data stored on a storage device with reference data to provide a comparison result, wherein the comparison result identifies the presence or absence of a single nucleotide polymorphism (SNP), or corresponding amino acid changes in THBS1 gene or protein, wherein the SNP is selected from the group consisting of: the presence of a cytosine "C" allele at position 42 of SEQ ID NO: 1, or its complement thereof; the presence of a thymine "T" allele at position 7079 of SEQ ID NO: 1, or its complement thereof; and the presence of a guanine "G" allele at position 7543 of SEQ ID NO: 1, or its complement thereof; and b) displaying a content based in part on the comparison result for the user, wherein the content is a signal indicative of an increased risk of dry eye and dry eye.

Figure 13:
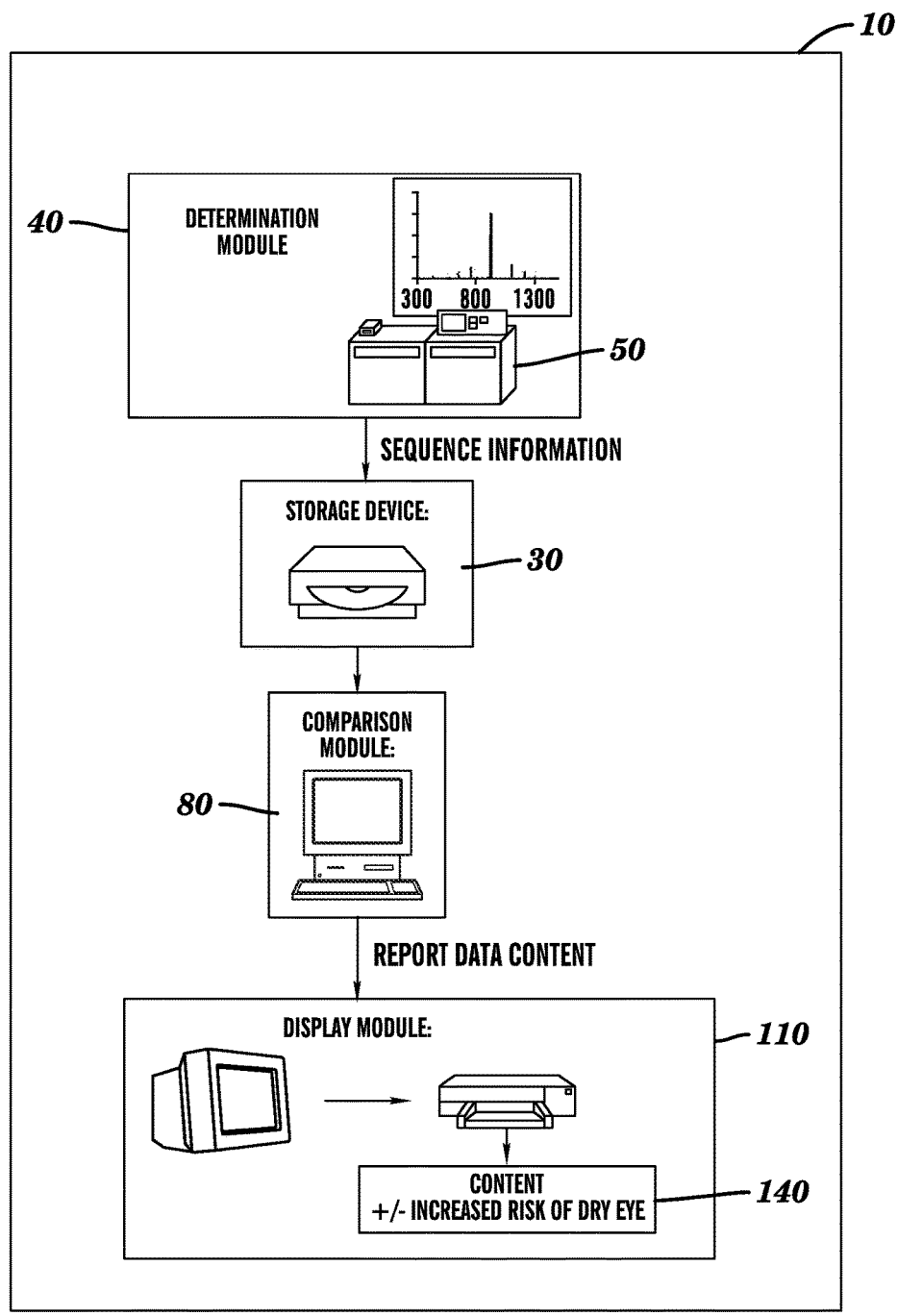
FIG. 13 shows a block diagram showing an example of a system for determining an increased risk for development of dry eye in an individual.
Figure 14:
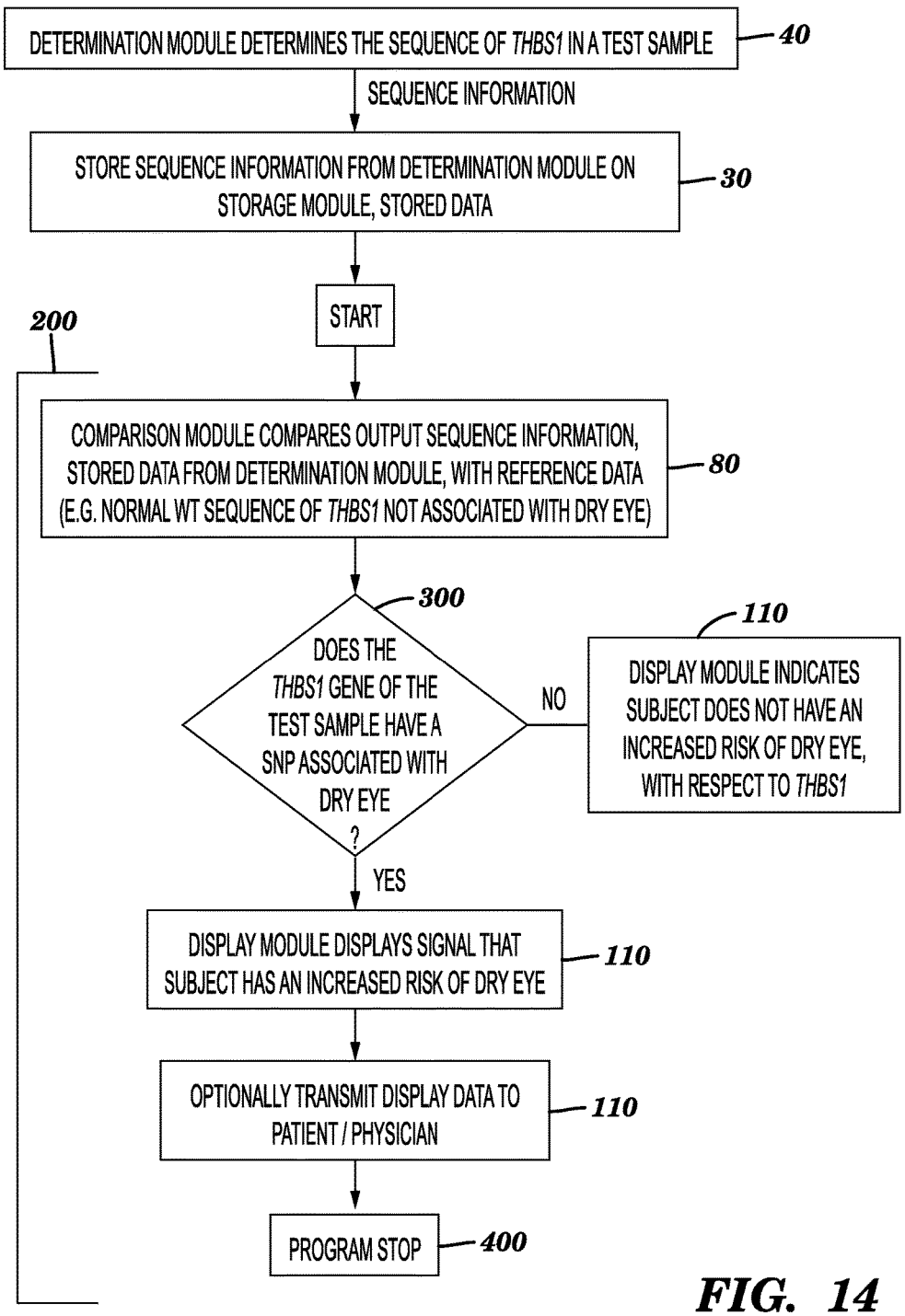
FIG. 14 shows a block diagram showing exemplary instructions on a computer readable medium for determining an increased risk for the development of dry eye in an individual.

Embodiments of the invention have been described through functional modules, which are defined by computer executable instructions recorded on computer readable media and which cause a computer to perform method steps when executed, See FIG. 13 and FIG. 14. The modules have been segregated by function for the sake of clarity. However, it should be understood that the modules need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable media can be any available tangible media that can be accessed by a computer. Computer readable media includes volatile and nonvolatile, removable and non-removable tangible media implemented in any method or technology for storage of information such as computer readable instructions, data structures, program modules or other data. Computer readable media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media, or computer readable medium 200, may define instructions, for example, as part of one or more programs, that, as a result of being executed by a computer, instruct the computer to perform one or more of the functions described herein (e.g., in relation to system 10, or computer readable medium 200), and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of system 10, or computer readable medium 200 described herein, may be distributed across one or more of such components, and may be in transition there between.

The computer-readable media may be transportable such that the instructions stored thereon can be loaded onto any computer resource to implement the aspects of the present invention discussed herein. In addition, it should be appreciated that the instructions stored on the computer readable media, or computer-readable medium 200, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages. Basic computational biology methods are known to those of ordinary skill in the art and are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The functional modules of certain embodiments of the invention include a determination module, a storage device, a comparison module and a display module See FIG. 13 and FIG. 14. The functional modules can be executed on one, or multiple, computers, or by using one, or multiple, computer networks. The determination module 40 has computer executable instructions to provide sequence information in computer readable form. As used herein, "sequence information" refers to any nucleotide and/or amino acid sequence, including but not limited to full-length nucleotide and/or amino acid sequences, partial nucleotide and/or amino acid sequences, or mutated sequences. Moreover, information "related to" the sequence information includes detection of the presence or absence of a sequence (e.g., detection of a mutation or deletion), determination of the concentration of a sequence in the sample (e.g., amino acid sequence expression levels, or nucleotide (RNA or DNA) expression levels), and the like. The term "sequence information" is intended to include the presence or absence of post-translational modifications (e.g. phosphorylation, glycosylation, summylation, farnesylation, and the like).

As an example, determination modules 40 for determining sequence information may include known systems for automated sequence analysis including but not limited to Hitachi FMBIO® and Hitachi FMBIO® II Fluorescent Scanners (available from Hitachi Genetic Systems, Alameda, Calif.); Spectrumedix® SCE 9610 Fully Automated 96-Capillary Electrophoresis Genetic Analysis Systems (available from SpectruMedix LLC, State College, Pa.); ABI PRISM® 377 DNA Sequencer, ABI® 373 DNA Sequencer, ABI PRISM® 310 Genetic Analyzer, ABI PRISM® 3100 Genetic Analyzer, and ABI PRISM® 3700 DNA Analyzer (available from Applied Biosystems, Foster City, Calif.); Molecular Dynamics FluorImager™ 575, SI Fluorescent Scanners, and Molecular Dynamics FluorImager™ 595 Fluorescent Scanners (available from Amersham Biosciences UK Limited, Little Chalfont, Buckinghamshire, England); GenomyxSC™ DNA Sequencing System (available from Genomyx Corporation (Foster City, Calif.); and Pharmacia ALF™ DNA Sequencer and Pharmacia ALFexpress™ (available from Amersham Biosciences UK Limited, Little Chalfont, Buckinghamshire, England).

Alternative methods for determining sequence information, i.e. determination modules 40, include systems for protein and DNA analysis. For example, mass spectrometry systems including Matrix Assisted Laser Desorption Ionization-Time of Flight (MALDI-TOF) systems and SELDI-TOF-MS ProteinChip array profiling systems; systems for analyzing gene expression data (see, for example, published U.S. Patent Application, Pub. No. U.S. 2003/0194711); systems for array based expression analysis: e.g., HT array systems and cartridge array systems such as GeneChip® AutoLoader, Complete GeneChip® Instrument System, GeneChip® Fluidics Station 450, GeneChip® Hybridization Oven 645, GeneChip® QC Toolbox Software Kit, GeneChip® Scanner 3000 7G plus Targeted Genotyping System, GeneChip® Scanner 3000 7G Whole-Genome Association System, GeneTitan™ Instrument, and GeneChip® Array Station (each available from Affymetrix, Santa Clara, Calif.); automated ELISA systems (e.g., DSX® or DK® (available from Dynax, Chantilly, Va.) or the Triturus® (available from Grifols USA, Los Angeles, Calif.), The Mago® Plus (available from Diamedix Corporation, Miami, Fla.); Densitometers (e.g. X-Rite-508-Spectro Densitometer® (available from RP Imaging™, Tucson, Ariz.), The HYRYS™ 2 HIT densitometer (available from Sebia Electrophoresis, Norcross, Ga.); automated Fluorescence insitu hybridization systems (see for example, U.S. Pat. No. 6,136,540); 2D gel imaging systems coupled with 2-D imaging software; microplate readers; Fluorescence activated cell sorters (FACS) (e.g. Flow Cytometer FACSVantage SE, (available from Becton Dickinson, Franklin Lakes, N.J.); and radio isotope analyzers (e.g. scintillation counters).

The sequence information determined in the determination module can be read by the storage device 30. As used herein the "storage device" 30 is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices 30 also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device 30 is adapted or configured for having recorded thereon sequence information or expression level information. Such information may be provided in digital form that can be transmitted and read electronically, e.g., via the Internet, on diskette, via USB (universal serial bus) or via any other suitable mode of communication.

As used herein, "expression level information" refers to any nucleotide and/or amino acid expression level information, including but not limited to full-length nucleotide and/or amino acid sequences, partial nucleotide and/or amino acid sequences, or mutated sequences. Moreover, information "related to" the expression level information includes detection of the presence or absence of a sequence (e.g., presence or absence of an amino acid sequence, nucleotide sequence, or post translational modification), determination of the concentration of a sequence in the sample (e.g., amino acid sequence levels, or nucleotide (RNA or DNA) expression levels, or level of post translational modification), and the like. In certain embodiments. The systems and media described herein further include expression level information (reference levels and detection levels of interleukin-1 beta and/or thrombospondin-1 protein.

As used herein, "stored" refers to a process for encoding information on the storage device 30. Those skilled in the art can readily adopt any of the presently known methods for recording information on known media to generate manufactures comprising the sequence information or expression level information.

A variety of software programs and formats can be used to store the sequence information or expression level information on the storage device. Any number of data processor structuring formats (e.g., text file or database) can be employed to obtain or create a medium having recorded thereon the sequence information or expression level information.

By providing sequence information or expression level information in computer-readable form, one can use the sequence information or expression level information in readable form in the comparison module 80 to compare a specific sequence or expression profile with the reference data within the storage device 30. For example, search programs can be used to identify fragments or regions of the sequences that match a particular sequence (reference data, e.g., sequence information obtained from a control sample) or direct comparison of the determined expression level can be compared to the reference data expression level (e.g., sequence information obtained from a control sample). The comparison made in computer-readable form provides a computer readable comparison result which can be processed by a variety of means. Content 140 based on the comparison result can be retrieved from the comparison module 80 to indicate an increased likelihood of dry eye, or dry eye related disorder.

In one embodiment the reference data stored in the storage device 30 to be read by the comparison module 80 is sequence information data obtained from a control biological sample of the same type as the biological sample to be tested. Alternatively, the reference data are a database, e.g., a part of the entire genome sequence of an organism, or a protein family of sequences, or an expression level profile (RNA, protein or peptide). In one embodiment the reference data are sequence information or expression level profiles that are indicative of dry eye.

In one embodiment, the reference data are one or more reference polynucleotide, or polypeptide sequences derived from sequences selected from the group consisting of SEQ ID NO: 1, or sequences derived from sequences of the following genebank accession numbers: NC_000015.9; NC_000019.10 39581097..393974767 (SEQ ID NO: 1), NM_003246.2:c.1, NP_003237.2, NT_010194.17 (e.g. normal control reference data). In one embodiment, the reference data are electronically or digitally recorded and annotated from databases including, but not limited to GenBank (NCBI) protein and DNA databases such as genome, ESTs, SNPS, Traces, Celara, Ventor Reads, Watson reads, HGTS, and the like; Swiss Institute of Bioinformatics databases, such as ENZYME, PROSITE, SWISS-2DPAGE, Swiss-Prot and TrEMBL databases; the Melanie software package or the ExPASy WWW server, and the like; the SWISS-MODEL, Swiss-Shop and other network-based computational tools; the Comprehensive Microbial Resource database (available from The Institute of Genomic Research). The resulting information can be stored in a relational data base that may be employed to determine homologies between the reference data or genes or proteins within and among genomes. For example the reference snp data may be stored wherein a match upon comparison is a positive result. The reference sequence representative of SNPS described herein include, e.g. SNP 1 reference sequences include, but are not limited to, rs1478604 [*Homo sapiens*], SEQ ID NO: 1 having the presence of a cytosine "C" allele at position 42 of SEQ ID NO: 1, or its complement thereof; rs1478604 A>G in 5' untranslated region; −138T>C; 10663878T>C; and 39873321T>C; Genebank Accessions: NC_000015.9: g.39873321T>C; NM_003246.2:c.−138T>C; NT_010194.17:g.10663878T>C. SNP2 reference sequences include, but are not limited to, the presence of a thymine "T" allele at position 7079 of SEQ ID NO: 1, or its complement thereof; accession rs2228261 at 15:39880358 in THBS1; NC_000015.9:g.39880358C>T, NM_003246.2:c.1410C>T, NP_003237.2:p.Asn470, NT_010194.17:g.10670915C>T. SNP3 reference sequences include, but are not limited to, the presence of a guanine "G" allele at position 7543 of SEQ ID NO: 1, or its complement thereof; rs2292305 at 15:39880822 in THBS1; NC_000015.9:g.39880822A>G, NM_003246.2:c.1567A>G, NP_003237.2:p.Thr523Ala, NT_010194.17:g.10671379A>G.

The "comparison module" 80 can use a variety of available software programs and formats for the comparison operative to compare sequence information determined in the determination module 40 to reference data. In one embodiment, the comparison module 80 is configured to use pattern recognition techniques to compare sequence information from one or more entries to one or more reference data patterns. The comparison module 80 may be configured using existing commercially-available or freely-available software for comparing patterns, and may be optimized for particular data comparisons that are conducted. The comparison module 80 provides computer readable information related to the sequence information that can include, for example, detection of the presence or absence of a sequence (e.g., detection of a mutation or deletion (protein or DNA), information regarding distinct alleles, detection of post-translational modification, or omission or repetition of sequences); determination of the concentration of a sequence in the sample (e.g., amino acid sequence/protein expression levels, or nucleotide (RNA or DNA) expression levels, or levels of post-translational modification), or determination of an expression profile.

In one embodiment, the comparison module 80 permits the prediction of protein sequences from polynucleotide sequences, permits prediction of open reading frames (ORF), or permits prediction of homologous sequence information in comparison to reference data, i.e., homologous protein domains, homologous DNA or RNA sequences, or homologous exons and/or introns.

In one embodiment, the comparison module 80 uses sequence information alignment programs such as BLAST (Basic Local Alignment Search Tool) or FAST (using the Smith-Waternan algorithm) may be employed individually or in combination. These algorithms determine the alignment between similar regions of sequences and a percent identity between sequences. For example, alignment may be calculated by matching, bases-by-base or amino acid-by amino-acid.

The comparison module 80, or any other module of the invention, may include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executable will include embedded SQL statements. In addition, the World Wide Web application may include a configuration file which contains pointers and addresses to the various software entities that comprise the server as well as the various external and internal databases which must be accessed to service user requests. The Configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

In one embodiment, the comparison module 80 performs comparisons with mass-spectometry spectra, for example comparisons of peptide fragment sequence information can be carried out using spectra processed in MATLB with script called "Qcealign" (see for example WO2007/022248, herein incorporated by reference) and "Qpeaks" (Spectrum Square Associates, Ithaca, N.Y.), or Ciphergen Peaks 2.1™ software. The processed spectra can then be aligned using alignment algorithms that align sample data to the control data using minimum entropy algorithm by taking baseline corrected data (see for example WIPO Publication WO2007/022248, herein incorporated by reference). The comparison result can be further processed by calculating ratios. Protein expression profiles can be discerned.

In one embodiment, computational algorithms are used in the comparison module 80 such as expectation-maximization (EM), subtraction and PHASE are used in methods for statistical estimation of haplotypes (see, e.g., Clark, A. G. *Mol Biol Evol* 7:111-22 (1990); Stephens, M., Smith, N.J. & Donnelly, P. *Am J Hum Genet* 68:978-89 (2001); Templeton, A. R., Sing, C. F., Kessling, A. & Humphries, *Genetics* 120:1145-54 (1988)).

Various algorithms are available which are useful for comparing data and identifying the predictive gene signatures. For example, algorithms such as those identified in Xu et al., *Physiol. Genomics* 11:11-20 (2002). There are numerous software available for detection of SNPs and polymorphisms that can be used in the comparison module, including, but not limited to: HaploSNPer, a web-based program for detecting SNPs and alleles in user-specified input sequences from both diploid and polyploid species (available on the world-wide web at bioinformatics.nl/tools/haplosnper/; see also Tang et al., *BMC Genetics* 9:23 (2008)); Polybayes, a tool for SNP discovery in redundant DNA sequences (Marth, G T., et al., *Nature Genetics* 23(4):452-6 (1999); SSAHA-SNP, a polymorphism detection tool that uses the SSAHA alignment algorithm (available from Wellcome Trust Sanger Institute, Cambridge, United Kingdom, see also Ning Z., et al., *Genome Research* 11(10):1725-9 (2001)); Polyphred, A SNP discovery package built on phred, phrap, and consed tools (available on the world-wide web, see Nickerson, D A et al., *Nucleic Acids Research* 25(14):2745-51 (1997)); NovoSNP, a graphical Java-based program (PC/Mac/Linux) to identify SNPs and indels (available on the world-wide web, see Weckx, S. et al., *Genome Research* 15(3):436-442 (2005)); SNPdetector™, for automated identification of SNPs and mutations in fluorescence-based resequencing reads (available from Affymetrix, Santa Clara, Calif.), see also Zhang et al. *PLoS Comput Biol* (5):e53 (2005). SNPdetector runs on Unix/Linux platform and is available publicly; Affymetrix (Santa Clara, Calif.) has multiple data analysis software that can be used, for example Genotyping Console™ Software, GeneChip® Sequence Analysis Software (GSEQ), GeneChip® Targeted Genotyping Analysis Software (GTGS) and Expression Console™ Software.

In one embodiment, the comparison module 80 compares gene expression profiles. For example, detection of gene expression profiles can be determined using Affymetrix Microarray Suite software version 5.0 (MAS 5.0) (available from Affymetrix, Santa Clara, Calif.) to analyze the relative abundance of a gene or genes on the basis of the intensity of the signal from probe sets, and the MAS 5.0 data files can be transferred into a database and analyzed with Microsoft Excel and GeneSpring 6.0 software (available from Agilent Technologies, Santa Clara, Calif.). The detection algorithm of MAS 5.0 software can be used to obtain a comprehensive overview of how many transcripts are detected in given samples and allows a comparative analysis of two or more microarray data sets.

In one embodiment, the comparison module 80 compares protein expression profiles. Any available comparison software can be used, including but not limited to, the Ciphergen Express (CE) and Biomarker Patterns Software (BPS) package (available from Ciphergen Biosystems, Inc., Freemont, Calif.). Comparative analysis can be done with protein chip system software (e.g., The Proteinchip Suite (available from Bio-Rad Laboratories, Hercules, Calif.). Algorithms for identifying expression profiles can include the use of optimization algorithms such as the mean variance algorithm (e.g. JMP Genomics algorithm available from JMP Software Cary, N.C.).

In one embodiment of the invention, pattern comparison software is used to determine whether patterns of expression or mutations are indicative of a disease.

The comparison module 80 provides computer readable comparison result that can be processed in computer readable form by predefined criteria, or criteria defined by a user, to provide a content based in part on the comparison result that may be stored and output as requested by a user using a display module 110. The display module 110 enables display of a content 140 based in part on the comparison result for the user, wherein the content 140 is a signal indicative of increased risk for dry eye. Such signal, can be for example, a display of content 140 indicative of the presence or absence of increased risk for dry eye or dry eye related-disease on a computer monitor, a printed page of content 140 indicating the presence or absence of increased risk for dry eye from a printer, or a light or sound indicative of the presence or absence of increased risk for dry eye.

The content 140 based on the comparison result may include an expression profile of one or more proteins, or an expression profile of one or more genes. In one embodiment, the content 140 based on the comparison includes a sequence of a particular gene or protein and a determination of the presence of one or more mutations, or specific post-translational modification. In one embodiment, the content 140 based on the comparison result is merely a signal indicative of the presence or absence of an increased risk of dry eye.

In one embodiment of the invention, the content 140 based on the comparison result is displayed a on a computer monitor. In one embodiment of the invention, the content 140 based on the comparison result is displayed through printable media. The display module 110 can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content 140 based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces. The requests so formulated with the user's Web browser are transmitted to a Web application which formats them to produce a query that can be employed to extract the pertinent information related to the sequence information, e.g., display of an indication of the presence or absence of mutation or deletion (DNA or protein); display of expression levels of an amino acid sequence (protein); display of nucleotide (RNA or DNA) expression levels; display of expression, SNP, or mutation profiles, or haplotypes, or display of information based thereon. In one embodiment, the sequence information of the reference sample data is also displayed.

In one embodiment, the display module 110 displays the comparison result sequences and whether the comparison result is indicative of a disease, e.g., sequence having the SNPs identified herein as indicative of an increased risk in dry eye or disease.

In one embodiment, the content 140 based on the comparison result that is displayed is a signal (e.g. positive or negative signal) indicative of the presence or absence of an increased risk for dry eye or dry eye related-disease, thus only a positive or negative indication may be displayed.

Embodiments of the present invention therefore provide for systems 10 (and computer readable medium 200 for causing computer systems) to perform methods for determining whether an individual has dry eye or dry eye disorder or a pre-disposition, for dry eye or dry eye-related disease based on expression profiles or sequence information.

System 10, and computer readable medium 200, are merely an illustrative embodiments of the invention for performing methods of determining whether an individual has a specific disease or disorder or a pre-disposition, for a specific disease or disorder based on expression profiles or sequence information, and is not intended to limit the scope of the invention. Variations of system 10, and computer readable medium 200, are possible and are intended to fall within the scope of the invention.

The modules of the machine, or used in the computer readable medium, may assume numerous configurations. For example, function may be provided on a single machine or distributed over multiple machines Definitions For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

The term "nucleic acid" is well known in the art. A "nucleic acid" as used herein will generally refer to a molecule (i.e., strand) of DNA, RNA or a derivative or analog thereof, comprising a nucleobase. A nucleobase includes, for example, a naturally occurring purine or pyrimidine base found in DNA (e.g. an adenine "A," a guanine "G" a thymine "T" or a cytosine "C") or RNA (e.g. an A, a G. an uracil "U" or a C). The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length.

The terms "polypeptide", "peptide", "oligopeptide", "polypeptide", "gene product", "expression product" and "protein" are used interchangeably herein to refer to a polymer or oligomer of consecutive amino acid residues.

A "gene" refers to coding sequence of a gene product, as well as non-coding regions of the gene product, including 5'UTR and 3'UTR regions, introns and the promoter of the gene product. In addition to the THBS1 gene, other regulatory regions such as the promoter and enhancers for THBS1 are contemplated as nucleic acids for use with compositions and methods of the claimed invention. Thus, a nucleic acid may encompass a double-stranded molecule or a double-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "is." The term "gene" refers to the segment of DNA involved in producing a polypeptide chain, it includes regions preceding and following the coding region as well as intervening sequences (introns) between individual coding segments (exons). A "promoter" is a region of a nucleic acid sequence at which initiation and rate of transcription are controlled. It may contain elements at which regulatory proteins and molecules may bind, such as RNA polymerase and other transcription factors, to initiate the specific transcription of a nucleic acid sequence. The term "enhancer" refers to a cis-acting regulatory sequence involved in the transcriptional activation of a nucleic acid sequence. An enhancer can function in either orientation and may be upstream or downstream of the promoter.

The term "exon" as used herein refers to the normal sense of the term as meaning a segment of nucleic acid molecules, usually DNA, that encodes part of or all of an expressed protein.

The term "non-coding" refers to sequences of nucleic acid molecules that do not encode part or all of an expressed protein. Non-coding sequences include but are not limited to introns, promoter regions, 3' untranslated regions (3'UTR), and 5' untranslated regions (5'UTR).

The term "coding region" as used herein, refers to a portion of the nucleic acid, which is transcribed and translated in a sequence-specific manner to produce into a particular polypeptide or protein when placed under the control of appropriate regulatory sequences. The coding region is said to encode such a polypeptide or protein.

With reference to nucleic acids of the invention, the term "isolated nucleic acid" or "isolated polynucleotide" is sometimes used. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

The term "oligonucleotide," as used herein refers to primers and probes of the present invention, and is defined as a nucleic acid molecule comprised of at least two or more ribo- or deoxyribonucleotides. The exact size of the oligonucleotide will depend on various factors and on the particular application and use of the oligonucleotide. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and the method used. For example, for diagnostic applications, depending on the complexity of the target sequence, an oligonucleotide probe typically contains 15-25 or more nucleotides, although it may contain fewer nucleotides. The probes as disclosed herein are selected to be substantially complementary to different strands of a particular target nucleic acid sequence. This means that the probes must be sufficiently complementary so as to be able to "specifically hybridize" or anneal with their respective target strands. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarily with the sequence of the target nucleic acid to anneal therewith specifically.

In the context of this invention, the term "probe" refers to a molecule which can detectably distinguish between target molecules differing in structure (e.g. nucleic acid or protein sequence). Detection can be accomplished in a variety of different ways depending on the type of probe used and the type of target molecule. Thus, for example, detection may be based on discrimination on detection of specific binding. Examples of such specific binding include antibody binding and nucleic acid, antibody binding to protein, nucleic acid binding to nucleic acid, or aptamer binding to protein or nucleic acid. Thus, for example, probes can include enzyme substrates, antibodies and antibody fragments, and preferably nucleic acid hybridization probes. The nucleic acid hybridization probes can be The term "specifically hybridize" refers to the association between two single-stranded nucleic acid molecules of sufficient complementary sequence to permit such hybridization under pre-determined conditions generally used in the art (sometimes the sequences are referred to as "substantially complementary"). In particular, the term specifically hybridize also refers to hybridization of an oligonucleotide with a substantially complementary sequence as compared to non-complementary sequence.

The term "specifically" as used herein with reference to a probe which is used to specifically detect a sequence difference, refers to a probe that identifies a particular sequence difference based on exclusive hybridization to the sequence difference under stringent hybridization conditions and/or on exclusive amplification or replication of the sequence difference.

In its broadest sense, the term "substantially" as used herein in respect to "substantially complementary", or when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, at least 70%, at least 80% or 85%, at least 90%, at least 93%, at least 95% or 96%, at least 97% or 98%, at least 99% or 100% (the later being equivalent to the term "identical" in this context). For example, identity is assessed over a length of at least 10 nucleotides, or at least 11, 12, 13, 14, 15, 16, 17, 18, 19, 20, 21, 22 or up to 50 nucleotides of the entire length of the nucleic acid sequence to said reference sequence (if not specified otherwise below). Sequence comparisons can be carried out using default GAP analysis with the University of Wisconsin GCG, SEQWEB application of GAP, based on the algorithm of Needleman and Wunsch (Needleman and Wunsch (1970) J Mol. Biol. 48: 443-453). A nucleotide sequence "substantially complementary" to a reference nucleotide sequence hybridizes to the reference nucleotide sequence under medium stringency conditions. In one embodiment, under high stringency conditions.

"Homologues" of a specific nucleotide sequence include nucleotide sequences that encode an amino acid sequence that is at least 24% identical, at least 35% identical, at least 50% identical, at least 65% identical to the reference amino acid sequence, as measured using the parameters described above, wherein the amino acid sequence encoded by the homolog has the same biological activity as the protein encoded by the specific nucleotide. The term "substantially non-identical" refers to a nucleotide sequence that does not hybridize to the nucleic acid sequence under stringent conditions.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

A "normal" or "healthy individual", or "control group" refers to individuals that do not have dry eye or an dry eye-related disorder who are preferably of similar age and race.

The terms "variant", "variance", "mutation" or "polymorphism" are used interchangeably herein, and refer to a difference in nucleic acid sequence among members if a population of individuals. Polymorphisms can sometimes be referred to as "single nucleotide polymorphism" or "SNP" when they vary at a single nucleotide. In some embodiments, polymorphisms can be synonymous or no synonymous. Synonymous polymorphisms when present in the coding region or non-coding region typically do not result in an amino acid change, but can result in altered mRNA stability or altered alternative splice sites. Nonsynonymous polymorphism, when present in the coding region, can result in the alteration of one or more codons resulting in an amino acid replacement in the amino acid chain. Such mutations and polymorphisms may be either heterozygous or homozygous within an individual. Homozygous individuals have identical alleles at one or more corresponding loci on homologous chromosomes, while heterozygous individuals have two different alleles at one or more corresponding loci on homologous chromosomes. A polymorphism is thus said to be "allelic," in that, due to the existence of the polymorphism, some members of a species carry a gene with one sequence (e.g., the normal or wild-type "allele"), whereas other members may have an altered sequence (e.g., the variant or, mutant "allele").

The term a "polymorphic gene" refers to a gene having at least one polymorphic region.

The term "genotype" refers to the specific allelic composition of an entire cell or a certain gene, whereas the term "phenotype" refers to the detectable outward manifestations of a specific genotype.

The term "allele", as used herein, refers to one member of a pair of different forms of a gene. As used herein alleles refer to coding and to non-coding sequences. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The term 'effective amount' as used herein refers to the amount of therapeutic agent of pharmaceutical composition to alleviate at least some of the symptoms of dry eye or disease.

The term "biological sample" as used herein, refers to a cell or population of cells or a quantity of tissue or fluid from a subject. Often, a "biological sample" will contain cells from the animal, but the term can also refer to non-cellular biological material, such as non-cellular fractions of blood, saliva, or urine, eye CCI, that can be used to measure gene expression levels. Biological samples include, but are not limited to, tissue biopsies, scrapes (e.g. buccal scrapes), whole blood, plasma, serum, urine, saliva, cell culture, or cerebrospinal fluid. The sample can be obtained by removing a sample from a subject, but can also be accomplished by using previously isolated cells (e.g. isolated by another person), or by performing the methods of the invention in vivo.

As used herein the terms, "individual", "subject", "patient", are used interchangeably and are intended to include humans and mammals.

As used herein, an "amplified polynucleotide" of the invention is a SNP-containing nucleic acid molecule whose amount has been increased at least two fold by any nucleic acid amplification method performed in vitro as compared to its starting amount in a test sample. In other preferred embodiments, an amplified polynucleotide is the result of at least ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified genomic DNA, but the precise amount of amplification needed for an assay depends on the sensitivity of the subsequent detection method used. In some embodiments described herein, the assay comprise detection of SNP1 SNP2 or SNP3 in an amplified polynucleotide of nucleic acid in a biological sample taken from an individual.

Generally, an amplified polynucleotide is at least about 16 nucleotides in length. More typically, an amplified polynucleotide is at least about 20 nucleotides in length. In a preferred embodiment of the invention, an amplified polynucleotide is at least about 30 nucleotides in length. In a more preferred embodiment of the invention, an amplified polynucleotide is at least about 32, 40, 45, 50, or 60 nucleotides in length. In yet another preferred embodiment of the invention, an amplified polynucleotide is at least about 100, 200, or 300 nucleotides in length. While the total length of an amplified polynucleotide of the invention can be as long as an exon, an intron or the entire gene where the SNP of interest resides, an amplified product is typically no greater than about 1,000 nucleotides in length (although certain amplification methods may generate amplified products greater than 1000 nucleotides in length). More preferably, an amplified polynucleotide is not greater than about 600 nucleotides in length. It is understood that irrespective of the length of an amplified polynucleotide, a SNP of interest may be located anywhere along its sequence.

Embodiments of the invention provide isolated nucleic acid molecules that comprise, consist of, or consist essentially of one or more polynucleotide sequences that contain one or more SNPs disclosed herein, complements thereof, and SNP-containing fragments thereof. These isolated nucleic acid molecules can be used, for example, as probes to detect SNP1, SNP2, or SNP3 as described herein.

Those skilled in the art will readily recognize that nucleic acid molecules described herein may be double-stranded molecules and that reference to a particular site on one strand refers, as well, to the corresponding site on a complementary strand. In defining a SNP position, SNP allele, or nucleotide sequence, reference to an adenine, a thymine (uridine), a cytosine, or a guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular SNP position, SNP allele, or nucleotide sequence. Probes and primers, may be designed to hybridize to either strand and SNP genotyping methods disclosed herein may generally target either strand. Throughout the specification, in identifying a SNP position, reference is generally made to the protein-encoding strand, only for the purpose of convenience.

References to variant peptides, polypeptides, or proteins of the present invention include peptides, polypeptides, proteins, or fragments thereof, that contain at least one amino acid residue that differs from the corresponding amino acid sequence of the art-known peptide/polypeptide/protein (the art-known protein may be interchangeably referred to as the "wild-type", "reference", or "normal" protein). Such variant peptides/polypeptides/proteins can result from a codon change caused by a nonsynonymous nucleotide substitution at a protein-coding SNP position (i.e., a missense mutation) disclosed by the present invention. Variant peptides/polypeptides/proteins of the present invention can also result from a nonsense mutation, i.e. a SNP that creates a premature stop codon, a SNP that generates a read-through mutation by abolishing a stop codon, or due to any SNP disclosed by the present invention that otherwise alters the structure, function/activity, or expression of a protein, such as a SNP in a regulatory region (e.g. a promoter or enhancer) or a SNP that leads to alternative or defective splicing, such as a SNP in an intron or a SNP at an exon/intron boundary. As used herein, the terms "polypeptide", "peptide", and "protein" are used interchangeably.

Embodiments of the invention are further described in the following numbered paragraphs.

Paragraph 1. A method for treatment of dry eye comprising: administering a pharmaceutically effective amount of a dry eye therapeutic to an individual at risk for dry eye, wherein the individual at risk for dry eye has the presence of at least one single nucleotide polymorphism (SNP) in the THBS1 gene in a biological sample taken from the individual, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3).

Paragraph 2. The method of paragraph 2, wherein a pharmaceutically effective amount of a dry eye therapeutic is administered to an individual that has the presence of at least two single nucleotide polymorphisms (SNPs) of step a).

Paragraph 3. The method of paragraph 1, wherein a pharmaceutically effective amount of a dry eye therapeutic is administered to an individual that has the presence of at least three single nucleotide polymorphisms (SNPs) of step a).

Paragraph 4. The method of any of paragraphs 1-3, wherein the biological sample is selected from the group consisting of: a tissue biopsy, whole blood, plasma, serum urine, saliva, cerebrospinal fluid and a conjunctival impression cytology (CIC) sample.

Paragraph 5. The method of any of paragraphs 1-4, wherein the presence of at least one single nucleotide polymorphism (SNP) in the THBS1 gene is determined by genotyping nucleic acid derived from the biological sample using a method selected from the group consisting of: single-strand conformational polymorphism (SSCP) analysis, long range polymerase chain reaction (PCR), and allele specific hybridization.

Paragraph 6. The method of any of paragraphs 1-5, further comprising measuring expression of interleukin-1 beta in the biological sample.

Paragraph 7. The method of any of paragraphs 1-6, wherein the individual is in need of refractive eye surgery.

Paragraph 8. The method of any of paragraphs 1-7, wherein the dry eye therapeutic is selected from the group consisting and of: a lubricating substance and an immunosuppressant.

Paragraph 9. A method of determining a need for treatment of dry eye in an individual comprising the steps of: determining the presence or absence of at least one single nucleotide polymorphism (SNP), in the THBS1 gene in a biological sample taken from an individual in need of refractive eye surgery, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); determining a need for treating the individual for dry eye when the individual has the presence of at least one of the single nucleotide polymorphisms (SNPs) of step a); and determining no need for treating the individual for dry eye when the individual lacks each of the single nucleotide polymorphisms (SNPs) of step a).

Paragraph 10. The method of paragraph 9, wherein the individual is selected as being in need of eye surgery. (e.g. refractive eye surgery or other surgery).

Paragraph 11. The method of paragraph 9, wherein the individual is selected as having a condition associated with dry eye.

Paragraph 12. The method of paragraph 10, further comprising administering a pharmaceutically effective amount of a dry eye therapeutic to an individual determined to be in need of treatment, wherein the therapeutic is administered to the individual before, during, or after the individual undergoes eye surgery.

Paragraph 13. The method of any of paragraphs 9-12, wherein the dry eye therapeutic is selected from the group consisting and of: a lubricating substance an immunosuppressant.

Paragraph 14. The method of any of paragraphs 9-13, wherein in step b) the individual has the presence of at least two single nucleotide polymorphisms (SNPs) of step a).

Paragraph 15. The method of any of paragraphs 9-14, wherein in step b) the individual has the presence of at least three single nucleotide polymorphisms (SNPs) of step a).

Paragraph 16. The method of any of paragraphs 9-15, wherein the biological sample is selected from the group consisting of: a tissue biopsy, whole blood, plasma, serum urine, saliva, cerebrospinal fluid and a conjuctival impression cytology (CIC) sample.

Paragraph 17. The method of any of paragraphs 9-16, wherein the presence or absence of at least one single nucleotide polymorphism (SNP) in the THBS1 gene is determine by a method selected from the group consisting of: single-strand conformational polymorphism (SSCP) analysis, long range polymerase chain reaction (PCR), and allele specific hybridization.

Paragraph 18. The method of paragraph 9, further comprising measuring expression of interleukin-1 beta in the biological sample.

Paragraph 19. An assay comprising: genotyping the THBS1 loci of nucleic acid in a biological sample taken from an individual to detect the presence or absence of at least one single nucleotide polymorphism (SNP) in the THBS1 gene; wherein the presence of at least one SNP selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); indicates that the individual is at risk of developing dry eye and in need of treatment for dry eye post refractive eye surgery.

Paragraph 20. The assay of paragraph 19, wherein the presence of at least two single nucleotide polymorphisms (SNPs) of step a) indicates the individual is at risk for developing dry eye and in need of treatment.

Paragraph 21. The assay of paragraph 19, wherein the presence of at least three single nucleotide polymorphisms (SNPs) of step a) indicates the individual is at risk of development of dry eye and in need of treatment.

Paragraph 22. A paragraph for analyzing a biological sample comprising: a) a determination module configured to receive sequence data, and to determine sequence information, wherein the sequence information comprises a sequence of a coding or non-coding region of THBS1 gene or protein, obtained from a biological sample; b) a storage device configured to store sequence information from the determination module; c) a comparison module adapted to compare the sequence information stored on the storage device with reference data, and to provide a comparison result, wherein the comparison result identifies the presence or absence of a single nucleotide polymorphism (SNP), or corresponding amino acid change in THBS1 gene or protein, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); and wherein the SNP is indicative of an increased risk for dry eye disease; and d) a display module for displaying a content based in part on the comparison result for the user, wherein the content is a signal indicative of an increased risk for dry eye in the presence of at least one SNP of step c), or a signal indicative of lack of an increased risk for dry eye in the absence of each of the SNPs of step c).

Paragraph 23. The system of paragraph 22, wherein in step d) the content is a signal indicative of an increased risk for dry eye in the presence of at least two single nucleotide polymorphisms SNPs of step c), or a signal indicative of lack of an increased risk for dry eye in the absence of two of the SNPs of step c).

Paragraph 24. The system of paragraph 22, wherein in step d) the content is a signal indicative of an increased risk for dry eye in the presence of at least three single nucleotide polymorphisms SNPs of step c), or a signal indicative of lack of an increased risk for dry eye in the absence of one of the SNPs of step c).

Paragraph 25. A computer readable medium having computer readable instructions recorded thereon to define software modules including a comparison module and a display module for implementing a method on a computer, said method comprising: a) comparing with the comparison module the data stored on a storage device with reference data to provide a comparison result, wherein the comparison result identifies the presence or absence of a single nucleotide polymorphisms, or corresponding amino acid changes in THBS1 gene or protein, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3); and wherein the SNP is indicative of an increased risk for dry eye; and b) displaying a content based in part on the comparison result for the user, wherein the content is a signal indicative of an increased risk of dry eye in the presence of at least one SNP of step a), or a signal indicative of lack of an increased risk for dry eye in the absence of each of the SNPS of step a).

Paragraph 26. The computer readable medium of paragraph 25, wherein in step b) the content is a signal indicative of an increased risk for dry eye in the presence of at least two single nucleotide polymorphisms SNPs of step a), or a signal indicative of lack of an increased risk for dry eye in the absence two of the SNPs of step a).

Paragraph 27. The computer readable medium of paragraph 25, wherein in step b) the content is a signal indicative of an increased risk for dry eye in the presence of at least three single nucleotide polymorphisms SNPs of step a), or a signal indicative of lack of an increased risk for dry eye in the absence one of the SNPs of step a).

Example 1: Identification of Genetic Polymorphisms in Thrombospondin 1-Gene (THBS1) Associated with Dry Eye Syndrome Due to its minimally invasive nature refractive surgeries are a widely used form of vision correction to treat myopia, hyperopia and astigmatism. An estimated 1.5 million procedures are performed per year.[1] During refractive surgery disruption of the ocular surface structures especially its innervations leads to dry eye. This condition, although transient in some individuals, develops into a chronic form in many.[2-4] Dry eye is the most common complication observed post-refractive surgery with 40-60% of patients reported to develop this condition.[3, 5, 6] It is a disease that affects tear composition with consequential ocular discomfort, visual disturbances and is accompanied by inflammation of the ocular surface. A chronic inflammatory condition of the ocular surface results in damage to the ocular surface with a decreased corneal and conjunctival integrity and a loss of mucin secreting goblet cells.[7] Dry eye in general is multifactorial in etiology with risk factors besides refractive surgery such as age,[8] hormonal changes,[9] dry environments,[10] contact lens wear,[11] use of medications like antihistamines and diuretics, and systemic autoimmune disorders.[8] Not all individuals exposed to these risk factors develop dry eye, however the role of genetic factors has remained unaddressed, presumably due to the diversity of risk factors and lack of a consensus regarding diagnostic criteria and classification of dry eye conditions until recently (2007 Report of the Dry Eye Workshop (DEWS)).[7]

Dry eye due to a failure of tear secretion by the lacrimal glands is referred to as aqueous tear-deficient dry eye (ADDE) which is further subclassified based on autoimmune pathogenesis as Sjögren's syndrome Dry Eye (SSDE) and non-SSDE. Disrupted corneal innervations during refractive surgery interrupt stimulation of the lacrimal gland resulting in ADDE. Normally such dry eye is a self-resolving condition that improves with the recovery of corneal sensitivity but in some it progresses into a chronic condition often lasting beyond 6 months. Further classification of post-refractive surgery dry eye remains unclear possibly due to presumed non-autoimmune pathology underlying both self-resolving and chronic dry eye condition. Although clinical manifestation of post-refractive surgery chronic ocular surface inflammation resembles that seen in SSDE, the evidence of autoimmune pathology in the former remains to be established in human subjects. In murine studies however, ocular surface stress has been reported to induce dry eye with an autoimmune pathology[12-15] but it is not clear whether these studies are in essence describing SSDE. Therefore based on the current understanding of the pathogenesis post-refractive surgery dry eye may be considered a non-SSDE, however growing evidence from murine studies suggests a potential autoimmune pathogenic mechanism underlying the resultant chronic inflammatory condition of the ocular surface.

While the pathology underlying post-refractive surgery chronic dry eye remains unclear we sought an evaluation of a potential genetic association of this condition as a way to shed some light on its pathogenesis. To address the challenge of etiological heterogeneity of dry eye, in this study we chose a distinct causative factor such as refractive surgery to determine genetic predisposition of healthy individuals that undergo this procedure to develop chronic dry eye. Thus our study design helped avoid any influence of other factors that may contribute to the development of dry eye.

Deficiency of thrombospondin-1 (TSP-1) in mice results in spontaneous development of a chronic dry eye condition associated with autoimmune Sjögren's syndrome (SS).[16] Murine ocular surface inflammation bears a striking resemblance to that reported in human dry eye when taking into consideration various diagnostic parameters. These include altered tear quality, lacrimal gland dysfunction, disruption of ocular surface barrier, reduced goblet cell density and expression of inflammatory markers in the ocular surface tissue. A large multidomain glycoprotein, TSP-1, is produced by activated platelets and many other cell types including epithelial cells of the ocular surface.[17, 18]

Based on the significant role of TSP-1 identified in the regulation of dry eye pathogenesis we chose the TSP-1 gene (THBS1) as a candidate gene, located on human chromosome 15, to begin evaluation of whether genetic variants of this gene in human subjects increase their susceptibility to developing dry eye. Polymorphisms in the THBS1 gene encoding this molecule have been associated with altered calcium binding capacity, reduced plasma levels in humans and with increased risk of diseases like myocardial infarction.[19-21] In this study we evaluated the association of previously identified single nucleotide polymorphisms (SNPs), selected to represent different functional domains of TSP-1 and regulatory areas of the THBS1 gene, with the development of post-refractive surgery dry eye. Our results indicate a significant association between THBS1 polymorphism with dry eye and provide the first such evidence for a potential genetic basis for this condition.

Methods

Subjects

This research followed the tenets of the Declaration of Helsinki. The Institutional Review Board of the Department of the Army approved the study protocol. All patients gave written informed consent.

A total of 143 active duty U.S. Army soldiers wearing glasses or contact lenses for myopia with or without astigmatism were initially included in this study. Subjects in the age range of 21-40 years were recruited from those who requested refractive surgery. The selected subjects had manifest refractive spherical equivalent (MSE) of up to −10.00 diopters (D) at the spectacle plane with refractive cylinder up to 3.00 D, with best spectacle corrected visual acuity of 20/20 or better in both eyes, and demonstrated refractive stability (neither the spherical nor the cylindrical portion of the refraction changed more than 0.50 D during the 12-month period immediately preceding the baseline examination) as confirmed by clinical records. These subjects were also willing to fill out dry eye questionnaires (McMonnies) and to return for follow up visits on day one, day three, day seven, and one, three, six and 12 months after their surgery. Patients were excluded from the study who: were pregnant; or had previous surgery or trauma to the study eye; or had severe dry eye as reflected by Schirmer test with anesthesia of 0; or had any active ophthalmic disease; or had a history of medical conditions and/or medications that may impair healing.

Subjects underwent one of the two refractive surgeries—laser-assisted in situ keratomileusis (LASIK) or photorefractive keratotomy (PRK). Comprehensive eye examinations were performed prior to the surgery, one, three and seven days immediately after the procedure, and at one, three, six and 12 months post-surgery. Clinical assessments included measurement of tear production using Schirmer test, determination of tear film stability using sodium fluorescein tear breakup time (TBUT), evaluation of ocular surface integrity with Rose Bengal staining, McMonnies dry eye questionnaire, and impression cytology procedure. Impression cytology represents a non- or minimally invasive alternative to biopsy of the ocular surface epithelium[22] and was performed prior to the surgery and repeated at three months post-surgery. Specifically, two conjunctival impression cytologies were obtained from the nasal interpalpebral and inferior palpebral conjunctiva of each patient, using a circular disc of cellulose acetate filter pressed onto the conjunctival tissue for two seconds.

According to the diagnostic criteria shown in Table 1, each subject was given a score at each postoperative visit (at one, three, six and 12 months), as follows: 0=normal, 1=intermediate and 2=dry eye. After 12 months, all visits were tallied to categorize overall dry eye status. The "control" group in this study includes normal subjects with a score of "0" at the six month visit and either "0" or "1" on all other visits—i.e., no visits with a score of "2"; all the others formed the "dry eye" group, which included subjects with chronic dry eye (intermediate and dry eye) that persisted beyond 6 months.

SNP Selection

The candidate gene of this study THBS1 encodes a glycoprotein, TSP-1, with multiple functional domains (FIG. 1). Each domain has been characterized with a distinct function e.g. binding of latent transforming growth factor (TGF-)β and CD36 is associated with type I repeats in domain I and calcium binding is associated with domain III.[23] To search for genomic variants that may confer a risk of dry eye we reviewed SNPs identified in the THBS1 region (Chr15:37660572-37676959). In a 16.39 kbp long portion of THBS1 that spans mRNA positions 42-4403 and covers exons coding for all the TSP-1 domains in addition to noncoding 5'- and 3'-unstranslated regions (UTRs), 21 SNPs have been identified and also registered in the Phase II HapMap database for four populations (CEU, YRI, JPT and CHB).[24] We performed pairwise tagging in Haploview ($r^2$=0.8) for the available SNPs in HapMap populations (www.hapmap.org, accessed on Mar. 22, 2013) and selected tagged SNPs from each. Two SNPs (rs1478604 and rs2228262) were consistently tagged in all the populations. We then selected SNPs that represented different functional domains of TSP-1 and were in high linkage disequilibrium (LD) with the two tagged SNPs in at least two HapMap populations.[25] A total of five SNPs including two tagged SNPs as indicated in Table 2 and FIG. 1 were used in this study. Global minor allele frequencies of all the selected SNPs were >0.01.

Genotyping

Genomic DNA was obtained from conjunctival impression cytology (CIC) samples of 143 patients before refractive surgery, using QIAamp DNA Blood Mini Kit (Qiagen, Valencia, Calif.). Total DNA concentration was measured with the Quant-iT dsDNA kit (Invitrogen, Eugene, Oreg.). Samples that generated adequate DNA (5-10 ng/μl) (133 samples) were genotyped for five THBS1 SNPs using Sequenom iPLEX Gold platform (Sequenom, San Diego, Calif.) at the Molecular Genetics core of Children's Hospital, Boston and Harvard Medical School. The SNP ID (dbSNP), the genomic and protein positions and the nucleotide exchanges of the genotyped THBS1 SNPs are shown in Table 2. To control for possible confounding by population stratification, a panel of 90 ancestry-informative markers (AIMs) was screened in all samples.[26]

Quality Control (QC)

We genotyped five selected SNPs (SNP1-5) in 133 individuals. Samples with a genotype rate<85% were excluded (n=58). The numbers of samples excluded from the control and dry eye group did not differ significantly (p>0.05, odds ratio [OR] 1.5, CI 0.6-3.6). A final set of 16 controls and 59 dry eye subjects with a genotyping rate of 98% was analyzed further. This QC step did not result in any change in overall population characteristics in the two groups (Table 3, available at http://aaojournal.org). All but one SNP were in Hardy Weinberg equilibrium (HWE) (SNP1-4, p>0.3, SNP5 p=0.0023). Therefore SNP5 was excluded from further association analysis. As an additional QC, a gender SNP was genotyped and matched with the demographic data. All the gender genotypes matched with the corresponding demographic information of the individuals.

Real Time Polymerase Chain Reaction (PCR)

Total RNA was isolated from CIC samples of 27 subjects three months after refractive surgery (15 healthy controls and 12 dry eye patients), using RNeasy Mini Kit (Qiagen, Valencia, Calif.) according to the manufacturer's instructions. Contaminating DNA was eliminated by digestion with RNase-Free DNase Set (Qiagen). The extracted RNA was reverse-transcribed to cDNA with the SuperScript Vilo cDNA Kit (Invitrogen, Eugene, Oreg.) following the manufacturer's protocol. Real-time PCR assay was performed on the Eppendorf Realplex2 system (Eppendorf AG, Hamburg, Germany) using SYBR Green PCR Master Mix (Applied Biosystems, Carlsbad, Calif.) to determine relative quantitative expression levels of TSP-1 and interleukin (IL-) 1β genes. TSP-1 primers (F-5'-GGACTCTGACGGCGATG-GTC-3' (SEQ ID NO: 6) and R-5'-ATCGGCGGAAATCG-GTCTC-3' (SEQ ID NO: 7), IL-1 β primers (F-5'-CG-GCATCCAGCTACGAATC-3' (SEQ ID NO: 8) and R-5'-CCATGGCCACAACAACTGAC-3' (SEQ ID NO: 9)), and β-actin primers (F-5'-CGGGAAATCGTGCGTGAC-3' (SEQ ID NO: 10) and R-5'-GTGGCCATCTCTTGCTC-GAA-3' (SEQ ID NO: 11)) were used. Amplification reactions were set up in triplicates with the thermal profile: 95° C. for three minutes, 40 cycles at 95° C. for ten seconds, 56° C. for ten seconds and 72° C. for ten seconds. To verify the specificity of the amplification reaction, a melting curve analysis was performed. Fluorescence signal generated at each cycle was analyzed using the system software. The threshold cycle values were used to determine relative quantitation of gene expression with β-actin as a reference gene.

Statistical Analysis

THBS1 polymorphisms in post-surgery healthy and dry eye patients were analyzed using gPLINK software (version 1.0)[27] [http://pngu.mgh.harvard.edu/~purcell/plink/] and GraphPad Prism (version 5.0 for Mac) (GraphPad Software, La Jolla, Calif.). To control for possible population stratification, 90 ancestry informative markers were genotyped and data was analyzed against HapMap populations CEU, JPT/CHB and YRI using Structure software (version 2.3.4)[28] [http://pritchardlab.stanford.edu/structure.html] Allelic frequencies divergence was compared between and within the populations and the genomic inflation factor lamda (λ) was determined Departure from HWE was also evaluated. Exclusion criteria included deviation from HWE at p<0.01, and sample genotyping rate<85%.

Allele and genotyping frequencies were compared using Fisher's exact test to estimate the significance of the association with post-surgery dry eye. Odds ratios (ORs), 95% confidence intervals (95% CIs), and frequencies for indicated genetic models were calculated and p values less than 0.05 were considered significant. Considering high LD among 3 SNPs with significant associations no Bonferroni correction was applied to avoid false negative associations.

Haploview 4.1[29] [http://www.broadinstitute.org/scientific-community/science/programs/medical-and-population-genetics/haploview/haploview] was used to study LD. Coefficients of LD (D) of allele frequencies for SNPs were compared using the confidence interval method of Gabriel et al[30] to infer haplotype blocks.

Student's t-test was used to determine significant differences in mRNA expression levels. Data were expressed as means±standard error of the means. Differences were considered to be significant when p≤0.05.

Results

Study Population

Figure 2:
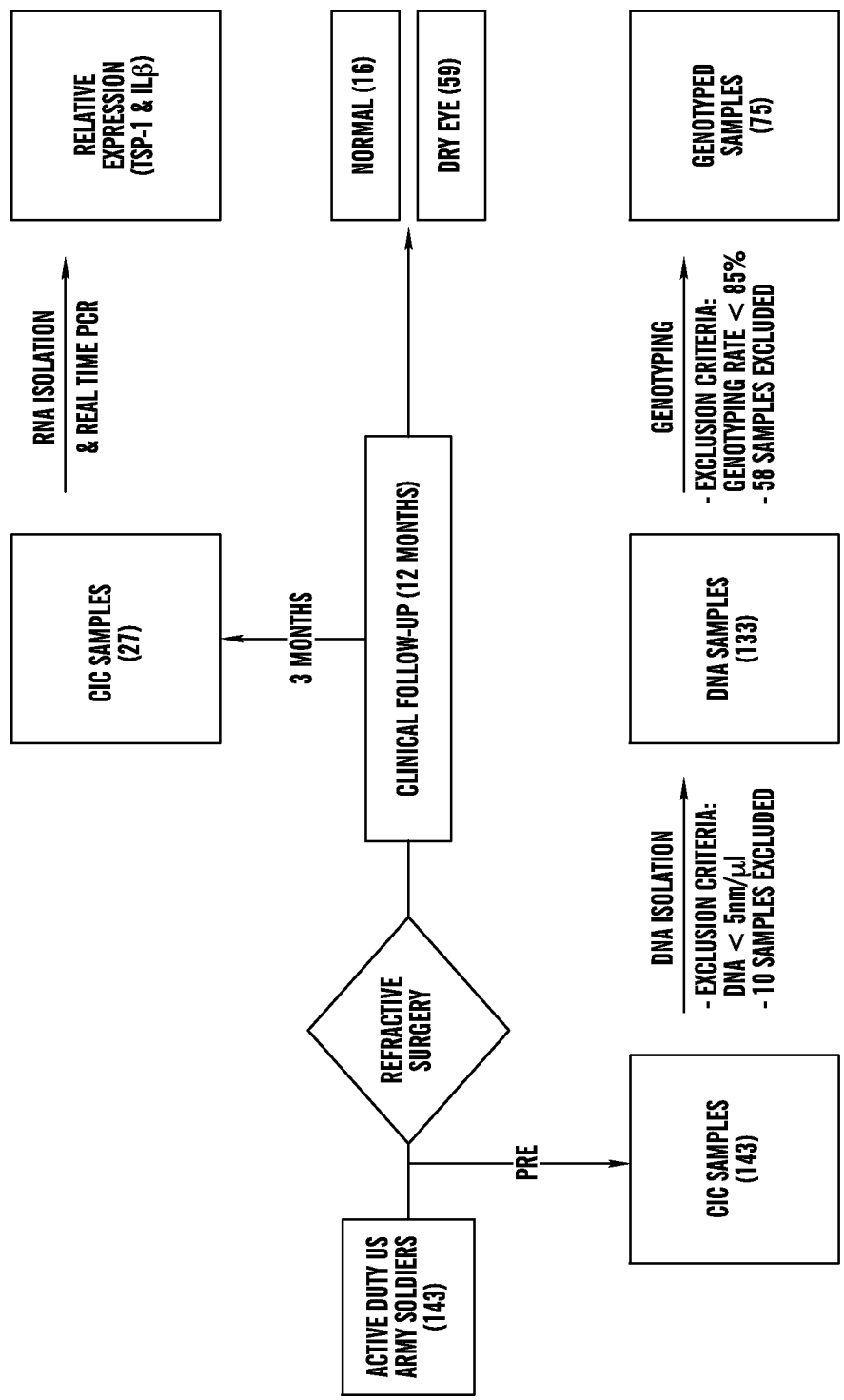
FIG. 2 shows a schematic of the study design. A total of 143 subjects underwent refractive surgery and were examined during 12 months for the presence of dry eye. Individuals that did not develop dry eye formed the "control" group (normal; 16) while the others were included in "dry eye" group (dry eye; 59). Genomic DNA and RNA were obtained from conjunctival impression cytology (CIC) samples prior to (PRE) and 3 months after refractive surgery for genotyping of thrombospondin-1 (TSP-1) single nucleotide polymorphisms (SNPs) and real time polymerase chain reaction (PCR) analysis of TSP-1 and interleukin (IL)-1β.

In total, 143 active duty U.S. Army soldiers opting for refractive surgery formed the study population. All of these individuals underwent refractive surgery and were examined for the presence of dry eye using diagnostic criteria as indicated in Table 1. Individuals that did not develop dry eye formed the "control" group while others, including intermediate and chronic dry eye, were included in "dry eye" group (FIG. 2). Mean age of individuals in both groups was 29 with a comparable male to female ratio (dry eye 1.95 vs. controls 1.7). At the end of the study period Schirmer test, a routine clinical test used to evaluate aqueous tear production, indicated reduced levels in the dry eye group compared to those in controls (p<0.01)(Table 4).

To rule out any influences of population stratification on the genetic analysis we included a set of 90 ancestry-informative markers (AIMs) in genotyping to infer genetic ancestry of the population under investigation.[26] Comparison of AIM genotypes in our study population with established HapMap populations identified ancestry to be approximately 51% CEU, 32% YRI and 17% JPT/CHB which appeared to be consistent with the latest (FY11) active duty army demographic profile (published by Department of the Army at http://www.armyg1.army.mil/hr/demographics.asp and accessed in Mar. 1, 2013). The allelic frequency divergence (variance of log likelihood=287.4) and low genomic inflation factor lambda for the study population (λ=0.44) suggested an absence of significant population stratification. Furthermore, allelic frequencies of analyzed SNPs in this study matched closely with those reported in corresponding HapMap populations (Table 5, available at http://aaojournal.org) indicating their comparable distribution.[25] Similarly the LD pattern of the four analyzed SNPs in the study population (FIG. 3) resembled those detected in HapMap populations (FIG. 4, available at http://aaojournal.org).[25]

Association of THBS1 Variants with the Development of Post-Refractive Dry Eye

Allelic and genotype frequencies of four SNPs from the THBS1 gene were assessed for their association with the development of dry eye after refractive surgery. As shown in Table 6, the frequency of SNP1 minor allele was significantly increased in individuals diagnosed with dry eye as compared to the individuals in control group (p=0.03) with an OR of 2.83 (95% CI 1.21-7.16). Frequencies of the remaining three SNPs did not differ significantly between the groups. This result suggests that individuals with SNP1 minor allele are susceptible to developing dry eye after undergoing refractive surgery as compared to those expressing the major allele. Analysis of genotypic frequencies yielded significant associations with the dominant model where frequencies of the minor allele carriers of SNP1, 2 or 3 were significantly increased in dry eye group compared to the control group. Specifically, the frequency of SNP1 C minor allele carriers (CT+CC) in dry eye patients was 69% as against 47% in control group (p=0.0025, OR 2.5, 95% CI 1.4-4.5). The frequencies of minor allele carriers of SNP2 (CT+TT), as well as SNP3 (AG+GG) were 39% in dry eye patients compared to 25% in controls (p=0.048, OR 1.9, 95% confidence interval (95% CI) 1.1-3.5). No significant association was observed in SNP4, as the frequency of the minor allele carriers (AG+GG) was 19% in both groups (p=1.0, OR 1.0, 95% CI 0.49-2.03). The SNP5 was excluded from analysis due to departure from HWE. The association of minor allele carriers of SNP1 was the strongest with the development of post-refractive surgery dry eye. These results indicate that the presence of only one minor allele is sufficient to increase the risk of dry eye. Taken together, these data indicate statistically significant evidence for association between THBS1 polymorphism, and the development of dry eye post-refractive surgery.

Linkage Disequilibrium (LD)D and Haplotype Analysis

Figure 3:
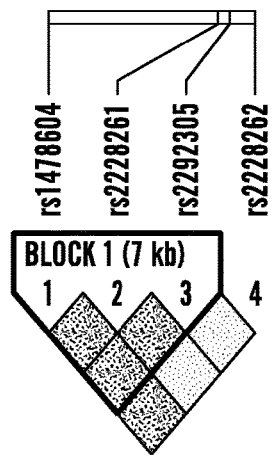
FIG. 3 shows a schematic of Linkage disequilibrium (LD) pattern of genotyped thrombospondin-1 gene (THBS1) polymorphisms. The figure shows the LD coefficient (D')-based pairwise LD map of 4 single nucleotide polymorphisms (SNPs) genotyped in this study, created with Haploview software version 4.1. Darker shaded areas indicate higher D'. A haplotype block is outlined and was defined using the confidence interval method of Gabriel et al. (see reference 30 of Example 1).
Figure 4:
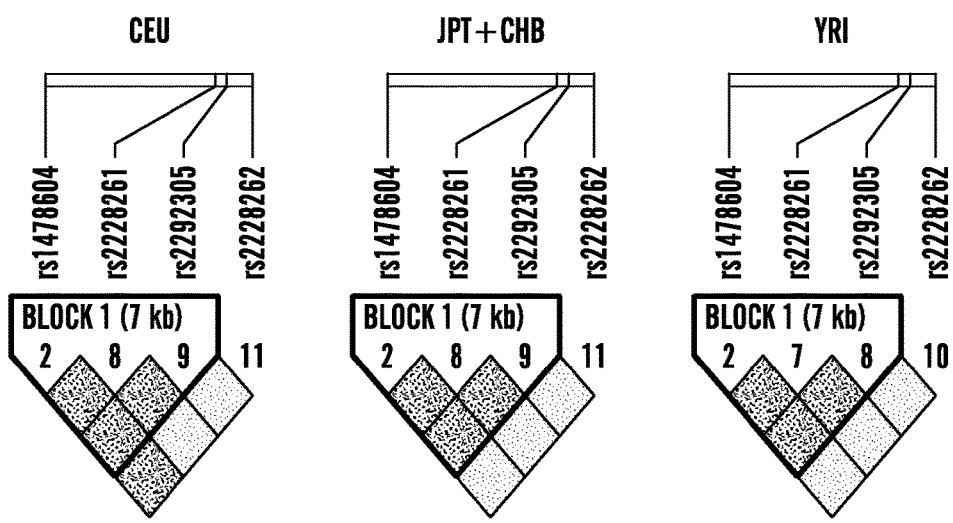
FIG. 4 shows a schematic of Linkage disequilibrium (LD) pattern of four analyzed single nucleotide polymorphisms (SNPS) in the study population resembled those detected in HapMap populations. The figure shows the D'-based pairwise LD map of 4 SNPs genotyped in HapMap populations. Darker shaded areas indicate higher LD coefficient D.' The same haplotype block was outlined in the three populations.

To locate disease-associated sequence variation, we estimated LD with Haploview analysis. The pairwise LD structure was constructed with four SNPs genotyped (all with minor allele frequencies>0.01 and conforming to HWE). Coefficients of LD (D) were generated applying confidence interval method of Gabriel et al.[30] As shown in FIG. 3, SNP1-3 fall in one LD block, with SNP2 and SNP3 in perfect LD (D=1). We then examined haplotypes based on these three SNPs (Table7). Although a trend of increased frequencies of haplotypes carrying minor alleles of SNP1 and 2 (CTG and CCA respectively) was detected in patients with dry eye compared to control subjects (0.237 vs. 0.125 and 0.214 vs. 0.133 respectively), the differences did not reach statistical significance. However, frequency of TCA haplotype representing major alleles of the three SNPs was significantly increased among control subjects (0.742) compared to dry eye patients (0.549) suggesting a potential protective role of this haplotype in the development of post-refractive surgery dry eye.

Allele-Specific Expression of TSP-1 and its Correlation with Inflammation

Figure 5B:
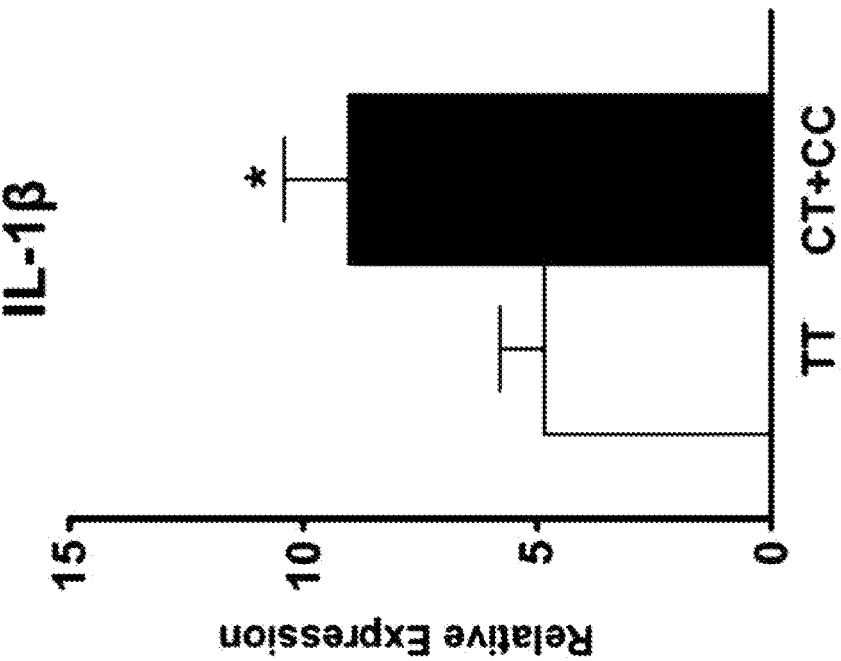
FIGS. 5a and 5b show graphs of relative expression of TSPT (FIG. 5a) and IL-1β (FIG. 5b) in normal (TT) and SNP1 minor allele carriers (CT+CC). The graphs indicate reduced thrombospondin-1 (TSP-1) levels and increased inflammation are detectable in SNP1 minor allele carriers. RNA was harvested from conjunctival impression cytology samples and analyzed using SYBR Green real time polymerase chain reaction (PCR) assay to determine levels of TSP-1 (FIG. 5a) and interleukin (IL)-1b (FIG. 5b). Expression of TSP-1 in SNP1 minor allele carriers (CC+CT) compared to major genotype (TT) was significantly reduced, while expression of inflammatory cytokine IL-1β was significantly increased. (*p<0.05).
Figure 5A:
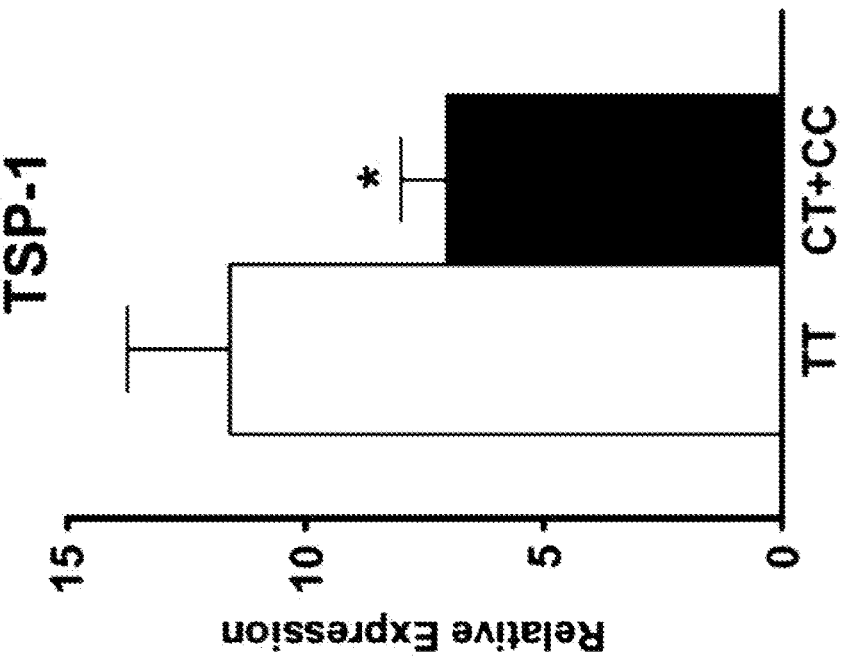

Previously we have reported spontaneous development of ocular surface inflammation (dry eye) in mice deficient in TSP-1.[16] Therefore we hypothesized that similarly reduced TSP-1 expression in humans may result in ocular surface inflammation. In our study, CIC samples collected three months after refractive surgery provided ocular surface epithelial cells from each individual that could be evaluated for TSP-1 expression. We harvested RNA from CIC samples and assessed TSP-1 levels in a real-time PCR assay. We also assessed expression of an inflammatory marker associated with dry eye, IL-1β. As shown in FIG. 5a we noted significantly reduced expression of TSP-1 in SNP1 minor allele carriers (CT+CC) as compared to the individuals expressing the major allele (TT). This reduced TSP-1 expression was also accompanied by significantly increased expression of IL-1β (FIG. 5b). These results confirm our observations from the association study that SNP in a regulatory 5'-UTR of THBS1 gene correlates with a lowered expression of TSP-1 in the ocular surface epithelial cells and with the increased expression of an inflammatory marker. Together our results indicate an association of THBS1 polymorphism with the development of ocular surface inflammation as seen in dry eye.

Discussion

The present study showed the minor allele C and genotypes CT and CC of SNP1 (rs1478604) in THBS1 gene are associated with the dry eye development post-refractive surgery in a group of active duty U.S. Army soldiers. The strength of both of these associations was odds ratio≥2.5. Moreover the frequency of a haplotype carrying major alleles of three SNPs was significantly higher in the controls than dry eye group. We also detected significantly reduced expression of TSP-1 in the ocular surface epithelia of individuals with SNP1 minor allele. These individuals also expressed significantly elevated levels of an inflammatory cytokine, IL-1β, associated with dry eye.

TSP-1 is expressed by many cell types including ocular surface epithelia.[17, 18, 31] Binding sites for many receptors as well as intra and extracellular molecules have been identified in different domains of TSP-1.[17] As such, many diverse functions are attributed to TSP-1 depending on the receptors engaged by this molecule and the cells expressing them. In the eye, damaged corneal epithelial cells are reported to utilize TSP-1 in corneal wound repair.[32, 33, 28] A significant role of TSP-1 in the regulation of ocular inflammatory angiogenesis as well as lymphangiogenesis is documented.[34, 35] In murine studies we have reported TSP-1 dependent regulation of ocular antigen presenting cells and inflammatory responses mediated by them.[36-38] There are several studies that demonstrated TSP-1 dependent regulation of inflammatory responses by human dendritic cells.[39, 40, 31] These reports in combination with our reported dry eye pathology in TSP-1 deficient mice strongly suggest a potential role for TSP-1 in the regulation of ocular surface inflammatory conditions such as dry eye.

Our present study design allowed for a clear assessment of dry eye resulting from a distinct factor like refractive surgery. However, given the high prevalence of dry eye six months after refractive surgery (60-90%)[2-4] achieving 1:1 sample to control ratio, with a one year follow up, was not possible. Taking into account this limitation and considering that no such study has been reported as yet several stringent quality control measures were applied to minimize potential confounding factors and to increase the probability of its replication in a future larger study. The control group in our study includes individuals that underwent refractive surgery similar to the experimental dry eye group. In addition to this we identified a candidate gene with a known sequence and well characterized structure of the protein it encodes. This information helped selection of SNPs from TSP-1 domains with known associations with cellular function.

Genetic variation in the 5'-UTR region of DNA with regulatory components has a strong potential to influence the transcription and therefore possibly expression of a gene. In this study the 5'-UTR location of SNP1 indeed appears to alter transcription of THBS1 as we noted a significant decline in the expression of TSP-1 mRNA in ocular surface epithelia derived from individuals genotyped with minor allele of SNP1 (C). Indeed the lowest expression of TSP-1 was detected in one subject homozygous for this minor allele (data not shown). This change in TSP-1 expression was also accompanied with an increased expression of an inflammatory marker, IL-1β, associated with dry eye. Together these results implicate a regulatory role of TSP-1 in the ocular surface inflammatory condition.

The location of two SNPs included in this study (SNP2 and 3) in structural domains of TSP-1 (type 1 and 2 repeats respectively) corresponds with the functions of TSP-1 relevant to dry eye condition. That is, while activation of immunosuppressive TGF-β is associated with type 1 repeats,[41] the binding of TSP-1 to epidermal growth factor receptor (EGFR) is associated with type 2 repeats.[42] A disruption in type I repeats can interfere with the availability of anti-inflammatory TGF-β to counter inflammation as well as wound healing[43] at the ocular surface. Similarly, disruption in type 2 repeats may interfere with EGFR signaling of mucin secreting goblet cells of the ocular surface.[44, 45] A marginally significant increase in genotype frequencies of both SNP2 and 3 in subjects with dry eye suggested a trend that is in line with the functions associated with the corresponding TSP-1 regions. Identical frequencies of these two SNPs are also consistent with a perfect LD between them.

Our study has assessed the genetic basis underlying a commonly encountered complication post-refractive surgery—dry eye. Our results in this study indicate a genetic basis for the dry eye condition. Based on the intensity of dry eye as determined by clinical scoring, 72% of subjects from the dry eye group were classified with an intermediate level and the remaining 28% with a higher intensity of chronic inflammation. Such a distribution of subjects clearly supports variability of the disease, while incomplete disease penetrance is noted in the case of significantly associated SNPs. Both of these observations are consistent with the multifactorial etiology of a complex trait disease like dry eye. Furthermore, in control group subjects heterozygous for SNP1 (47%) and for SNP2 and SNP3 (25% each) remained unaffected indicating their carrier phenotype.

In determining candidacy for refractive surgeries systemic autoimmune diseases such as rheumatoid arthritis and Sjögren's syndrome are considered contraindications due to the possibility of exacerbating any ocular inflammation associated with these diseases. However, potential risk of precipitating autoimmunity by exposing ocular surface autoantigens in an inflammatory response like dry eye remains unknown. Our results in this study substantiate our findings from murine studies which suggest that reduced TSP-1 expression promotes a pro-inflammatory phenotype of tissue antigen presenting cells and disrupts immune regulation that follows normal wound healing leading to a chronic inflammatory disease. In TSP-1 deficient mice this chronic inflammation progresses to age-related autoimmunity resulting in autoimmune Sjögren's syndrome[16]. It was recently reported that nearly 12% of patients with dry eye develop autoimmune SS or systemic autoimmune disease[46] suggesting dry eye as a potential early event or symptom of a systemic condition. In the context of such possibilities screening individuals for susceptibility to developing dry eye prior to refractive surgeries will help improve post-surgery management as well as prevention of possible long-term risks. In this regard our study presents THBS1 variants as a potential genetic biomarker to identify individuals at risk of developing chronic dry eye.

REFERENCES

1. Kojima T, Ongucci T, Hallak J, Azar D. Chapter 19, Management of Complications in Refractive Surgery. Editors: Alio J L and Azar D T 2008; pp 329-350
2. Hovanesian J A, Shah S S, Maloney R K. Symptoms of dry eye and recurrent erosion syndrome after refractive surgery. J Cataract Refract Surg 2001; 27:577-84.
3. De Paiva C S, Chen Z, Koch D D, et al. The incidence and risk factors for developing dry eye after myopic LASIK. Am J Ophthalmol 2006; 141:438-45.
4. Toda I, Asano-Kato N, Komai-Hori Y, Tsubota K. Dry eye after laser in situ keratomileusis. Am J Ophthalmol 2001; 132:1-7.
5. Yu E Y, Leung A, Rao S, Lam D S. Effect of laser in situ keratomileusis on tear stability. Ophthalmology 2000; 107:2131-5.
6. Salomao M Q, Ambrosio R Jr, Wilson S E. Dry eye associated with laser in situ keratomileusis: mechanical microkeratome versus femtosecond laser. J Cataract Refract Surg 2009; 35:1756-60.
7. The definition and classification of dry eye disease: report of the Definition and Classification Subcommittee of the International Dry Eye WorkShop (2007). Ocul Surf 2007; 5:75-92.

8. Moss S E, Klein R, Klein B E. Incidence of dry eye in an older population. Arch Ophthalmol 2004; 122:369-73.
9. Schaumberg D A, Sullivan D A, Buring J E, Dana M R. Prevalence of dry eye syndrome among US women. Am J Ophthalmol 2003; 136:318-26.
10. Uchiyama E, Aronowicz J D, Butovich I A, McCulley J P. Increased evaporative rates in laboratory testing conditions simulating airplane cabin relative humidity: an important factor for dry eye syndrome. Eye Contact Lens 2007; 33:174-6.
11. Uchino M, Schaumberg D A, Dogru M, et al. Prevalence of dry eye disease among Japanese visual display terminal users. Ophthalmology 2008; 115:1982-8.
12. Niederkorn J Y, Stern M E, Pflugfelder S C, et al. Desiccating stress induces T cell-mediated Sjogren's Syndrome-like lacrimal keratoconjunctivitis. J Immunol 2006; 176:3950-7.
13. Dursun D, Wang M, Monroy D, et al. A mouse model of keratoconjunctivitis sicca. Invest Ophthalmol Vis Sci 2002; 43:632-8.
14. Barabino S, Shen L, Chen L, et al. The controlled-environment chamber: a new mouse model of dry eye. Invest Ophthalmol Vis Sci 2005; 46:2766-71.
15. Stern M E, Schaumburg C S, Pflugfelder S C. Dry eye as a mucosal autoimmune disease. Int Rev Immunol 2013; 32:19-41.
16. Turpie B, Yoshimura T, Gulati A, et al. Sjogren's syndrome-like ocular surface disease in thrombospondin-1 deficient mice. Am J Pathol 2009; 175:1136-47.
17. Adams J C, Lawler J. The thrombospondins. Cold Spring Harb Perspect Biol [serial online] 2011; 3:a009712. Available at: http://www.ncbi.nlm.nih.gov/pmc/articles/PMC3179333/. Accessed Jan. 20, 2014.
18. Sekiyama E, Nakamura T, Cooper L J, et al. Unique distribution of thrombospondin-1 in human ocular surface epithelium. Invest Ophthalmol Vis Sci 2006; 47:1352-8.
19. Zwicker J I, Peyvandi F, Palla R, et al. The thrombospondin-1 N700S polymorphism is associated with early myocardial infarction without altering von Willebrand factor multimer size. Blood 2006; 108:1280-3.
20. Topol E J, McCarthy J, Gabriel S, et al. Single nucleotide polymorphisms in multiple novel thrombospondin genes may be associated with familial premature myocardial infarction. Circulation 2001; 104:2641-4.
21. Hannah B L, Misenheimer T M, Pranghofer M M, Mosher D F. A polymorphism in thrombospondin-1 associated with familial premature coronary artery disease alters Ca2+ binding. J Biol Chem 2004; 279:51915-22.
22. Calonge M, Diebold Y, Saez V, et al. Impression cytology of the ocular surface: a review. Exp Eye Res 2004; 78:457-72.
23. Lopez-Dee Z, Pidcock K, Gutierrez L S. Thrombospondin-1: multiple paths to inflammation. Mediators Inflamm 2011; 2011:296069.
24. Thorisson G A, Smith A V, Krishnan L, Stein L D. The International HapMap Project Web site. Genome Res 2005; 15:1592-3.
25. International HapMap Consortium. The International HapMap Project. Nature 2003; 426:789-96.
26. Hoggart C J, Parra E J, Shriver M D, et al. Control of confounding of genetic associations in stratified populations. Am J Hum Genet 2003; 72:1492-504.
27. Purcell S, Neale B, Todd-Brown K, et al. PLINK: a tool set for whole-genome association and population-based linkage analyses. Am J Hum Genet 2007; 81:559-75.
28. Pritchard J K, Stephens M, Donnelly P. Inference of population structure using multilocus genotype data. Genetics 2000; 155:945-59.
29. Barrett J C, Fry B, Maller J, Daly M J. Haploview: analysis and visualization of LD and haplotype maps. Bioinformatics 2005; 21:263-5.
30. Gabriel S B, Schaffner S F, Nguyen H, et al. The structure of haplotype blocks in the human genome. Science 2002; 296:2225-9.
31. Hiscott P, Seitz B, Schlotzer-Schrehardt U, Naumann G O. Immunolocalisation of thrombospondin 1 in human, bovine and rabbit cornea. Cell Tissue Res 1997; 289:307-10.
32. Matsuba M, Hutcheon A E, Zieske J D. Localization of thrombospondin-1 and myofibroblasts during corneal wound repair. Exp Eye Res 2011; 93:534-40.
33. Uno K, Hayashi H, Kuroki M, et al. Thrombospondin-1 accelerates wound healing of corneal epithelia. Biochem Biophys Res Commun 2004; 315:928-34.
34. Chen L, Cursiefen C, Barabino S, et al. Novel expression and characterization of lymphatic vessel endothelial hyaluronate receptor 1 (LYVE-1) by conjunctival cells. Invest Ophthalmol Vis Sci 2005; 46:4536-40.
35. Cursiefen C, Maruyama K, Bock F, et al. Thrombospondin 1 inhibits inflammatory lymphangiogenesis by CD36 ligation on monocytes. J Exp Med 2011; 208:1083-92.
36. Masli S, Turpie B, Streilein J W. Thrombospondin orchestrates the tolerance-promoting properties of TGF-beta-treated antigen-presenting cells. Int Immunol 2006; 18:689-99.
37. Ng T F, Turpie B, Masli S. Thrombospondin-1-mediated regulation of microglia activation after retinal injury. Invest Ophthalmol Vis Sci 2009; 50:5472-8.
38. Saban D R, Bock F, Chauhan S K, et al. Thrombospondin-1 derived from APCs regulates their capacity for allosensitization. J Immunol 2010; 185:4691-7.
39. Doyen V, Rubio M, Braun D, et al. Thrombospondin 1 is an autocrine negative regulator of human dendritic cell activation. J Exp Med 2003; 198:1277-83.
40. Grimbert P, Bouguermouh S, Baba N, et al. Thrombospondin/CD47 interaction: a pathway to generate regulatory T cells from human CD4+CD25− T cells in response to inflammation J Immunol 2006; 177:3534-41.
41. Schultz-Cherry S, Chen H, Mosher D F, et al. Regulation of transforming growth factor-beta activation by discrete sequences of thrombospondin 1. J Biol Chem 1995; 270:7304-10.
42. Calzada M J, Annis D S, Zeng B, et al. Identification of novel beta1 integrin binding sites in the type 1 and type 2 repeats of thrombospondin-1. J Biol Chem 2004; 279:41734-43.
43. Nor J E, Dipietro L, Murphy-Ullrich J E, et al. Activation of latent TGF-beta1 by thrombospondin-1 is a major component of wound repair. Oral Biosci Med 2005; 2:153-61.
44. Gu J, Chen L, Shatos M A, et al. Presence of EGF growth factor ligands and their effects on cultured rat conjunctival goblet cell proliferation. Exp Eye Res 2008; 86:322-34.
45. Hodges R R, Bair J A, Carozza R B, et al. Signaling pathways used by EGF to stimulate conjunctival goblet cell secretion. Exp Eye Res 2012; 103:99-113.
46. Liew M S, Zhang M, Kim E, Akpek E K. Prevalence and predictors of Sjogren's syndrome in a prospective cohort of patients with aqueous-deficient dry eye. Br J Ophthalmol 2012; 96:1498-503.

Sequences (SEQ ID NOs: 1-5).
UPDATED VIEW Chromosome 15: 39581079-39597467THBS1 [HomoSapiens]
*Homo sapiens* chromosome 15, GRCh38 Primary Assembly
NCBI Reference Sequence: NC_000015.10
CommentFeaturesSequence
LOCUS NC_000015 16389 bp DNA linear CON 3 Feb. 2014
DEFINITION *Homo sapiens* chromosome 15, GRCh38 Primary Assembly.
ACCESSION NC_000015 REGION: 39581079..39597467 GPC_000001307
VERSION NC_000015.10 GI:568815583
DBLINK BioProject: PRJNA168
  Assembly: GCF_000001405.26
KEYWORDS RefSeq.
SOURCE *Homo sapiens* (human)
  ORGANISM *Homo sapiens*
  Eukaryota; Metazoa; Chordata; Craniata; Vertebrata; Euteleostomi; Mammalia; Eutheria; Euarchontoglires; Primates; Haplorrhini; Catarrhini; Hominidae; Homo.
REFERENCE 1 (bases 1 to 16389)
  AUTHORS Zody, M. C., et al.
  TITLE Analysis of the DNA sequence and duplication history of human chromosome 15
  JOURNAL Nature 440 (7084), 671-675 (2006)
  PUBMED 16572171
REFERENCE 2 (bases 1 to 16389)
  CONSRTM International Human Genome Sequencing Consortium
  TITLE Finishing the euchromatic sequence of the human genome
  JOURNAL Nature 431 (7011), 931-945 (2004)
  PUBMED 15496913
REFERENCE 3 (bases 1 to 16389)
  AUTHORS Lander, E. S., et al.
  CONSRTM International Human Genome Sequencing Consortium
  TITLE Initial sequencing and analysis of the human genome
  JOURNAL Nature 409 (6822), 860-921 (2001)
  PUBMED 11237011
  REMARK Erratum: [Nature 2001 Aug. 2; 412(6846): 565]
COMMENT REFSEQ INFORMATION: The reference sequence is identical to CM000677.2.
  On Feb. 3, 2014 this sequence version replaced gi:224589806.
  Assembly Name: GRCh38 Primary Assembly
  The DNA sequence is composed of genomic sequence, primarily finished clones that were sequenced as part of the Human Genome Project. PCR products and WGS shotgun sequence have been added where necessary to fill gaps or correct errors. All such additions are manually curated by GRC staff. For more information see: http://genomereference.org.

Genome-Annotation-Data-START##
Annotation Provider       :: NCBI
Annotation Status         :: Full annotation
Annotation Version        :: Homo sapiens Annotation Release 106
Annotation Pipeline       :: NCBI eukaryotic genome annotation pipeline
Annotation Software Version :: 5.2
Annotation Method         :: Best-placed RefSeq; Gnomon
Features Annotated        :: Gene; mRNA; CDS; ncRNA
Genome-Annotation-Data-END##

| FEATURES | Location/Qualifiers |
|---|---|
| source | 1..16389<br>/organism="Homo sapiens"<br>/mol_type="genomic DNA"<br>/db_xref="taxon:9606"<br>/chromosome="15" |
| gene | 1..16389<br>/gene="THBS1"<br>/gene_synonym="THBS; THBS-1; TSP; TSP-1; TSP1"<br>/note="thrombospondin 1; Derived by automated computational analysis using gene prediction method: BestRefSeq."<br>/db_xref="GeneID:7057"<br>/db_xref="HGNC:11785"<br>/db_xref="MIM:188060" |
| mRNA | join(1..150,751..846,1115..1674,2539..2614,2910..3109,<br>3222..3344,4392..4485,6269..6442,6964..7140,7448..7621,<br>7881..8008,8124..8276,8727..8945,9438..9545,10113..10272,<br>10427..10545,11490..11724,11922..12149,12319..12590,<br>13021..13118,13223..13362,14284..16389)<br>/gene="THBS1"<br>/gene_synonym="THBS; THBS-1; TSP; TSP-1; TSP1"<br>/product="thrombospondin 1"<br>/note="Derived by automated computational analysis using gene prediction method: BestRefSeq."<br>/transcript_id="NM_003246.2"<br>/db_xref="GI:40317625"<br>/db_xref="GeneID:7057"<br>/db_xref="HGNC:11785"<br>/db_xref="MIM:188060" |

-continued

```
FEATURES    Location/Qualifiers
CDS         join(780..846,1115..1674,2539..2614,2910..3109,3222..3344,
            4392..4485,6269..6442,6964..7140,7448..7621,7881..8008,
            8124..8276,8727..8945,9438..9545,10113..10272,
            10427..10545,11490..11724,11922..12149,12319..12590,
            13021..13118,13223..13362,14284..14291)
            /gene="THBS1"
            /gene_synonym="THBS; THBS-1; TSP; TSP-1; TSP1"
            /note="Derived by automated computational analysis using
            gene prediction method: BestRefSeq."
            /codon_start=1
            /product="thrombospondin-1 precursor"
            /protein_id="NP_003237.2"
            /db_xref="GI:40317626"
            /db_xref="CCDS:CCDS32194.1"
            /db_xref="GeneID:7057"
            /db_xref="HGNC:11785"
            /db_xref="MIM:188060"
            /translation="MGLAWGLGVLFLMHVCGTNRIPESGGDNSVFDIFELTGAARKGS
GRRLVKGPDPSSPAFRIEDANLIPPVPDDKFQDLVDAVRAEKGFLLLASLRQMKKTRG
TLLALERKDHSGQVFSVVSNGKAGTLDLSLTVQGKQHVVSVEEALLATGQWKSITLFV
QEDRAQLYIDCEKMENAELDVPIQSVFTRDLASIARLRIAKGGVNDNFQGVLQNVRFV
FGTTPEDILRNKGCSSSTSVLLTLDNNVVNGSSPAIRTNYIGHKTKDLQAICGISCDE
LSSMVLELRGLRTIVTTLQDSIRKVTEENKELANELRRPPLCYHNGVQYRNNEEWTVD
SCTECHCQNSVTICKKVSCPIMPCSNATVPDGECCPRCWPSDSADDGWSPWSEWTSCS
TSCGNGIQQRGRSCDSLNNRCEGSSVQTRTCHIQECDKRFKQDGGWSHWSPWSSCSVT
CGDGVITRIRLCNSPSPQMNGKPCEGEARETKACKKDACPINGGWGPWSPWDICSVTC
GGGVQKRSRLCNNPTPQFGGKDCVGDVTENQICNKQDCPIDGCLSNPCFAGVKCTSYP
DGSWKCGACPPGYSGNGIQCTDVDECKEVPDACFNHNGEHRCENTDPGYNCLPCPPRF
TGSQPFGQGVEHATANKQVCKPRNPCTDGTHDCNKNAKCNYLGHYSDPMYRCECKPGY
AGNGIICGEDTDLDGWPNENLVCVANATYHCKKDNCPNLPNSGQEDYDKDGIGDACDD
DDDNDKIPDDRDNCPFHYNPAQYDYDRDDVGDRCDNCPYNHNPDQADTDNNGEGDACA
ADIDGDGILNERDNCQYVYNVDQRDTDMDGVGDQCDNCPLEHNPDQLDSDSDRIGDTC
DNNQDIDEDGHQNNLDNCPYVPNANQADHDKDGKGDACDHDDDNDGIPDDKDNCRLVP
NPDQKDSDGDGRGDACKDDFDHDSVPDIDDICPENVDISETDFRRFQMIPLDPKGTSQ
NDPNWVVRHQGKELVQTVNCDPGLAVGYDEFNAVDFSGTFFINTERDDDYAGFVFGYQ
SSSRFYVVMWKQVTQSYWDTNPTRAQGYSGLSVKVVNSTTGPGEHLRNALWHTGNTPG
QVRTLWHDPRHIGWKDFTAYRWRLSHRPKTGFIRVVMYEGKKIMADSGPIYDKTYAGG
RLGLFVFSQEMVFFSDLKYECRDP" (SEQ ID NO: 2)
``` gene complement(13093..>16389)
  /gene="FSIP1"
  /gene_synonym="HSD 10"
  /note="fibrous sheath interacting protein 1; Derived by automated computational analysis using gene prediction method: BestRefSeq, Gnomon."
  /db_xref="GeneID:161835"
  /db_xref="HGNC:21674"
mRNA complement(13093..>13155)
  /gene="FSIP1"
  /gene_synonym="HSD 10"
  /product="fibrous sheath interacting protein 1, transcript variant X2"
  /note="Derived by automated computational analysis using gene prediction method: Gnomon. Supporting evidence includes similarity to: 1 mRNA, 10 ESTs, 5 Proteins, and 98% coverage of the annotated genomic feature by RNAseq alignments, including 1 sample with support for all annotated introns"
  /transcript_id="XM_005254209.2"
  /db_xref="GI:578826680"
  /db_xref="GeneID:161835"
  /db_xref="HGNC:21674"
mRNA complement(13134..>13155)
  /gene="FSIP1"
  /gene_synonym="HSD 10"
  /product="fibrous sheath interacting protein 1, transcript variant X4"
  /note="Derived by automated computational analysis using gene prediction method: Gnomon. Supporting evidence includes similarity to: 1 mRNA, 10 ESTs, 5 Proteins, and 98% coverage of the annotated genomic feature by RNAseq alignments, including 1 sample with support for all annotated introns"
  /transcript_id="XM_006720417.1"
  /db_xref="GI:578826681"
  /db_xref="GeneID:161835"
  /db_xref="HGNC:21674"
Origin (SEQ ID NO: 1)

```
  1  agccgctgcg cccgagctgg cctgcgagtt cagggctcct gtcgctctcc aggagcaacc
 61  tctactccgg acgcacaggc attccccgcg cccctccagc cctcgccgcc ctcgccaccg
121  ctccggccc ccgcgctccg gtacacacag gtaagtcgcc cccggcggcc gccgaggacc
181  aaagctgccc gggacatcca cctggagcgc tgaggcttca gtccctctgg tggacccgg
241  aacctacact ctccccgctc gcctacccca gcccgctcct ctcagccgct ggaggactct
```

-continued

```
 301 tcagggcaag gctccagagc catcctctcc agccttgagg ttcacaaacc aactcatcag
 361 gacaccccaa gatttcctta ctctctgaag tcctcctaa gcctttgtat cagcactcca
 421 gggaagagtc tgtacttccc ctgccctccc tgcaacccca aactacagtt cctgatcttg
 481 ctcaccttcg acttcccaaa agcccccaaa ttgttggtct tgcgccccc acactttaaa
 541 accagcatct ctttcctcca cctctctctc tctctctctc tctctctctc atgctctctg
 601 gaaagtaatc ctgttgtcct tcatttcagc aaacgcgggg tcaaagaggg atggtcccgg
 661 ccctgtcccc atgcccagcc ccgtttctgc gcaccgtccc tccctgccta gctgatctct
 721 gaccctcggc tcttgtgctt cctgctacag gatccctgct gggcaccaac agctccacca
 781 tggggctggc ctggggacta ggcgtcctgt tcctgatgca tgtgtgtggc accaaccgca
 841 ttccaggtga gtttgtgtgg caccttagg ggaaggaggg acaaggaaga ggtgctggct
 901 atcccaggtg tgcccctca cgtgctgtcc tctccctctt gagcctgact ggacatcagg
 961 acgcagcttc actctgatcc tggtatttat tcacctcttt cagtggttgc caggagtttt
1021 caccccaacc ctttgtctcc acccctaagg actcagcccc tactgctgg tcccagccta
1081 gaaagctcac tttgtgttct ctcctgtcta acagagtctg gcggagacaa cagcgtgttt
1141 gacatctttg aactcaccgg ggccgcccgc aaggggtctg gcgccgact ggtgaagggc
1201 cccgacccctt ccagcccagc tttccgcatc gaggatgcca acctgatccc ccctgtgcct
1261 gatgacaagt tccaagacct ggtggatgct gtgcgggcag aaaagggttt cctccttctg
1321 gcatccctga ggcagatgaa gaagacccgg ggcacgctgc tggccctgga gcggaaagac
1381 cactctggcc aggtcttcag cgtggtgtcc aatggcaagg cgggcaccct ggacctcagc
1441 ctgaccgtcc aaggaaagca gcacgtggtg tctgtggaag aagctctcct ggcaaccggc
1501 cagtggaaga gcatcaccct gtttgtgcag gaagacaggg cccagctgta catcgactgt
1561 gaaaagatgg agaatgctga gttggacgtc cccatccaaa gcgtcttcac cagagacctg
1621 gccagcatcg ccagactccg catcgcaaag gggggcgtca atgacaattt ccaggtgagg
1681 cttcttctct gagccctgct ccgtgggatc atctgctaga caggtgacct gccaggaggg
1741 ctacaggaaa tcctgtctgt aaactaacgc agcagttctc agattttagg cagcatgagc
1801 atcacctgga gggcttgtga agctcaccc tgctgcaccc cagcccaga gtctgggatt
1861 ctgtaaaact gcaactctaa caagtaccag gtgatgctga tgccggtggt ctgggaagca
1921 cactttgaaa actactcaag gaaacaagaa atggttttcc tttagcagtc agcctgttca
1981 agccttagat actccttagg ctcttaagaa aagagcttat ttcaaatgca ttcccccaat
2041 tttaatcttg tttgaaatgg atactttcta tgggcagaat cagtaccact ttgctattgg
2101 attcctcatg gggatgcagc tggtctcaca taaaaggtta aaatagcagt tagttgttgc
2161 tgttacagct tcatctgtgc cttaacttct agatctttgc aacggtggct ttgaactccc
2221 acatttaact ctttgacact ggaaagtgtc attatatcct ctaggcttag gatcagattc
2281 catttcctgt gtacccaagt aggctgataa ctgaattctt tgtaaaatac tcaagacttg
2341 gcagaagtca caattaagat tttgaagttg tttggcgatt aatgttgctg tgttattttg
2401 acatagtgat cttaagacag ctctttgaag cttttagaac atctattgta tgatttcct
2461 agcatacaga cagtctcccc caaccccatc cccacccgc tctgcattct acaagtaatg
2521 tgtgtcctct gcccacaggg ggtgctgcag aatgtgaggt ttgtctttgg aaccacacca
2581 gaagacatcc tcaggaacaa aggctgctcc agctgtgagt accctctat ttttagggca
2641 cataggaat caggggaat tccaccaaaa acaaactgag gaatttagca atagtggta
2701 tacataaatt accccccagtg agatcatcaa gaggcataca gaagtgactc caaggggtat
```

-continued

```
2761  tatacacaca cacgtataca cacgtgcgca tacacgcaac ccctctacct gcatccttca
2821  caccaaatga aacgtcttct accactaaga actcaagagg ctggttggta agagtatcta
2881  tttgaagttt tcattttgtt tcttgccagc taccagtgtc ctcctcaccc ttgacaacaa
2941  cgtggtgaat ggttccagcc ctgccatccg cactaactac attggccaca agacaaagga
3001  cttgcaagcc atctgcggca tctcctgtga tgagctgtcc agcatggtcc tggaactcag
3061  gggcctgcgc accattgtga ccacgctgca ggacagcatc cgcaaagtgg tcagtggcct
3121  ctgcacccag cccgttagca tgaaccctgg aaggtttatc gcagatggtc ccaaatgact
3181  gaaaatgcgg ggggacacta atgatattct ctcccattta gactgaagag aacaaagagt
3241  tggccaatga gctgaggcgg cctcccctat gctatcacaa cggagttcag tacagaaata
3301  acgaggaatg gactgttgat agctgcactg agtgtcactg tcaggtaagg gaccttcacc
3361  agccagaata agaatcgacg gcttttgttt gaacctacat ctttggggaa ataccctaat
3421  cgccacagag attcttttta tgttccatgg cctgataaca aagtgttttt tttttcttta
3481  agatgcaatt atggcatcta taagttcttc tttaaactct cagatggttt atcaaagtat
3541  taattatacc ccaggctaag tatctaagag aatgaatcta ctaagacatc tgaataattt
3601  acctacctta gttcaaagac taagtgttga atgtcaggta aataaaacct ggttggaaca
3661  ttcatttttt ttcccaacc ctgatttata ttcagctttg cataggttc ttttagtaca
3721  gtagcaattg tttttcaaat cacttagtct gacactgtta ggatgttact gtctgctttg
3781  ctcagatggc actgccaggt gtgtgattca ctctagcatc cccgcatgcc agtggccagt
3841  gagtttggag gttcacctgg cttatctatt aatagcaaag tatttgaatt tgcttaaata
3901  caaatcacag atgactggct gtgggaacca acttcattaa attccctttc ttttccaata
3961  taaagacaga tcacagatct atagatgagg aaaaagtgct tatagatctt ccttcctccc
4021  cccaaacaca taatataaaa atgtaaaagt cctggctgaa ttttctgagt ttgatttcag
4081  acatagattt gacccatgat gtttgttggt tcctctgcta taaattcttt gtactgtaac
4141  ttccacccct gactaagtag caattaaaaa gaactttcca aggaatggag tgacacgtaa
4201  actagcacta gaactgtctc tacgatagtg gtggctgcaa atatgacaga gacagatcta
4261  tgaaaatcat tccactagag cattgacagc cctgaccatg ttttggcttg taaaggaaat
4321  gttacaggat gtagacttct gtatgcaaca tgctcagcag cctgttcccc tctcactctc
4381  ttgccctgca gaactcagtt accatctgca aaaggtgtc ctgccccatc atgccctgct
4441  ccaatgccac agttcctgat ggagaatgct gtcctcgctg ttggcgtaag tttctcaaat
4501  ggcatagcta ttcttcagtg actaggtcag ttctacatac atcctagaca gccgagcaca
4561  acactggaac cccaccccca tctccatcat gcttccattc agtttcttgc tgcagcagct
4621  ggttaactga cagcttatct gctgtacaga gccaaaactc cattatgagt acatcgtaat
4681  tacccatctg gattgcagta atggcagtga agatcttggt atagctcatt aattctgatt
4741  ttttgctttg aggaaaagag atgaagacgt ggcagcaaca gctctaagtt gactgctttt
4801  agaatttgac cttagtggca cagagttaag aaaaatctgc tcaccagaga tattgacagg
4861  cttactgtgt aagcattggc ctgatcgggc ctggaagttt tgccccttc atctgtaggg
4921  ataagagggc taagagaat agcagcaatc tgagctctag agcaccaaaa gaaataaggc
4981  acgatatcgt tccatggcac gttatccctg gcttttgtta ccagtaaaat gaatgacttt
5041  gctgagacaa tacttagtgt agcaggtaca agttataaaa gtgattcatt acaactaaga
5101  taaggaagaa aacaggaaaa cagcacttgc ccttcacaca cacagaaaca cacatgcaca
5161  cacacacaaa cacaccctig tcacagctca gaataaccaa ttccatccag ggatcatatt
```

-continued

```
5221  agcgatattg gcactgtaat ggtcgttttt acatttattt tctgttccgc attcacttaa
5281  catgtgcgtt aaaaggaaca aagctagctg gaggtagcaa agttttgaac ttgaatcagg
5341  gattgctaag aaaacttaca actaatgacc acagaaagta agttctttgt cttctgtctg
5401  atacagctag atgtgattgt agccgtggtg cctgggcaga tggtaaacaa acatgctgtc
5461  ctcttatgac aatatgtgca gagaaggccc caaacgctgg ggtgagagga acaacaaact
5521  gactaactca cggccgagtt ggagccagaa ccaacaacag ctcggctgcc ttcacactca
5581  tctgtcaaac acatggtgta tggctcccct gacagaaatg actcctataa gcttcctcat
5641  actcgcgcat tcttggaagt ctgagactgg aaatgcctac ccagatatgt taagtcagta
5701  aaggaaaact catttgcaat gctgagagga gaaagaaaat caatgaatag gagagcatac
5761  actgtgggaa ggctcagctg tactgagcca ggcaaagcat ccgattaccc cactgctgta
5821  cacatcatga cctgggataa accctgggc cgttggccta agaaatatgt tgcttttcat
5881  cctgtataac tgcaactttg tgccggctca tattatgttc tagagagctc atgtacacca
5941  tggtgaccat agttaataat actggattgt atgcttaaaa tttgctaaga gagtagatct
6001  taagtcatca ccaaaaaaag taactgtaag atgatggaga tgtgttaatt agcttgacgg
6061  tggtaatcac aatatatgtg tatatcaaaa catcacatta tacaccttaa atgtatataa
6121  tatttgtcaa ttatacctca gtaaagccaa aaagaaataa atatattgct tttcaccctc
6181  tggcaagtgg agggccctga acagagccct ctaaagaaca gcttgtccta atcatcacgt
6241  acctgatgaa cctctgtttc ccctgcagcc agcgactctg cggacgatgg ctggtctcca
6301  tggtccgagt ggacctcctg ttctacgagc tgtggcaatg gaattcagca gcgcggccgc
6361  tcctgcgata gcctcaacaa ccgatgtgag ggctcctcgg tccagacacg gacctgccac
6421  attcaggagt gtgacaagag atgtaagcat cttagcctct cagggacgtg gagaactgac
6481  ctgtccttgt tgtcgtcacc aagggcagct ccacagcatg tatattaaga acacgggttc
6541  taggatctct ggatcccaat cccactgctt agctgtgcac ccttgaacac aacttaccct
6601  ctctgaggct ctttcctcat ttgcaacttg gagataataa tagttcttga taagtttatc
6661  ttgagcattt tatttagata ctgcatgtaa agcagttagc actgagtttt ggtttatggt
6721  aagcaccctg taaatgttag gatattaaca gcaacccata aaaacagcga acttatccgt
6781  tctctggtag aaaacattcc atgttgacat ttgggcatgt ggccaggagc caatttctac
6841  cgtacactgg gtttagttgc cattgaccat ttcctggaaa tacttctgcg tgctcctgat
6901  gggagcctct atttggctgt ctctaagcca aaaccatttg tgaccatcaa ctctgtactt
6961  tagttaaaca ggatggtggc tggagccact ggtccccgtg gtcatcttgt tctgtgacat
7021  gtggtgatgg tgtgatcaca aggatccggc tctgcaactc tcccagcccc cagatgaacg
7081  ggaaaccctg tgaaggcgaa gcgcgggaga ccaaagcctg caagaaagac gcctgcccca
7141  gtaagtgtga ggtccgctgc aagggtgagc atgggcagca gctctgccca gctggttgcc
7201  tggcatctgc agcctgcagt tcagtgggtc atagagcagg aaggttacct actagagaaa
7261  caaacagaag caaagtcctg caggctcagc aacttctttt aatgaaaaac aaactcaccc
7321  tcttccccag cattcttttcc atgtgtcaga gaagcagagg tttcttgaac gggcttagga
7381  gagtctatga caagggaggg atttgaaagt tgatcttaat tgttgcctgt ggttcatctt
7441  cttacagtca atggaggctg gggtccttgg tcaccatggg acatctgttc tgtcacctgt
7501  ggaggagggg tacagaaacg tagtcgtctc tgcaacaacc ccacacccca gtttggaggc
7561  aaggactgcg ttggtgatgt aacagaaaac cagatctgca acaagcagga ctgtccaatt
7621  ggtgagccac gcagcccagg atgaaacgac ccaggagctt tgctctttta ctgaatgctg
```

-continued

```
7681 cagtcagcat tcgaggagat tccagcttgg ttagtcctga gcgatttgat tgctctaaga
7741 tgcaggtgga caacataatc ccaacaagtt atcggttccc tatacccctat aatatcttac
7801 actgtgttaa gtgcccagca tggcagtatg cagcttaga ccaaccattt actgtgactg
7861 tctctctctc cttgtctcag atggatgcct gtccaatccc tgctttgccg gcgtgaagtg
7921 tactagctac cctgatggca gctggaaatg tggtgcttgt cccctggtt acagtggaaa
7981 tggcatccag tgcacagatg ttgatgaggt gaggaactga tggggctccg agtttctgga
8041 tctaggaaag cagctaacct gtgcagtcgc ttccttatgg cagtgacttc taaacatgat
8101 gcacgctctt atttcctcca tagtgcaaag aagtgcctga tgcctgcttc aaccacaatg
8161 gagagcaccg tgtgagaac acggaccccg gctacaactg cctgccctgc cccccacgct
8221 tcaccggctc acagcccttc ggccagggtg tcgaacatgc cacggccaac aaacaggtac
8281 agtcaactag acgagtaaac cagaggacag gagagctgtc cttgaccaaa taactggga
8341 gcgggaggaa tgtaatttca tacccttcac caaaaaaaaa agggcgagga gatgaatgta
8401 cggtctagtt ttagaaacgt gattagaaaa tccatggtaa atcctgcagg ggaaaaacag
8461 tcttccatat ttaaaaatgc tgctctggaa taagttgtga gcagatggac ttgtaaacgc
8521 ctaggtgctg agcaaattca agaaaaataa acataaagca aagtttgctt atagcctcag
8581 ggagaatggg gagggacaga ggtaacccac actcttccaa atggagcctc tgtctactca
8641 gagatgacag ggatctggat tcttgtttcc atgatatctg aggattctca aaagctctgt
8701 gtaacagcag catggtgtac cctcaggtgt gcaagccccg taacccctgc acggatggga
8761 cccacgactg caacaagaac gccaagtgca actacctggg ccactatagc gacccccatgt
8821 accgctgcga gtgcaagcct ggctacgctg gcaatggcat catctgcggg gaggacacag
8881 acctggatgg ctggcccaat gagaacctgg tgtgcgtggc caatgcgact taccactgca
8941 aaaaggtaga gccaggtcct ttgtgtgcct ccagaaagag ggcccatcac cttatcaaaa
9001 cacaggctaa ggaatttttaa atacttaaag tttggacatg aaactgaaag attaaatctc
9061 ccaaagggag aggggcacta attcctatta aaattaaatc acttggtgcc aaaaacatga
9121 acagggctag ctcttttttgg gcaactgtgt tccatagtca actcttctgt ccaaaaaaaa
9181 gttcagtact ctatccaaat accagcaaag catgacttgt gttcacaaca tctataaagc
9241 ctagagcatt tacacaaatt ctgtatgtat atcccccaag aaaagtttta ttttcttgtc
9301 ttcccataaa aaaaatatgc tgttactgag ccaaattctg ttcttttttct atttggaatt
9361 ccaggtacac tccctcgtgc atgagctcag catgaggaag gcaactgaag cagtgatata
9421 tatcttctct ttcctaggat aattgcccca accttcccaa ctcagggcag gaagactatg
9481 acaaggatgg aattggtgat gcctgtgatg atgacgatga caatgataaa attccagatg
9541 acagggtaaa aacagttttc tatccdttt tcatcttttc agttcagcaa cagcctgaaa
9601 cactttggga ttcaaggaaa ttacatggct atagcaaaaa atataccaaa tcaatacaca
9661 ggataattag aaattattca ttgtgttcca gtagtttaag gatgtagatg ttgccaagag
9721 aattttaaaa tgagggtttt gttttttcatc agaactgttt ttctctgtac ttgagaaatt
9781 ataatgcata aacaaatgcc actttgttcc ctagattcat ttcaaatgtc acatcgaaat
9841 tacagtaaaa ttgacttttgg gcacactatg aactgagatg atgggattat attctacatc
9901 tcactaactt ctaacccaca gggatccatt tttttaacta tgtccttta acttttgtag
9961 tgatcgtttt acactgagtg atcaattagc ctatccacta ggtagaaagt attgctgatt
10021 ttcacagttt tagacatatt atgcacatgg tttgaggctt gagctgtttt caaggacaac
10081 attgttaagt gctccatttc ttctctttgc aggacaactg tccattccat tacaacccag
```

-continued

```
10141 ctcagtatga ctatgacaga gatgatgtgg gagaccgctg tgacaactgt ccctacaacc
10201 acaacccaga tcaggcagac acagacaaca atggggaagg agacgcctgt gctgcagaca
10261 ttgatggaga cggtaaggtg ctgcctgatc agagggcccg cgggagacag ggacatgcac
10321 agctttccaa acgtacttct gtctagtcct ggctattagt atgcactttg gtggaaacat
10381 ccaaggctgg agagcccagc tcttatttgt cccttgttct cttcaggtat cctcaatgaa
10441 cgggacaact gccagtacgt ctacaatgtg gaccagagag acactgatat ggatggggtt
10501 ggagatcagt gtgacaattg ccccttggaa cacaatccgg atcaggtagg tggatggact
10561 cctttcagag tctttcagta aactgttgga atatcccttt catggccttt gaaaaatgag
10621 cttaacaaag ttcaaacact ttcattactg tggctccctg gcttctcata ccaactgga
10681 atacgttcat gtaaataatt tgcctgatgt gagctccttg cacagagtct cacagatctt
10741 tagcatgaag atctggtaac ttcagtctta ccttctgtaa gaagggctac tggacttgct
10801 cagcatcgtc taccattgtt aagacaaatt atacaaagca gacatctgtg actgacaact
10861 gtacaataat attaatcata tgtaatacta agagatgaa aaataaatgt gcataagcaa
10921 aataaccatt ttcatggcta atgatgtaat ctagctataa gaaaatcatc aaactaagga
10981 tacatccaaa accaaagtaa tttatccctg tcataaacat tacccagaca gtatacaaca
11041 cagggaccag tggtctgttt ccatcttttc aggacttttc agagaagtcg acgtgtcaac
11101 agttttacaa ctgaaacctt ctaaggaaat tctctgttat aaagtatcca gaaatttca
11161 tttaacatta agatgtaaac agttaacatt tcatttcatc tttagtaatt aaatatcact
11221 ctatttgacc ttatttagaa agttttatat gtaaaacatt tttaaattat ccatctcag
11281 attttatac gaaaacaaag ataaaggaaa aaaacttttta aaatgtaatt gctactattg
11341 ctatctttct gcaggagtgt gtaaatagac atgacacccc actggctgta tcaaacaatg
11401 gagaattttc cctgtggtgg gggcataagt tatctttaac atgaatggtt tatactgcaa
11461 tttaccctcc atttacatct ctattcagc tggactctga ctcagaccgc attggagata
11521 cctgtgacaa caatcaggat attgatgaag atggccacca gaacaatctg gacaactgtc
11581 cctatgtgcc caatgccaac caggctgacc atgacaaaga tggcaaggga gatgcctgtg
11641 accacgatga tgacaacgat ggcattcctg atgacaagga caactgcaga ctcgtgccca
11701 atcccgacca gaaggactct gacggtgagt catgggagcc actttctaag acagggactg
11761 ctggcacagc tgtgtagatt gaagaaatga aaccaaggct caaagcattt gacaggatga
11821 agggaccaaa tgccaactta gacaagatag tgacatttct gacaccagta ataataatag
11881 cactttagaa ttttgctgaa ctcttgcttt tttgacctca ggcgatggtc gaggtgatgc
11941 ctgcaaagat gattttgacc atgacagtgt gccagacatc gatgacatct gtcctgagaa
12001 tgttgacatc agtgagaccg atttccgccg attccagatg attcctctgg accccaaagg
12061 gacatcccaa aatgacccta actgggttgt acgccatcag ggtaaagaac tcgtccagac
12121 tgtcaactgt gatcctggac tcgctgtagg tgagtagcga gttcttagat cctaagagac
12181 tgatgcatac atggggaaaa acaaatataa aacctggcag ttgtacctat ccctgtgggt
12241 gctgaggatg tctaggaaca tgatggagaa ccttctgaag gctgcaggtt ttaacctggc
12301 tctgggctct tcttccaggt tatgatgagt ttaatgctgt ggacttcagt ggcaccttct
12361 tcatcaacac cgaaagggac gatgactatg ctggatttgt ctttggctac cagtccagca
12421 gccgctttta tgttgtgatg tggaagcaag tcacccagtc ctactgggac accaaccccca
12481 cgagggctca gggatactcg ggccttttctg tgaaagttgt aaactccacc acagggcctg
12541 gcgagcacct gcggaacgcc ctgtggcaca caggaaacac ccctggccag gtaagaagca
```

-continued

```
12601 aagccctgga acagagagag agcttatggg tgcctgacta gcactgggga tgctgtgctt
12661 tgaccaagac tctgaccagg gagtcttaga aagttcccag catcaccagc tgcagcattg
12721 aactctgctt tgtaaaaaca taatagtgtt gaaaagggag cttgaccaag aattgccctg
12781 caaatcctaa ggtgccttca gccttttcaa acaaaaaaac ctccttccct cctctctgtc
12841 tgctttatat gtgtgctcag tggcacacaa caaatatgag aggacttgga aaaattcccc
12901 attgcagccc tctaacttag atcagctcag tacctttcaa gcattgtttc tgatggaatg
12961 aaatagaaat ctttacctga aggagctgtg tttcaacctt tcctttcct tttccttcag
13021 gtgcgcaccc tgtggcatga ccctcgtcac ataggctgga aagatttcac cgcctacaga
13081 tggcgtctca gccacaggcc aaagacgggt ttcattaggt acgatcatac tgattcactt
13141 tcacttacag tcacactgag ggacaaaaag acaaaaagta ttaaatagca ttgtcactaa
13201 acaagatttt ttttccctgc agagtggtga tgtatgaagg gaagaaaatc atggctgact
13261 caggacccat ctatgataaa acctatgctg gtggtagact agggttgttt gtcttctctc
13321 aagaaatggt gttcttctct gacctgaaat acgaatgtag aggtaagagc aacatcacca
13381 tgaatgtaca ctggacatct ctatttcaga ctaatatcaa ggatgacggt tatggggag
13441 tccagtgtaa agactgtttt ggagacaggg ttatttctat tttgcttttg aggacacaag
13501 gacaaaaatg gaataatgcc taggcactgt ggcttatgag ttcctgagtc cttagctata
13561 atattagttt gcttagcaat ctctgtgctc ctcatacaca gtgcaaggt aagctgcaga
13621 aaagctccta tataatttgg acttcattaa taatactgtt ctttacaatt atatatttat
13681 atatcttact gcttattgtt ttatgcatgc catcacagca cgagttagca ttcccaactt
13741 ttccctgtat acaaagaagg gagaggaatg ttgctttcat attggcatgt taaattaatg
13801 ttcactatta aacttagcat ttttttcct cattcttttt tacttagtca ttacttaagc
13861 tcgctgagtc caacactggc tctaccacaa aataagtgct taatatatat ttactgggcc
13921 aaggccagat acctaaaaga tcaatgacag tagagaaaga tggttgattt tactcaaaaa
13981 aatctaaatt attaatgtaa ttttgagtc caaattttta aaataagact ccctaaactg
14041 ttaacattga aagcctttgg aaagcataat atatgttctg gaaggttcac gctgtgtcgg
14101 tctcctagca tcaatgtcag ctaataaaat taaatgctaa tgtgcttgaa caaccttaaa
14161 attaggcttt tgtcattaga aaagtagagc tattcctatg tggttaactt attaactaag
14221 atgtctatgc ttttatgaat tagttttcat ttgtatattt atttatattt gtttatttaa
14281 cagatcccta atcatcaaat tgttgattga aagactgatc ataaaccaat gctggtattg
14341 caccttctgg aactatgggc ttgagaaaac ccccaggatc acttctcctt ggcttccttc
14401 ttttctgtgc ttgcatcagt gtggactcct agaacgtgcg acctgcctca agaaaatgca
14461 gttttcaaaa acagactcag cattcagcct ccaatgaata agacatcttc caagcatata
14521 aacaattgct ttggtttcct tttgaaaaag catctacttg cttcagttgg gaaggtgccc
14581 attccactct gcctttgtca cagagcaggg tgctattgtg aggccatctc tgagcagtgg
14641 actcaaaagc attttcaggc atgtcagaga agggaggact cactagaatt agcaaacaaa
14701 accaccctga catcctcctt caggaacacg gggagcagag gccaaagcac taaggggagg
14761 gcgcataccc gagacgattg tatgaagaaa atatggagga actgttacat gttcggtact
14821 aagtcatttt caggggattg aaagactatt gctggatttc atgatgctga ctggcgttag
14881 ctgattaacc catgtaaata ggcacttaaa tagaagcagg aaagggagac aaagactggc
14941 ttctggactt cctccctgat ccccacccctt actcatcacc tgcagtggcc agaattaggg
15001 aatcagaatc aaaccagtgt aaggcagtgc tggctgccat tgcctggtca cattgaaatt
```

-continued

```
15061 ggtggcttca ttctagatgt agcttgtgca gatgtagcag gaaaatagga aaacctacca 15121 tctcagtgag caccagctgc ctcccaaagg aggggcagcc gtgcttatat ttttatggtt 15181 acaatggcac aaaattatta tcaacctaac taaaacattc ctttttctctt ttttcctgaa 15241 ttatcatgga gttttctaat tctctctttt ggaatgtaga tttttttttaa atgctttacg 15301 atgtaaaata tttatttttt acttattctg gaagatctgg ctgaaggatt attcatgaa 15361 caggaagaag cgtaaagact atccatgtca tctttgttga gagtcttcgt gactgtaaga 15421 ttgtaaatac agattattta ttaactctgt tctgcctgga aatttaggct tcatacggaa 15481 agtgtttgag agcaagtagt tgacatttat cagcaaatct cttgcaagaa cagcacaagg 15541 aaaatcagtc taataagctg ctctgcccct tgtgctcaga gtggatgtta tgggattctt 15601 tttttctctg ttttatcttt tcaagtggaa ttagttggtt atccatttgc aaatgtttta 15661 aattgcaaag aaagccatga ggtcttcaat actgttttac cccatccctt gtgcatattt 15721 ccagggagaa ggaaagcata tacacttttt tctttcattt ttccaaaaga gaaaaaatg 15781 acaaaaggtg aaacttacat acaaatatta cctcatttgt tgtgtgactg agtaaagaat 15841 ttttggatca agcggaaaga gtttaagtgt ctaacaaact taaagctact gtagtaccta 15901 aaaagtcagt gttgtacata gcataaaaac tctgcagaga agtattccca ataaggaaat 15961 agcattgaaa tgttaaatac aatttctgaa agttatgttt ttttctatc atctggtata 16021 ccattgcttt attttataa attattttct cattgccatt ggaatagata tctcagattg 16081 tgtagatatg ctatttaaat aatttatcag gaaatactgc ctgtagagtt agtatttcta 16141 tttttatata atgtttgcac actgaattga agaattgttg gttttttctt tttttttgttt 16201 tgttttttttt ttttttttttt tttgcttttg acctcccatt tttactattt gccaatacct 16261 ttttctagga atgtgctttt ttttgtacac attttttatcc atttttacatt ctaaagcagt 16321 gtaagttgta tattactgtt tcttatgtac aaggaacaac aataaatcat atggaaattt 16381 atatttata
```

SNP1 rs1478604 [*Homo sapiens*] (SEQ ID NO:3)
Chromosome: 15:39873321
Gene: THBS1 (GeneView)
Functional Consequence:
utr variant 5 prime
Validated: by 1000 G, by 2 hit 2 allele, by cluster, by frequency, by hapmap, by submitter
Global MAF:
C=0.4100/892
HGVS: NC_000015.9:g.39873321T>C, NM_003246.2:c.-138T>C, NT_010194.17:g.10663878T>C
RefSNP Alleles: A/G (REV): Allele is reported in reverse orientation to genome—R is A or G

```
                                                 (SEQ ID NO: 3)
     GTTTTAAAGT GTGGGGGGCG CAAGACCAAC AATTTGGGGG

CTTTTGGGAA GTCGAAGGTG AGCAAGATCA GGAACTGTAG

TTTGGGGTTG CAGGGAGGGC AGGGGAAGTA CAGACTCTTC

CCTGGAGTGC TGATACAAAG GCTTAAGGAG GACTTCAGAG

AGTAAGGAAA TCTTGGGGTG TCCTGATGAG TTGGTTTGTG

AACCTCAAGG CTGGAGAGGA TGGCTCTGGA GCCTTGCCCT
```

-continued

```
     GAAGAGTCCT CCAGCGGCTG AGAGGAGCGG GCTGGGGTAG

GCGAGCGGGG AGAGTGTAGG TTCCGGGGTC CACCAGAGGG

ACTGAAGCCT CAGCGCTCCA GGTGGATGTC CCGGGCAGCT

TTGGTCCTCG GCGGCCGCCG GGGGCGACTT ACCTGTGTGT

ACCGGAGCGC GGCGGCCGGG AGCGGTGGCG AGGGCGGCGA

GGGCTGGAGG GGCGCGGGGA ATGCCTGTGC GTCCGGAGTA

GAGGTTGCTC CTGGAGAGCG R CAGGAGCCCT GAACTCGCAG

GCCAGCTCGG GCGCAGCGGC TGGCAAGGCG GAGGAGCCGC

GCGCTTTTAA AGGGGCGCTC GCATTCCTGG GGATTCCTCC

GGCCAATGGG CGGCGGCCGG GCAGGAAGCG GGAGGTGGGG

GCCAGTCTGG GCTCCTCTCT CCGCCCCCCG CTGCCTGGCG

CGCAACTTTC CAGCTAGAAA GTGAAGGGGG CGGGGGTCGG

GGCTTGGGAG CACTAGAACT TCTCAGAAAA GTCGGTGCCC

GCCCACGCAG CCTTGGCGCG CACGGGCTCG GCGCTCGTAC

TCTTGCGCCA CGCGGGCTCG GGGTGATCAG CAAGCATCCC
```

```
GAAAAGGGAC GGGGCTGGGG AGACCACCTA GGAGGGCCCG

CGGGGTGGCG CAGGGGCTTT CGGGCGAGCT GATCTCCCGG

AATGCCTGGT TGATGGCGAG AGGTGGATAC TAGAGACTGG

GCCCGTTTTG TAAAAAGAAA AATGGGCCGA CGGGGCGCAG
```

SNP2 rs2228261 [Homo sapiens] (SEQ ID NO: 4)
Chromosome: 15:39880358
Gene: THBS1 (GeneView)
Functional Consequence:
synonymous codon
Validated: by 1000G, by cluster, by frequency, by hapmap
Global MAF:
T=0.2420/526
HGVS: NC_000015.9:g.39880358C>T, NM_003246.2:c.1410C>T, NP_003237.2:p.Asn470, NT_010194.17:g.10670915C>T
RefSNP Alleles: C/T (FWD) Allele is reported in forward orientation to genome—Y is C or T

```
                                              (SEQ ID NO: 4)
ACCCTTGAAC ACAACTTACC CTCTCTGAGG CTCTTTCCTC

ATTTGCAACT TGGAGATAAT

AATAGTTCTT GATAAGTTTA TCTTGAGCAT TTTATTTAGA

TACTGCATGT AAAGCAGTTA

GCACTGAGTT TTGGTTTATG GTAAGCACCC TGTAAATGTT

AGGATATTAA CAGCAACCCA

TAAAAACAGC GAACTTATCC GTTCTCTGGT AGAAAACATT

CCATGTTGAC ATTTGGGCAT

GTGGCCAGGA GCCAATTTCT ACCGTACACT GGGTTTAGTT

GCCATTGACC ATTTCCTGGA

AATACTTCTG CGTGCTCCTG ATGGGAGCCT CTATTTGGCT

GTCTCTAAGC CAAAACCATT

TGTGACCATC AACTCTGTAC TTTAGTTAAA CAGGATGGTG

GCTGGAGCCA CTGGTCCCCG

TGGTCATCTT GTTCTGTGAC ATGTGGTGAT GGTGTGATCA

CAAGGATCCG GCTCTGCAAC

TCTCCCAGCC CCCAGATGAA Y GGGAAACCCT GTGAAGGCGA

AGCGCGGGAG ACCAAAGCCT GCAAGAAAGA CGCCTGCCCC

AGTAAGTGTG AGGTCCGCTG CAAGGGTGAG CATGGGCAGC

AGCTCTGCCC AGCTGGTTGC CTGGCATCTG CAGCCTGCAG

TTCAGTGGGT CATAGAGCAG GAAGGTTACC TACTAGAGAA

ACAAACAGAA GCAAAGTCCT GCAGGCTCAG CAACTTCTTT

TAATGAAAAA CAAACTCACC CTCTTCCCCA

CATGTGTCAG AGAAGCAGAG GTTTCTTGAA CGGGCTTAGG

AGAGTCTATG ACAAGGGAGG GATTTGAAAG TTGATCTTAA

TTGTTGCCTG TGGTTCATCT TCTTACAGTC AATGGAGGCT

GGGGTCCTTG GTCACCATGG GACATCTGTT CTGTCACCTG

TGGAGGAGGG GTACAGAAAC GTAGTCGTCT CTGCAACAAC

CCCACACCCC AGTTTGGAGG CAAGGACTGC GTTGGTGATG
```

SNP3 rs2292305 [Homo sapiens] (SEQ ID NO: 5)
Chromosome: 15:39880822
Gene: THBS1 (GeneView)
Functional Consequence:
missense
Validated: by 1000 G, by 2 hit 2 allele, by cluster, by frequency, by hapmap
Global MAF:
G=0.2534/552
HGVS: NC_000015.9:g.39880822A>G, NM_003246.2:c.1567A>G, NP_003237.2:p.Thr523Ala, NT_010194.17:g.10671379A>G
RefSNP Alleles: C/T (REV) Allele is reported in reverse orientation to genome—Y is C or T

```
                                              (SEQ ID NO: 5)
AGATCCAGAA ACTCGGAGCC CCATCAGTTC CTCACCTCAT

CAACATCTGT GCACTGGATG

CCATTTCCAC TGTAACCAGG GGGACAAGCA CCACATTTCC

AGCTGCCATC AGGGTAGCTA

GTACACTTCA CGCCGGCAAA GCAGGGATTG GACAGGCATC

CATCTGAGAC AAGGAGAGAG AGACAGTCAC AGTAAATGGT

TGGTCTAAGC TGCCATACTG CCATGCTGGG CACTTAACAC

AGTGTAAGAT ATTATAGGGT ATAGGGAACC GATAACTTGT

TGGGATTATG TTGTCCACCT GCATCTTAGA GCAATCAAAT

CGCTCAGGAC TAACCAAGCT GGAATCTCCT CGAATGCTGA

CTGCAGCATT CAGTAAAAGA GCAAAGCTCC TGGGTCGTTT

CATCCTGGGC TGCGTGGCTC ACCAATTGGA CAGTCCTGCT

TGTTGCAGAT CTGGTTTTCT GTTACATCAC CAACGCAGTC

CTTGCCTCCA AACTGGGGTG Y GGGGTTGTTG CAGAGACGAC

TACGTTTCTG TACCCCTCCT CCACAGGTGA CAGAACAGAT

GTCCCATGGT GACCAAGGAC CCCAGCCTCC ATTGACTGTA

AGAAGATGAA CCACAGGCAA CAATTAAGAT CAACTTTCAA

ATCCCTCCCT TGTCATAGAC TCTCCTAAGC CCGTTCAAGA

AACCTCTGCT TCTCTGACAC ATGGAAAGAA TGCTGGGGAA

GAGGGTGAGT TTGTTTTTCA TTAAAAGAAG TTGCTGAGCC

TGCAGGACTT TGCTTCTGTT TGTTTCTCTA GTAGGTAACC

TTCCTGCTCT ATGACCCACT GAACTGCAGG CTGCAGATGC

CAGGCAACCA GCTGGGCAGA GCTGCTGCCC ATGCTCACCC

TTGCAGCGGA CCTCACACTT ACTGGGCAG GCGTCTTTCT

TGCAGGCTTT GGTCTCCCGC GCTTCGCCTT CACAGGGTTT

CCCGTTCATC TGGGGCTGG GAGAGTTGCA GAGCCGGATC
```

I claim:

1. A method for treatment of dry eye comprising:
   a. obtaining a biological sample from an individual,
   b. detecting the presence of at least one single nucleotide polymorphism (SNP) in the THBS1 gene in the biological sample using a method selected from the group consisting of: single-strand conformational polymorphism (SSCP) analysis, long range polymerase chain reaction (PCR) and allele specific hybridization, wherein the SNP is selected from the group consisting of: the presence of a cytosine "C" allele at position 42 of SEQ ID NO: 1, or its complement thereof (SNP1); the presence of a thymine "T" allele at position 7079 of SEQ ID NO: 1, or its complement thereof (SNP2); and the presence of a guanine "G" allele at position 7543 of SEQ ID NO: 1, or its complement thereof (SNP3), and
   c. administering to an individual who has at least one SNP as determined in step (b), a pharmaceutically effective amount of a dry eye therapeutic.

2. The method of claim 1, wherein a pharmaceutically effective amount of a dry eye therapeutic is administered to an individual that has the presence of at least two single nucleotide polymorphisms (SNPs) of step (b).

3. The method of claim 1, wherein a pharmaceutically effective amount of a dry eye therapeutic is administered to an individual that has the presence of all three single nucleotide polymorphisms (SNPs) of step (b).

4. The method of claim 1, wherein the biological sample is selected from the group consisting of: a tissue biopsy, whole blood, plasma, serum urine, saliva, cerebrospinal fluid and a conjunctival impression cytology (CIC) sample.

5. The method of claim 1, further comprising measuring expression of interleukin-1 beta in the biological sample.

6. The method of claim 1, wherein the individual is in need of refractive eye surgery.

7. The method of claim 1, wherein the dry eye therapeutic is a lubricating substance or an immunosuppressant.

* * * * *